(12) United States Patent
Geuten et al.

(10) Patent No.: US 10,472,645 B2
(45) Date of Patent: Nov. 12, 2019

(54) METHODS AND MEANS FOR MODULATING FLOWERING TIME IN MONOCOT PLANTS

(71) Applicants: BAYER CROPSCIENCE NV, Diegem (BE); BAYER CROPSCIENCE LP, Durham, NC (US)

(72) Inventors: Koen Geuten, Kessel-Lo (BE); Kerstin Kaufmann, Potsdam-Golm (DE); Philip Ruelens, Leuven (BE)

(73) Assignees: BASF SE, Ludwigshafen am Rhein (DE); BAYER CROPSCIENCE NV, Diegem (BE)

( * ) Notice: Subject to any disclaimer, the term of this patent is extended or adjusted under 35 U.S.C. 154(b) by 262 days.

(21) Appl. No.: 14/902,317

(22) PCT Filed: Jul. 1, 2014

(86) PCT No.: PCT/EP2014/063985
§ 371 (c)(1),
(2) Date: Dec. 30, 2015

(87) PCT Pub. No.: WO2015/000914
PCT Pub. Date: Jan. 8, 2015

(65) Prior Publication Data
US 2017/0051295 A1 Feb. 23, 2017

(30) Foreign Application Priority Data
Jul. 1, 2013 (EP) .................................. 13174566

(51) Int. Cl.
| | | |
|---|---|---|
| C12N 15/82 | (2006.01) | |
| C07K 14/47 | (2006.01) | |
| C07K 14/415 | (2006.01) | |
| C12Q 1/6895 | (2018.01) | |

(52) U.S. Cl.
CPC .......... *C12N 15/827* (2013.01); *C07K 14/415* (2013.01); *C07K 14/4703* (2013.01); *C12N 15/8218* (2013.01); *C12N 15/8222* (2013.01); *C12N 15/8267* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,268,526 A | 12/1993 | Hershey et al. |
| 5,510,471 A | 4/1996 | Lebrun et al. |
| 5,538,880 A | 7/1996 | Lundquist et al. |
| 5,570,386 A | 10/1996 | Capasso et al. |
| 5,571,706 A | 11/1996 | Baker et al. |
| 5,589,583 A | 12/1996 | Klee et al. |
| 5,589,615 A | 12/1996 | De Clercq et al. |
| 5,593,874 A | 1/1997 | Brown et al. |
| 5,597,945 A | 1/1997 | Jaynes et al. |
| 5,602,321 A | 2/1997 | John |
| 5,608,148 A | 3/1997 | John |
| 5,618,988 A | 4/1997 | Hauptmann et al. |
| 5,619,042 A | 4/1997 | Hughes |
| 5,641,876 A | 6/1997 | McElroy et al. |
| 5,659,122 A | 8/1997 | Austin |
| 5,677,175 A | 10/1997 | Hodges et al. |
| 5,681,730 A | 10/1997 | Ellis |
| 5,750,871 A | 5/1998 | Moloney et al. |
| 5,773,269 A | 6/1998 | Somers et al. |
| 5,773,697 A | 6/1998 | Tomes et al. |
| 5,780,708 A | 7/1998 | Lundquist et al. |
| 5,783,393 A | 7/1998 | Kellogg et al. |
| 5,736,369 A | 8/1998 | Bowen et al. |
| 5,792,929 A | 8/1998 | Mariani et al. |
| 5,837,848 A | 11/1998 | Ely et al. |
| 5,905,186 A | 5/1999 | Thomas et al. |
| 6,423,885 B1 | 7/2002 | Waterhouse et al. |
| 6,453,242 B1 | 9/2002 | Eisenberg et al. |
| 6,635,805 B1 | 10/2003 | Baulcombe et al. |
| 6,784,340 B1 | 8/2004 | Aoyama et al. |
| 7,888,552 B2 | 2/2011 | Ye et al. |
| 2003/0037355 A1 | 2/2003 | Barbas, III et al. |
| 2003/0180945 A1 | 9/2003 | Wang et al. |
| 2005/0091717 A1* | 4/2005 | Amasino .............. C12N 15/827 800/287 |
| 2005/0144667 A1 | 6/2005 | Stanley et al. |

FOREIGN PATENT DOCUMENTS

| | | |
|---|---|---|
| EP | 0633317 A1 | 1/1995 |
| WO | WO-87/07644 A1 | 12/1987 |
| WO | WO-89/03887 A1 | 5/1989 |
| WO | WO-89/10396 A1 | 11/1989 |
| WO | WO-90/12107 A1 | 10/1990 |

(Continued)

OTHER PUBLICATIONS

Sequence Accession G1FP79, Oct. 19, 2011, sequence alignement is attached to office action.*
Gerhard Adam et al., "Retrofitting YACs for direct DNA transfer into plant cells," The Plant Journal, 1997, vol. 11, pp. 134-1358.
Jessika Adrian et al., "From Decision to Commitment: The Molecular Memory of Flowering," Molecular Plant, Jul. 2009, vol. 2, No. 4, pp. 628-642.
W. Michael Ainley et al., "Regulatable endogenous production of cytokinins up to 'toxic' levels in transgenic plants and plant tissues," Plant Molecular Biology, 1993, vol. 22, pp. 13-23.
Cristina Madeira Alexandre et al., "FLC or not FLC: the other side of vernalization," Journal of Experimental Botany, Apr. 2008, vol. 59, No. 6, pp. 1127-1135.

(Continued)

*Primary Examiner* — Elizabeth F McElwain
(74) *Attorney, Agent, or Firm* — Arent Fox LLP

(57) ABSTRACT

The present invention relates to the identification of monocot FLC sequences, such as wheat FLC sequences, as well as their uses in modulating flowering time, seed development and seed germination.

12 Claims, 4 Drawing Sheets
Specification includes a Sequence Listing.

(56) References Cited

FOREIGN PATENT DOCUMENTS

| | | |
|---|---|---|
| WO | WO-92/13956 A1 | 8/1992 |
| WO | WO-95/06742 A1 | 3/1995 |
| WO | WO-96/06932 A1 | 3/1996 |
| WO | WO-97/13865 A1 | 4/1997 |
| WO | WO-99/53050 A1 | 10/1999 |
| WO | WO-01/12824 A1 | 2/2001 |
| WO | WO-02/00904 A2 | 1/2002 |
| WO | WO-03/008540 A2 | 1/2003 |
| WO | WO-03/052108 A2 | 6/2003 |
| WO | WO-03/076619 A1 | 9/2003 |
| WO | WO-2004/073390 A1 | 9/2004 |
| WO | WO-2005/047505 A2 | 5/2005 |
| WO | WO-2005/052170 A2 | 6/2005 |
| WO | WO-2005/098004 A2 | 10/2005 |
| WO | WO-2006/068432 A1 | 6/2006 |
| WO | WO-2006/074400 A2 | 7/2006 |
| WO | WO-2006/105946 A2 | 10/2006 |
| WO | WO-2007-071789 A1 | 6/2007 |
| WO | WO-2007/098042 A2 | 8/2007 |
| WO | WO-2008/148751 A1 | 12/2008 |
| WO | WO-2009/002150 A1 | 12/2008 |
| WO | WO-2009-030780 A2 | 3/2009 |
| WO | WO-2009/135130 A2 | 11/2009 |
| WO | WO-2010/066740 A1 | 6/2010 |
| WO | WO-2011/112570 A1 | 9/2011 |
| WO | WO-2012/092970 A1 | 7/2012 |
| WO | WO-2012/101118 A1 | 8/2012 |
| WO | WO-2013/023992 A1 | 2/2013 |

OTHER PUBLICATIONS

Stephen F. Altschul et al., "Basic Local Alignment Search Tool," Journal of Molecular Biology, 1990, vol. 215, pp. 403-410.
Stephen F. Altschul et al., "Gapped BLAST and PSI-BLAST: a new generation of protein database search programs," Nucleic Acids Research, 1997, vol. 25, No. 17, pp. 3389-3402.
Richard M. Amasino et al., "The Timing of Flowering[1]," Plant Physiology, Oct. 2010, vol. 154, pp. 516-520.
Ambroella Genome Project, "Amborella Genome Database," http://ambroella.huck.psu.edu, last visited on Nov. 25, 2015, pp. 1-2.
Yong-Qiang An et al., "Conserved Expression of the *Arabidopsis* ACT1 and ACT3 Actin Subclass in Organ Primorida and Mature Pollen," The Plant Cell, Jan. 1996, vol. 8, pp. 15-30.
Jill T. Anderson et al., "Evolutionary genetics of plant adaptation," Trend Genet, Jul. 2011, vol. 27, pp. 258-266.
Rita Arora et al., "MADS-box gene family in rice: genome-wide identification, organization and expression profiling during a reproductive development and stress," BMC Genomics, 2007, vol. 8:242, pp. 1-21.
Orna Avsian-Kretchmer et al., "The Salt-Stress Signal Transduction Pathway That Activates the gpx1 Promoter Is Mediated by Intracellular $H_2O_2$, Different from the Pathway Induced by Extracellular $H_2O_2$," Plant Physiology, Jul. 2004, vol. 135, pp. 1685-1696.
Ricardo Azpiroz-Leehan et al., "T-DNA insertion mutagenesis in *Arabidopsis*: going back and forth," TIG, Apr. 1997, vol. 13, No. 4, pp. 152-156.
Scott R. Baerson et al., "Developmental regulation of an acyl carrier protein gene promoter in vegetative and reproductive tissues," Plant Molecular Biology, 1993, vol. 22, pp. 255-267.
Scott R. Baerson et al., "Identification of domains in an *Arabidopsis* acyl carrier protein gene promoter required for maximal organ-specific expression," Plant Molecular Biology, 1994, vol. 26, pp. 1947-1959.
Kim Baumann et al., "The DNA Binding Site of the Dof Protein NtBBF1 Is Essential for Tissue-Specific and Auxin-Regulated Expression of the rolB Oncogene in Plants," The Plant Cell, Mar. 1999, vol. 11, pp. 323-333.
Annette Becker et al., "The major clades of MADS-box genes and their role in the development and evolution of flowering plants," Molecular Phylogenetics and Evolution, 2003, vol. 29, pp. 464-489.

C.R. Bird et al., "The tomato polygalacuronase gene and ripening-specific expression of transgenic plants," Plant Molecular Biology, 1988, vol. 11, pp. 651-662.
Miguel A. BlÅzquez et al., "Gibberellins Promote Flowering of *Arabidopsis* by Activating the LEAFY Promoter," The Plant Cell, May 1998, vol. 10, pp. 791-800.
Beatrix Blume et al., "Expression of ACC oxidase promoter-GUS fusions in tomato and Nicotiana plumbaginifolia regulated by developmental and environmental stimuli," The Plant Journal, 1997, vol. 12, pp. 731-746.
Aureliano Bombarely et al., "The Sol Genomics Network (solgenomics.net): growing tomatoes using Perl," Nucleic Acids Research, 2011, vol. 39, pp. D1149-D1155.
John L. Bowman et al., "Control of flower development in *Arabidopsis thaliana* by APETALA1 and interacting genes," Development, 1993, pp. 721-743.
Wim Broothaerts et al., "Gene transfer to plants by diverse species of bacteria," Nature, Feb. 2005, vol. 433, pp. 629-633.
Annemarie S. Buchel et al., "Mutation of GT-1 binding sites in the Pr-1A promoter influences the level of inducible gene expression in vivo," Plant Molecular Biology, 1999, vol. 40, pp. 387-396.
Peter Kamp Busk et al., "Regulatory elements in vivo in the promoter of the abscisic acid responsive gene rab17 from maize," The Plant Journal, 1997, vol. 11, pp. 1285-1295.
Judy Callis et al., "Introns increase gene expression in cultured maize cells," Genes and Development, 1987, pp. 1183-1200.
Guillermo H. Chardon et al., "Functional analysis of the *Arabidopsis thaliana* SBP-box gene SPL3: a novel gene involved in the floral transition," The Plant Journal, 1997, vol. 12, pp. 367-377.
James C. Carrington et al., "Cap-Independent Enhancement of Translation by a Plant Potyvirus 5' Nontranslated Region," Journal of Virology, Apr. 12, 1990, pp. 1590-1597.
Barry Causier et al., "Tracing the Evolution of the Floral Homeotic B- and C-Function Genes through Genome Synteny," Mol. Biol. Evol., 2010, vol. 27, pp. 2651-2664.
Nicole Chaubet et al., "Nucleotide sequences of two corn histone H3 genes. Genomic organization of the corn histone H3 and H4 genes," Plant Molecular Biology, 1986, vol. 6, pp. 253-263.
Nicole Chaubet-Gigot et al., "Tissue-dependent enhancement of transgene expression by introns of replacement histone H3 genes of *Arabidopsis*," Plant Molecular Biology, 2001, vol. 45, pp. 17-20.
Wenqlong Chen et al., "The promoter of $H_2O_2$-inducible, *Arabidopsis* glutathione S-transferase gene contains closely linked OBF- and OBP1-binding sites," The Plant Journal, 1996, vol. 10, pp. 955-966.
George C.K. Chiang et al., "Major flowering time gene, Flowering Locus C, regulates seed germination in *Arabidopsis thaliana*," PNAS, Jul. 1999, vol. 106, No. 28, pp. 11661-11666.
Kyuha Choi et al., "The FRIGIDA Complex Activates Transcription of FLC, a Strong Flowering Repressor in *Arabidopsis*, by Recruiting Chromatin Modification Factors," The Plant Cell, Jan. 2011, vol. 23, pp. 289-303.
P. Chouard, "Vernalization and Its Relations to Dormancy," Annu. Rev. Plant. Physiol, 1960, vol. 11, pp. 191-238.
Alan H. Christensen et al., "Maize polyubiquitin genes: structure, thermal, perturbation of expression and transcript splicing, and promoter activity following transfer to protoplasts by electroporation," Plant Molecular Biology, 1992, vol. 18, pp. 675-689.
Paul Christou, "Rice Transformation: bombardment," Plant Molecular Biology, 1997, vol. 35, pp. 197-203.
Maureen Clancy et al., "Splicing of the Maize, sh1 First Intron Is Essential for Enhancement of Gene Expression, and a T-Rich Motif Increases Expression without Affecting Splicing," Plant Physiology, Oct. 2002, vol. 130, pp. 918-929.
James Cockram et al., "Control of flowering time in temperate cereals: genes, domestication, and sustainable productivity," Journal of Experimental Botany, 2007, vol. 58, No. 6, pp. 1231-1244.
Joseph Colasanti et al., "Mechanisms of Floral Induction in Grasses: Something Borrowed, Something New," Plant Physiology, Jan. 2009, vol. 149, pp. 56-62.

(56) References Cited

OTHER PUBLICATIONS

Udo Conrad et al., "Potatoes expressing single-domain antibodies in their plastids inhibit a starch-branching enzyme and produce high-amylose starch," www.nature.com/naturebiotechnology, Jan. 2003, vol. 21, pp. 35-36.
B. Sylvia De Pater et al., "The promoter of the rice gene GOS2 is active in various different monocot tissues and binds rice nuclear factor ASF-1," The Plant Journal, 1992, vol. 2, 837-844.
Lieven De Veylder et al., "Herbicide Safener-Inducible Gene Expression in *Arabidopsis thaliana*," Plant Cell Physiol. 1997, vol. 38, pp. 568-577.
Weiwei Deng et al., "Flowering Locus C (FLC) regulates development pathways throughout the life cycle of *Arabidopsis*," PNAS, Apr. 2011, vol. 108, No. 16, pp. 6680-6685.
A. Depicker, "Nopaline Synthase: Transcript Mapping and DNA Sequence," Journal of Molecular and Applied Genetics, 1982, pp. 561-573.
A. J. Enright et al, "An efficient algorithm for large-scale detection of protein families," Nucleic Acids Research, 2002, vol. 30, No. 7, pp. 1575-1584.
Michael Ficker et al., "A promoter directing high level expression in pistils of transgenic plants," Plant Molecular Biology, 1997, vol. 35, pp. 425-431.
Susheng Gan et al., "Inhibition of Leaf Senescence by Autoregulated production of Cytokinin," Science, Dec. 1995, vol. 20, pp. 1986-1988.
C. Gatz, "Chemical Control of Gene Expression," Annu. Rev. Plant Physiol. Plant Mol. Biol. 1997, vol. 48, pp. 89-108.
David M. Goodstein et al., "Phytozome: a comparative platform for green plant genomics," Nucleic Acid Research, 2012, vol. 40, pp. D1178-D1186.
Aaron G. Greenup et al., "ODDSOC2 Is a MADS Box Floral Repressor That is Down-Regulated by Vernalization in Temperate Cereals," Plant Physiology, Jul. 2010, vol. 153, pp. 1062-1073.
Felix D. Guerrero et al., "Promoted sequences from a maize pollen-specific gene direct tissue-specific transcription in tobacco," Mol Gen Genet, 1990, vol. 224, pp. 161-168.
Arturo Guevara-Garcia et al., "A 42 bp fragment of the pmas1' promoter containing an ocs-like element confers a developmental, wound- and chemically inducible expression pattern," Plant Molecular Biology, 1998, vol. 38, pp. 743-753.
Stèphane Guindon et al., "New Algorithms and Methods to Estimate Maximum-Likelihood Phylogenies: Assessing the Performance of PhyML 3.0," Syst. Biol., 2010, vol. 59, pp. 307-321.
Matthew A. Hannah et al., "A Global Survey of Gene Regulation during Cold Acclimation in *Arabidopsis thaliana*," PLoS Genetics, Aug. 2005, vol. 1, pp. 0179-0196.
G. Hansen et al., "Wound-inducible and organ-specific expression of ORF13 from Agrobacterium rhizogenes 8196 T-DNA in transgenic tobacco plants," Mol Gen Genet, 1997, vol. 254, pp. 337-343.
Mark H. Harpster et al., "Relative strengths of the 35S cauliflower mosaic virus, 1', 2', and nopaline synthase promoters in transformed tobacco sugarbeet and oilseed rape callus tissue," Mol Gen Genet, 1988, vol. 212, pp. 182-190.
Chris Helliwell et al., "Constructs and methods for high-throughput gene silencing in plants," Science Direct, Methods, 2003, vol. 30, pp. 289-295.
Megan N. Hemming et al., "Make hay when the sun shines: The role of MADS-box genes in temperature-dependant seasonal flowering responses," Plant Science, 2011, vol. 180, pp. 447-453.
Shin-Yong Hong et al., "Exploring valid reference genes for gene expression studies in Brachypodium distachyon by real-time PCR," BMC Plant Biology, 2008, vol. 8, pp. 1-11.
Richard L. Hudspeth et al., "Structure and expression of the maize gene encoding the phosphoenolpyruvate carboxylase isozyme involved in $C_4$ photosynthesis," Plant Molecular Biology, 1989, vol. 12, pp. 579-589.
The International Brachypodium Intiative, "Genome Sequencing and analysis of the model grass *Brachypodium distachyon*," Nature, Feb. 2010, vol. 463, pp. 763-768.

Sharmin Jahan et al., "Expression of Transgene under Stress Inducible Promoter for producing Salt Tolerant rice," Department of Biochemistry and Molecular Biology, University of Dhaka, 1 page.
Jose A. Jarillo et al., "Timing is everything in plant development. The central role of floral repressors," Plant Science, 2011, vol. 181, pp. 364-378.
Yuannian Jiao et al., "A genome triplication associated with early diversification of the core eudicots," Genome Biology, 2012, vol. 13, pp. 1-14.
Urban Johanson et al., "Molecular Analysis of FRIGIDA, a Major Determinant of Natural Variation in *Arabidopsis* Flowering Time," Science, Oct. 2000, vol. 290, pp. 344-347.
Maliyakal E. John et al., "Gene expression in cotton (*Gossypium hirsutum* L.) fiber: Cloning of the mRNAs," Proc. Natl. Acad. Sci. USA, Jul. 1992, vol. 89, pp. 5769-5773.
Thomas Kaiser et al., "Cis-acting elements of the CHS1 gene from white mustard controlling promoter activity and spatial patterns of expression," Plant Molecular Biology, 1995, vol. 28, pp. 231-243.
Ndjido A. Kane et al., "TaVRT-2, a Member of the StMADS-11 Clade of Flowering Repressors, Is Regulated by Vernalization and Photoperiod in Wheat," Plant Physiology, Aug. 2005, vol. 138, pp. 2354-2363.
Kazutaka Katoh et al., "Improved accuracy of multiple ncRNA alignment by incorporating structural information into a MAFFT-based framework," BMC Bioinformatics, Apr. 2008, vol. 9, pp. 1-13.
Kerstin Kaufmann et al., "Target Genes of the MADS Transcription Factor SEPALLATA3: Integration of Development and Hormonal Pathways in the *Arabidopsis* Flower," PLoS Biology, Apr. 2009, vol. 7, No. 4, pp. 854-875.
Michael Keil et al., "Both wound-inducible and tuber-specific expression are mediated by the promoter of a single member of the potato proteinase inhibitor II gene family," The EMBO Journal, 1989, vol. 8, No. 5, pp. 1323-1330.
Zsolt Kelemen et al., "Transformation vector based on promoter and intron sequences of a replacement histone H3 gene. A tool for high, constitutive gene expression in plants," Transgenic Research, 2002, vol. 11, pp. 69-72.
Beat Keller et al., "Glycine-rich cell wall proteins in bean: gene structure and association of the protein with the vascular system," The EMBO Journal, 1988, vol. 7, No. 12, pp. 3625-3633.
Beat Keller et al., "Specific expression of a novel cell wall hydroxyproline-rich glycoprotein gene in lateral root initiation," Genes & Development, 1989, vol. 3, pp. 1639-1646.
Dong-Hwan Kim et al., "The Plant Homeo Domain finger protein, VIN3-LIKE 2, is necessary for photoperiod-mediated epigenetic regulation of the floral repressor, MAF5," PNAS, Sep. 2010, vol. 107, No. 39, pp. 17029-17034.
Song Lim Kim et al., "OsMADS51 Is a Short-Day Flowering Promoter That Functions Upstream of Ehd1, OsMADS514, and Hd3a," Plant Physiology, Dec. 2007, vol. 145, pp. 1484-1494.
Dong-Hwan Kim et al., "Vernalization: Winter and the Timing of Flowering in Plants," Annu. Rev. Cell. Dev. Biol. 2009, vol. 25, pp. 277-279.
Harry Klee et al., "Agrobacterium-Mediated Plant Transformation and Its Further Applications to Plant Biology," Ann. Rev. Plant Physiol. 1987, vol. 38, pp. 467-486.
T. M. Klein et al., "High-velocity microprojectiles for delivering nucleic acid into living cells," Nature, May 1987, vol. 327, pp. 70-73.
Cris Kuhlemeier et al., "The Pea rbcS-3A Promoter Mediates Light Responsiveness but not Organ Specificity," The Plant Cell, Apr. 1989, vol. 1, pp. 471-478.
Jeong Hwan Lee et al., "Role of SVP in the control of flowering time by ambient temperature in *Arabidopsis*," Genes & Development, 2007, vol. 21, pp. 397-402.
Shinyoung Lee et al., "Further Characterization of a Rice AGL12 Group MADS-Box Gene, OsMADS26," Plant Physiology, May 2008, vol. 147, pp. 156-168.
Xin Li et al., "A fast neutron deletion mutagenesis-based reverse genetics system for plants," The Plant Journal, 2001, vol. 27, pp. 235-242.

(56) References Cited

OTHER PUBLICATIONS

Zhan-Bin Liu et al., "A G-Box-Binding Protein from Soybean Binds to the E1 Auxin-Response Element in the Soybean GH3 Promoter and Contains a Proline-Rich Repression domain," Plant Physiol. 1997, vol. 115, pp. 397-407.
Therese Mandel et al., "Definition of constitutive gene expression in plants: the translation initiation factor 4A gene as a model," Plant Molecular Biology, 1995, vol. 29, 995-1004.
John M. Manners et al., "The promoter of the plant defensin gene PDF1.2 from *Arabidopsis* is systemically activated by fungal pathogens and responds to methyl jasmonate but not to salicylic acid," Plant Molecular Biology, 1998, vol. 38, pp. 1071-1080.
Desmond Mascarenhas et al. "Intron-mediated enhancement of heterologous gene expression in maize," Plant Molecular Biology, 1990, vol. 15, pp. 913-920.
Caries Masgrau et al., "Inducible over expression of oat arginine decarboxylase in transgenic tobacco plants," The Plant Journal, 1997, vol. 11, pp. 465-473.
Claire M. McCallum et al., "Targeted screening for induced mutations," Nature Biotechnology, Apr. 2000, vol. 18, pp. 455-457.
David McElroy et al., "Isolation of an Efficient Actin Promoter for Use in Rise Transformation," The Plant Cell, Feb. 1990, vol. 2, pp. 163-171.
N. McKenzie et al., "Tissue-culture enhanced transposition of the maize transposable element Dissociation in *Brassica oleracea* var. '*Italica*'," Theor Appl Genet, 2002, vol. 105, pp. 23-33.
Rainer Melzer et al., "The naked and the dead: The ABCs of gymnosperm reproduction and the origin of the angiosperm flower," Seminars and Cell & Developmental Biology, 2010, vol. 21, pp. 118-128.
Scott D. Michaels et al., "Flowering Locus C Encodes a Novel MADS Domain Protein That Acts as a Repressor of Flowering," The Plant Cell, May 1999, vol. 11, pp. 949-956.
Scott D. Michaels et al., "Loss of Flowering Locus Activity Eliminates the Late-Flowering Phenotype of FRIGIDA and Autonomous Pathway Mutations but Not Responsiveness to Vernalization," The Plant Cell, Apr. 2001, vol. 13, pp. 935-941.
Robert Morbitzer et al., "Regulation of selected genome loci using de novo-engineered transcription activator-like effector (TALE)-type transcription factors," PNAS, Dec. 2010, vol. 107, No. 50, pp. 21617-21622.
Matthew J. Moscou et al., "A Simple Cipher Governs DNA Recognition by TAL Effectors," Science, Dec. 2009, vol. 326, p. 1501.
Gyoungju Nah et al., "Tandem duplication of the FLC Locus and the origin of a new gene in *Arabidopsis* related species and their functional implications in allopolyploids," New Phytologist, 2010, vol. 186, pp. 228-238.
Saul B. Needleman et al., "A General Method Applicable to the Search for Similarities in the Amino Acid Sequence of Two Proteins," J. Mol. Boil. 1970, vol. 48, pp. 443-453.
Joan. T. Odell et al., "Seed-Specific Gene Activation Mediated by the Cre/lox Site-Specific Recombination System," Plant Physiol. 1994, vol. 106, pp. 447-458.
Stephan Ohl et al., "Functional Properties of a Phenylalanine Ammonia-Lyase Promoter from *Arabidopsis*," The Plant Cell, Sep. 1990, vol. 2, pp. 837-848.
Ralph Panstruga et al., "Testing the efficiency of dsRNAi constructs in vivo: A transient expression assay based on two fluorescent proteins," Molecular Biology Reports, 2003, vol. 30, pp. 135-140.
Wojciech P. Pawlowski et al., "Transgene Inheritance in Plants Genetically Engineered by Microprojectile Bombardment," Molecular Biotechnology, 1996, vol. 6, pp. 17-30.
Soraya Pelaz et al., "B and C floral organ identity functions require SEPALLATA MADS-box genes," Nature, May 2000, vol. 405, pp. 200-203.
Johan Peleman et al., "Structure and expression analyses of the S-adenosylmethionine synthetase gene family in *Arabidopsis thaliana*," pp. 359-369.
David Posada, "jModelTest: Phylogenetic Model Averaging," Mol. Biol. Evol. 2008, vol. 25, pp. 1253-1256.

Sebastian Proost et al., "i-ADHoRe 3.0—fast and sensitive detection of genomic homology in extremely large data sets," Nucleic Acids Research, 2012, vol. 40, No. 2, pp. 1-11.
Oliver J. Ratcliffe et al., "Regulation of Flowering in *Arabidopsis* by an FLC Homologue," Plant Physiol. 2001, pp. 122-132.
T.S. Ream et al., "The Molecular Basis of Vernalization in Different Plant Groups," Cold Spring Harbor Sympsia on Quantitative Biology, 2012, pp. 105-115.
Patrick A. Reeves et al., "Evolutionary Conservation of the Flowering Locus C-Mediated Vernalization Response: Evidence from the Sugar Beat (*Beta vulgaris*)," Genetics, May 2007, vol. 176, pp. 295-307.
Leonore Reiser et al., "The BELL1 Gene Encodes a Homeodomain Protein Involved in Pattern Formation," Cell, Dec. 1995, vol. 83, pp. 735-742.
Peter Rice et al., "EMBOSS: The European Molecular Biology Open Software Suite," TIG, Jun. 2000, vol. 16, No. 6, pp. 276-277.
Philippe Rigault et al., "A White Spruce Gene Catalog for Conifer Genome Analyses," Plant Physiology, Sep. 2011, vol. 157, pp. 14-28.
Jennifer A. Rinehart et al., "Tissue-Specific and Developmental Regulation of Cotton Gene FbL2A," Plant Physiol. 1996, vol. 112, pp. 1331-1341.
Timothy A. Rinehart et al., "Comparative analysis of non-random DNA repair following Ac Transposon excision in maize and *Arabidopsis*," The Plant Journal, 1997, vol. 12, pp. 1419-1427.
Christoph Ringli et al., "Specific Interaction of the tomato bZIP transcription factor VSF-1 with a non-palindromic DNA sequence that controls vascular gene expression," Plant Molecular Biology, 1998, vol. 37, pp. 977-988.
Fredrik Ronquist et al., "MrBayes 3: Bayesian phylogenetic inference under mixed models," Bioinformatics, 2003, vol. 19, No. 12, pp. 1572-1574.
Szabolcs Rudnoy et al., "FLC-like factors in wheat (cv. Mv15) and *Conyza* sp.," Plant Physiology, 2002, vol. 46, pp. 45-46.
Tatsuya Sakai et al., "Analysis of the Promoter of the Auxin-Inducible Gene, parC, of Tobacco," Plant Cell Physiol. 1996, vol. 37, pp. 906-913.
Anton R. SchÄffner et al., "Maize rbcS Promoter Activity Depends on Sequence Elements Not Found in Dicot rbcS Promoters," The Plant Cell, Sep. 1991, vol. 3, pp. 997-1012.
M. Eric Schranz et al., "Characterization and Effects of the Replicated Flowering Time Gene FLC in *Brassica rapa*," Genetics, Nov. 2002, vol. 162, pp. 1457-1468.
Christopher J. Schwartz et al., "Natural Variation of Flowering Time and Vernalization Responsiveness in Brachypodium distachyon," Bioenerg. Res., 2010, vol. 3, pp. 38-46.
Iain Searle et al., "The transcription factor FLC confers a flowering response to vernalization by repressing meristem competence and systemic signaling in *Arabidopsis*," Genes & Development, 2006, vol. 20, pp. 898-912.
Hongyan Shan et al., "Evolution of Plant MADS Box Transcription Factors: Evidence for Shifts in Selection Associated with Early Angiosperm Diversification and Concerted Gene Duplications," Mol. Biol. Evol., 2009, vol. 26, pp. 2229-2244.
Jen Sheen, "$Ca^{2+}$-Dependent Protein Kinases and Stress Signal Transduction in Plants," Science Magazine, May 27, 2000, pp. 1-5.
Lifang Shi et al., "Gibberellin and abscisic acid regulate GAST1 expression at the level of transcription," Plant Molecular Biology, 1998, vol. 38, pp. 1053-1060.
Barbara Siebertz et al., "cis-Analysis of the Wound-Inducible Promoter wun1 in Transgenic Tobacco Plants and Histochemical Localization of its Expression," The Plant Cell, Oct. 1989, vol. 1, pp. 961-968.
Neil A. Smith et al., "Total Silencing by intronspliced hairpin RNAs," Nature, Sep. 2000, vol. 407, pp. 319-320.
Claudia Stange et al., "Phosphorylation of nuclear proteins directs binding to salicylic acid-responsive elements," The Plant Journal, 1997, vol. 11, pp. 1315-1324.
Wolfgang R. Streit et al., "A Biotin-Regulated Locus, bios, in a Possible Survival Operon of Rhizobium meliloti," MPMI, 1997, vol. 10, No. 7, pp. 933-937.

(56) References Cited

OTHER PUBLICATIONS

Qinghua Sun et al., "Identification of a new 130 bp cis-acting element in the TsVP1 promoter involved in the salt stress response from Thellungiella halophila," BMC Plant Biology, 2010, vol. 10, pp. 1-12.
Million Tadege et al., "Reciprocal control of flowering time by OsSOC1 in transgenic *Arabidopsis* and by FLC in transgenic rice," Plant Biotechnology Journal, 2003, vol. 1, pp. 361-369.
Shigeo Takumi et al., "Variation in transformation frequencies among six common wheat cultivars through particle bombardment of scutellar tissues," Genes Genet. Syst., 1997, vol. 72, pp. 63-69.
Haibao Tang et al., "Angiosperm genome comparisons reveal early polyploidy in the monocot lineage," PNAS, Jan. 2010, vol. 107, No. 1, pp. 472-477.
The Potato Genome Sequencing Consortium, "Genome sequence and analysis of the tuber crop potato," Nature, Jul. 2011, vol. 475, pp. 189-197.
The Tomato Genome Consortium, "The tomato genome sequence provides insights into fleshy fruit evolution," Nature, May 2012, vol. 485, pp. 635-641.
Julie D. Thompson et al., "CLUSTAL W: improving the sensitivity of progressive multiple sequence alignment through sequence weighting, position-specific gap penalties and weight matrix choice," Nucleic Acid Research, 1994, vol. 22, No. 22, pp. 4673-4680.
Michiel Van Bel et al., "Dissecting Plant Genomes with the PLAZA Comparative Genomics Platform," Plant Physiology, Feb. 2012, vol. 158, pp. 590-600.
Dianne A.M. Van Der Kop et al., "Selection of *Arabidopsis* mutants overexpressing genes driven by the promoter of an auxin-inducible glutathione S-transferase gene," Plant Molecular Biology, 1999, vol. 39, pp. 979-990.
Dries Vekemans et al., "Gamma Paleohexaploidy in the Stem Lineage of Core Eudicots: Significance for MADS-Box Gene and Species Diversification," Mol. Biol. Evol. 2012, pp. 1-14.
Bertrand Verdaguer et al., "Isolation and expression in transgenic tobacco and rice plants, of the cassava vein mosaic virus (CVMV) promoter," Plant Molecular Biology, 1996, vol. 31, pp. 1129-1139.
Amelie S. Veron et al., "Evidence of Interaction Network Evolution by Whole-Genome Duplications: A Case Study in MADS-Box Proteins," Mol. Biol. Evol., 2007, vol. 24, pp. 670-678.
Yan Wang et al., "The genome of the mesopolyploid crop species *Brassica rapa*," Nature Genetics, Oct. 2011, vol. 43, No. 10, pp. 1035-1040.
Peter M. Waterhouse et al., "Exploring Plant Genomes by RNA-Induced Gene Silencing," Nature Reviews, Jan. 2003, vol. 4, pp. 29-38.
Ruth L. Willmott et al., "DNase1 footprints suggest the involvement of at least three types of transcription factors in the regulation of α-Amy2/A by gibberellin," Plant Molecular Biology, 1998, vol. 38, pp. 817-825.
Mark O. Winfield et al., "Cold- and light-induced changes in the transcriptome of wheat leading to phase transition from vegetative to reproductive growth," BMC Plant Biology, 2009, vol. 9, pp. 1-14.
Kazuko Yamaguchi-Shinozaki et al., "A Novel cis-Acting Element in an *Arabidopsis* Gene is Involved in Responsiveness to Drought, Low-Temperature, or High-Salt Stress," The Plant Cell, Feb. 1994, vol. 6, pp. 251-264.
L. Yan et al., "Positional cloning of the wheat vernalization gene VRN1," PNAS, May 2003, vol. 100, No. 10, pp. 6263-6268.
Liuling Yan et al., "The Wheat VRN2 Gene Is a Flowering Repressor Down-Regulated by Vernalization," Science, Mar. 2004, vol. 303, pp. 1640-1644.
L. Yan et al., "The wheat and barley vernalization gene VRN3 is an orthologue of FT," PNAS, Dec. 2006, vol. 103, No. 51, pp. 19581-19586.
Tao Zhao et al., "Characterization and expression of 42 MADS-box genes in wheat (*Triticum aestivum* L.)," Mol Gen Genomics, 2006, vol. 276, pp. 334-350.

Jianru Zuo et al., "An estrogen receptor-based transactivator XVE mediates highly inducible gene expression in transgenic plants," The Plant Journal, 2000, vol. 24, pp. 265-273.
International Search Report issued in International Patent Application No. PCT/EP2014/063985 dated Apr. 14, 2014.
GenBank Accession No. AB007505.1, "Triticum aestivum TaMADS#12 mRNA for MADS box transcription factor, complete cds," AB007505, updated Nov. 28, 2008.
GenBank Accession No. BRADI2G59120.2, "Brachypodium distachyon," BRADI2G59120, updated Aug. 23, 2013.
GenBank Accession No. BRADI2G59190.1, "Brachypodium distachyon," BDI010800, updated Jun. 3, 2013.
GenBank Accession No. BRADI3G41300.1, "Brachypodium distachyon," BDI010859, updated Jun. 3, 2013.
GenBank Accession No. CA295053.1, "SCQGLV1018F06.g LV1 Saccharum hybrid cultivar (mixed) cDNA clone SCQGLV1018F065- mRNA sequence," CA295053, late updated Feb. 1, 2011.
GenBank Accession No. CK929266.1, "p5rmgc_000520 Normalized Magnaporthe grisea cDNA pGEM-T Easy Library Magnaporthe grisea cDNA clone p5rmgc_000520, mRNA sequence," CK919266, last updated Apr. 22, 2004.
GenBank Accession No. DQ512357.1, "Triticum aestivum MADS-box transcription factor TaAGL41 (AGL41) mRNA, complete cds," DQ512357, last updated Sep. 1, 2006.
GenBank Accession No. DQ512358.1, "Triticum aestivum MADS-box transcription factor TaAGL42 (AGL42) mRNA, complete cds," DQ512358, last updated Sep. 1, 2006.
GenBank Accession No. DQ512365.1, "Triticum aestivum MADS-box transcription factor TaAGL22 (AGL22) mRNA, complete cds," DQ512365, last updated Sep. 1, 2006.
GenBank Accession No. DQ512366.1, "Triticum aestivum MADS-box transcription factor TaAGL33 (AGL33) mRNA, complete cds," DQ512366, last updated Sep. 1, 2006.
GenBank Accession No. DQ512367.1,"Triticum aestivum MADS-box transcription factor TaAGL12 (AGL12) mRNA, partial cds," DQ512367, last updated Sep. 1, 2006.
GenBank Accession No. ES295415.1, "_12W_G08 Bermudagrass Normalized cDNA Library Cynodon dactylon cDNA 5-, mRNA sequence," ES295415, last updated May 6, 2011.
GenBank Accession No. FL658504.1, "Embrapa_Musa_ABB_ NonStressed_Cachaco_NS61TF Embrapa_Musa_Cachaco_ABB_ Nonstressed Musa ABB Group cDNA, mRNA sequence," ES295415, last updated Aug. 30, 2000.
GenBank Accession No. FL799640.1, "CCGG2601.b1 CCGG Panicum virgatum late flowering buds + seed development (H) Panicum virgatum cDNA clone CCGG2601 5-, mRNA sequence," FL799640, last updated Sep. 5, 2008.
GenBank Accession No. FL926484.1, "CCGP2176.b1 CCGP Panicum virgatum root (L) Panicum virgatum cDNA clone CCGP2176 5-, mRNA sequence," FL926484, last updated Sep. 5, 2008.
GenBank Accession No. AEL87842.1, "type I, MADS-box protein [Triticum aestivum]," AEL87842, last updated Oct. 19, 2011.
GenBank Accession No. GR360557.1, "CCOY4011.b1 CCOY Avena barbata root, pooled from different levels of rain and nitrogen (L) Avena barbata cDNA CCOY4011 5-, mRNA sequence," GR360557, last updated Jun. 19, 2009.
GenBank Accession No. DAA49014.1, "TPA: putative MADS-box transcription factor family protein [*Zea mays*]," DAA49014, last updated Oct. 24, 2013.
GenBank Accession No. DAA48217.1, TPA: putative MADS-box transcription factor family protein [*Zea mays*], DAA48217, last updated Oct. 24, 2013.
GenBank Accession No. DAA53550.1, "TPA: putative MADS-box transcription factor family protein, partial [*Zea mays*]," DAA53550, last updated Oct. 24, 2013.
GenBank Accession No. HC084629.1, "Sequence 3 from Patent EP2119787," HC084629, last updated Nov. 25, 2009.
GenBank Accession No. HM130525.1, "*Hordeum vulgare* subsp. *vulgare* cultivar lgri ODDSOC1 (ODDSOC1) mRNA, complete cds," HM130525, last updated Jun. 26, 2010.
GenBank Accession No. HO164248.1, "BG04085A2D07.fl BG04— primary and normalized libraries Dactylis glomerata cDNA, mRNA sequence," H0164248, last updated May 17, 2011.

(56) References Cited

OTHER PUBLICATIONS

GenBank Accession No. JN248615.1, "Triticum aestivum type I MADS-box protein (MADS2) mRNA, complete cds," JN248615, last updated Aug. 13, 2011.
GenBank Accession No. JC625108.1, "Sequence from 10889 from Patent EP2761003," JC625108, last updated Sep. 11, 2014.
GenBank Accession No. 8079807, "SORBIDRAFT_03g044170 hypothetical protein [*Sorghum bicolor* (sorghum) ]," SORBIDRAFT_03g044170, last updated Nov. 1, 2014.
GenBank Accession No. 80680949, "SORBIDRAFT_07g026180 hypothetical protein [*Sorghum bicolor* (sorghum)]," SORBIDRAFT_07g026180, last updated Nov. 1, 2014.
GenBank Accession No. KQL02654.1, "hypothetical protein SETIT_014540mg [Setaria italic]," KQL02654, last updated Oct. 30, 2015.
GenBank Accession No. U3994.2, "*Arabidopsis thaliana* homeobox protein (BEL1) mRNA, complete cds," U39944, last updated Feb. 4, 2003.

* cited by examiner

METHODS AND MEANS FOR MODULATING FLOWERING TIME IN MONOCOT PLANTS

CROSS-REFERENCE TO RELATED APPLICATION

This application is a 35 U.S.C. 371 National Phase of PCT Application Ser. No. PCT/EP2014/063985 filed Jul. 1, 2014, which claims priority to European Patent Application No. 13174566.3 filed Jul. 1, 2013, the disclosure of which is hereby incorporated in their entirety by reference.

FIELD OF THE INVENTION

The present invention relates generally to the field of plant molecular biology and concerns a method for modulating flowering time. More specifically, the present invention concerns a method for accelerating or delaying flowering time, comprising altering expression and/or activity of a FLOWERING LOCUS C (FLC) gene and/or protein in monocot plants. The invention also provides chimeric genes, nucleic acids encoding such monocot FLC proteins.

BACKGROUND OF THE INVENTION

Flowering plants have evolved an enormous complexity and diversity in the developmental transition from vegetative to reproductive growth. Environmental and internal cues are integrated in a quantitative flowering response that varies between species and even between ecotypes (Anderson et al (2011) Trends Genet. 27: 258). Plants growing in temperate climates use photoperiod or day-length, in addition to vernalization or low temperatures to sense the passing of winter into optimal reproductive environmental conditions (Amasino et al (2010) Plant Physiol 154: 516). The elaboration of reproductive development in flowering plants is associated with the origin and diversification of developmental control genes, most prominently members of the MADS-box transcription factor family. The origin of several subfamilies of MADS-box genes with crucial roles in the floral transition remains shrouded in mystery, in that they appear to be present in just flowering plants or in specific lineages of flowering plants.

One lineage of MADS-box genes with a highly enigmatic origin is the clade of FLOWERING LOCUS C (FLC) genes. In the model plant *Arabidopsis thaliana*, FLC is a central repressor of the floral transition (Michaels & Amasino (1999) Plant Cell 11, 949), where it inhibits flowering by directly repressing the activity of central flowering promoters, namely SUPPRESSOR OF OVEREXPRESSION OF CONSTANS (SOC1), FLOWERING LOCUS D (FD) and FLOWERING LOCUS T (FT) (Anderson et al (2011) (supra); Amasino et al (2010) (supra); Michaels & Amasino (1999) (supra); Adrian et al (2009) Mol. Plant. 2, 628; Searle et al (2006) Genes. Dev. 20, 898). Vernalization alleviates this repression by negatively regulating FLC expression through epigenetic modifications of the chromatin structure at the FLC locus (Amasino et al (2010) (supra); Adrian et al (2009) (supra). FLC also transduces temperature signals during seed germination Chiang et al (2009) Proc Natl Acad Sci USA 106:11661). FLC has five closely related paralogs in the *Arabidopsis thaliana* genome, some of which also act as floral repressors (Ratcliffe et al (2001) Plant Physiol. 126, 122; Ratcliffe et al (2003) Plant Cell 15, 1159; Kim & Sung (2010) Proc. Natl. Acad. Sci. USA. 107, 17029). These paralogs arose in evolution through sequential tandem and genome duplications within the order Brassicales (Schranz et al (2002) Genetics, 162, 1457; Nah & Chen (2010) New Phytol. 186, 228). Tandem duplications of FLC-like genes appear not uncommon, as they have also been reported in other *Arabidopsis* species (Nah & Chen (2010) (supra). Outside of Brassicales FLC-like genes have been identified in more distantly related core eudicot species. For instance in sugar beet (*Beta vulgaris*), a crop with a strong vernalization requirement, FLC expression also responds to vernalization. This suggests that FLC's role in cold-induced flowering is conserved in core eudicots (Reeves et al (2007) Genetics 176, 295). FLC homologs, however, have not been identified outside the core eudicots and the phylogenetic position of this subfamily in the larger MADS-box gene phylogeny, and therefore its evolutionary origin, is uncertain. It has therefore been postulated that FLC genes do not exist in monocots and current models for the regulation of flowering time in cereals do not include FLC (Alexandre & Hennig (2008) J. Exp. Bot. 59, 1127; Colasanti & Coneva (2009) Plant Physiol. 149: 56-62, Jarillo & Pineiro (2011) Plant Sci. 181: 364-378; Yan et al (2003) PNAS 100:6263-6268; Yan et al (2004) Science 303:1640-1644; Yan et al (2006) PNAS 103:19581-19586; Cockram et al (2007) J Exp Bot 58:1231-1244). Historically, vernalization has been first described and extensively studied in temperate monocot crops, like winter varieties of wheat and barley (Chouard (1960) Annu. Rev. Plant Physiol. 11, 191). This illustrates the agronomic importance of this trait. To significantly accelerate flowering and subsequent seed set, winter cereals require a sufficiently long period of cold. In contrast to *Arabidopsis*, however, the currently known elements of their vernalization response only involve other members of the MADS-box gene family as well as other genes (Chouard (1960) (supra); Alexandre & Hennig (2008), supra; Kim et al (2009) Annu. Rev. Cell Dev. Biol. 25, 277). Therefore, it has previously been suggested that the vernalization response in temperate cereals and eudicots has evolved independently (Alexandre & Hennig (2008) (supra); Kim et al (2009) (supra); Hemming & Trevaskis (2011) Plant Sci. 180, 447; Ream et al. (2013) Cold Spring Harb. Symp. Quant. Biol. doi:10.1101/sqb.2013.77.014449) and, hence, do not commonly involve FLC.

FLC-like genes are not the only subfamily of MADS-box genes with an enigmatic origin. While members of the *SQUAMOSA* (SQUA) and SEPALLATA (SEP) subfamilies have been identified in all major flowering plant lineages, no gymnosperm representatives have so far been found despite the availability of extensive transcriptome data and targeted cloning efforts Rigault et al. (2011) Plant Physiol. 157:14-28; Melzer et al (2010) Semin. Cell Dev Biol. 21:118-128. In angiosperms, rounds of polyploidization (whole-genome duplications) probably generated many of the observed gene duplications in the SQUA and SEP subfamilies (Veron et al. (2007), Mol. Biol. Evol. 24:670-678; Shan et al (2009) Mol. Biol. Evol. 26:2229-2244; Jiao et al (2012) Genome Biol. 13:R3; Vekemans et al. (2012) Mol. Biol. Evol. doi: 10.1093/molbev/mss183). Members of the SQUA subfamily are generally positive regulators of the floral transition since they control the formation of inflorescence and floral meristems (Bowman et al (1993) Development, 119(3):721-743). SEP genes act as key regulators of floral organ specification, and in a partially redundant manner with SQUA-like genes in floral meristem specification (Pelaz et al (2000) Nature 405:200-203; Kaufmann et al. (2009) PLoS Biol. 7, e1000090).

Greenup e al. ((2010) Plant Physiol. 153, 1062) describes the identification of a vernalization responsive barley MADS box floral repressor protein.

Winfield et al ((2009) BMC Plant Biol. 9, 55) describes cold- and light-induced changes in the transcriptome of wheat leading to phase transition from vegetative to reproductive growth.

WO2006/068432 discloses to flowering-time and/or stem elongation regulator isolated from rice, a DNA construct containing the regulator, a transgenic plant, a part thereof, and plant cell transformed with the DNA construct, and methods to control flowering-time and/or stem elongation using the regulator.

Clarifying the origin of the enigmatic FLC subfamily, but also that of SEP and SQUA can greatly contribute to our understanding of the evolution of flowering plants. Here, we combined genomic synteny-based approaches and phylogeny reconstruction to understand the evolutionary history of these MADS-box gene subfamilies. This allowed us to identify FLC orthologs in monocots. Similar to *Arabidopsis* FLC, the expression of these FLC-like genes is responsive to a prolonged cold period. The identified tandem arrangement of the FLC, SEP and SQUA subfamilies suggests an origin of these subfamilies by an ancient tandem duplication prior to the origin of extant flowering plants, followed by segmental duplications linked to rounds of polyploidization. Our results close an important gap in our understanding on the origin of developmental key regulatory genes in flowering plants.

SUMMARY OF THE INVENTION

In one aspect of the invention, a method is provided for modulating flowering, seed development, and/or seed germination, such as temperature-dependent flowering, seed development and/or seed germination, in a monocot plant comprising the step of altering the expression and/or activity of an FLC gene and/or protein in said plant or plant part, plant organ or plant cell of said plant. In a further aspect of the invention, a method is provided for producing a monocot plant in which flowering time, seed development and/or seed germination, such as temperature-dependent flowering, seed development and/or seed germination, is modulated, said method comprising expressing in said plant a nucleic acid expression of which results in an altered expression and/or activity of an FLC gene and/or protein in said plant. In a further embodiment, modulating flowering time, seed development, seed maturation comprises accelerating flowering time, or modulating or seed germination comprises delaying seed germination.

In yet another aspect, methods according to the invention are provided wherein altering the expression and/or activity of an FLC gene and/or protein comprises decreasing the expression of and/or activity of an FLC gene and/or protein in said plant, plant part, plant organ or plant cell. In even a further embodiment, said decreasing the expression of and/or activity of a FLC gene and/or protein comprises expressing in said plant, plant part, plant organ or plant cell a chimeric gene comprising the following operably linked elements:

a. a plant-expressible promoter,
b. a nucleic acid which when transcribed results in a decreased expression and/or activity of an FLC gene and/or protein, preferably an endogenous FLC gene and/or protein in said monocot plant, plant part, plant organ or plant cell, and, optionally
c. a 3' end region involved in transcription termination and polyadenylation functional in plants.

In again a further embodiment, said nucleic acid encodes an FLC silencing RNA comprising:

a. at least 19 out of 20 consecutive nucleotides of the nucleotide sequence of an FLC gene present in said monocot plant;
b. at least 19 out of 20 consecutive nucleotides of the complement of the nucleotide sequence of an endogenous FLC gene present in said monocot plant; or
c. a sense region comprising a nucleotide sequence of at least 19 out of 20 consecutive nucleotides of the nucleotide sequence of an FLC gene present in said plant and an antisense region comprising a nucleotide sequence of at least 19 out of 20 consecutive nucleotides of the complement of the nucleotide sequence of said FLC gene present in said plant, wherein said sense and antisense region are capable of forming a double stranded RNA region comprising said at least 19 out of 20 consecutive nucleotides.

In again another embodiment, methods according the invention are provided comprising the step of introducing a mutant allele of an endogenous FLC gene not encoding a functional FLC protein into said plant.

In a further aspect of the invention, a method is provided for delaying (temperature-dependent) flowering, seed development and/or accelerating (temperature-dependent) seed germination in a monocot plant comprising the step of altering the expression and/or activity of an FLC gene and/or protein in said plant or plant part, plant organ or plant cell of said plant. In a further aspect of the invention, a method is provided for producing a monocot plant in which (temperature-dependent) flowering time or seed development is delayed, or seed germination in accelerated, said method comprising altering the expression and/or activity of an FLC gene and/or protein in said plant. In a further aspect of the invention, said altering the expression and/or activity of a FLC gene and/or protein comprises increasing the expression of and/or activity of a FLC gene and/or protein in said plant, plant part, plant organ or plant cell. In yet a further embodiment, said increasing the expression and/or activity of a FLC gene and/or protein comprises expressing in said plant, plant part, plant organ or plant cell a chimeric gene comprising the following operably linked elements:

a. a plant-expressible promoter,
b. a nucleic acid which when transcribed results in an increased activity and/or expression of an FLC gene and/or protein in said monocot plant, plant part, plant organ or plant cell, and
c. optionally, a 3' end region functional in plants.

In again a further embodiment, said nucleic acid encodes an FLC protein.

A further embodiment provides methods according to the invention wherein said monocot plant is a cereal plant, such as a temperate cereal plant, such as a wheat plant.

In again a further embodiment, the coding region of said FLC gene comprises a nucleotide sequence having at least 80% sequence identity to any one of SEQ ID NOs: 1, 3, 5, 7, 9, 11, 13, 15 and 17 or said FLC protein comprises an amino acid sequence having at least 80% sequence identity to any one of SEQ ID NOs: 2, 4, 6, 8, 10, 12, 14, 16 or 18.

Further provided is a chimeric gene as described in the methods of the invention, and a plant, plant part, plant organ, plant cell or seed comprising said chimeric gene.

The invention further provides a monocot plant, plant part, plant organ, plant cell or seed, obtainable according to the methods according to the invention, wherein the expression and/or activity of an FLC gene and/or protein has been altered as compared to a control plant. Also provided is a monocot plant comprising a mutant allele of an FLC gene, said mutant allele resulting in an alteration of the expression and/or activity of the FLC protein encoded by said gene compared to a plant not comprising said mutation in which, optionally, the (temperature-dependent) flowering time, seed development, seed maturation or seed germination has been modulated compared to said plant not comprising said mutation.

According to a further embodiment, the FLC protein of the plant according to the invention has at least 80% sequence identity to any one of SEQ ID NOs: 2, 4, 6, 8, 10, 12, 14, 16 and 18, or wherein said FLC protein is encoded by a nucleotide sequence having at least 80% sequence identity to any one of SEQ ID NOs: 1, 3, 5, 7, 9, 11, 13, 15 and 17. In an even further embodiment, the plant according to the invention is a cereal plant, such as a temperate cereal plant, such as a wheat plant.

Further provided is a method for identifying a monocot plant, such as a cereal plant, or a temperate cereal plant, or a wheat plant, with a modulated (temperature-dependent) flowering time comprising the step of
 a. providing a population of monocot plants, for example a population that has been subjected to mutagenesis,
 b. identifying one or more plants with a mutant allele of an FLC gene, such as an FLC gene having at least 80% sequence identity to any one of SEQ ID NOs: 1, 3, 5, 7, 9, 11, 13, 15 and 17, or an FLC gene encoding a protein having at least 80% sequence identity to any one of SEQ ID NOs: 2, 4, 6, 8, 10, 12, 14, 16 or 18, and
 c. identifying within said plants with a mutant allele of an FLC gene, such as an FLC gene having at least 80% sequence identity to any one of SEQ ID NOs: 1, 3, 5, 7, 9, 11, 13, 15 and 17, or an FLC gene encoding a protein having at least 80% sequence identity to any one of SEQ ID NOs: 2, 4, 6, 8, 10, 12, 14, 16 and 18, one or more plants that have a modulated (temperature-dependent) flowering time compared to a plant of the same species not comprising said mutation.

In a further embodiment, an FLC protein or a functional fragment thereof is provided which is obtainable from a monocot plant, such as from a cereal plant, such as from a temperate cereal, such as from a wheat plant, such as an FLC protein which has an amino acid sequence having at least 80% sequence identity to any one of SEQ ID NOs: 2, 4, 6, 8, 10, 12, 14, 16 and 18.

In a further embodiment, a nucleic acid sequence encoding the FLC protein according to the invention is provided, such as a nucleic acid molecule having at least 80% sequence identity to any one of SEQ ID NOs: 1, 3, 5, 7, 9, 11, 13, 15 and 17.

A further aspect of the invention provides the use of the chimeric gene according to the invention, the protein according to the invention, or the nucleic acid sequence according to the invention to modulate (temperature-dependent) flowering time, seed development and/or seed germination in a monocot plant, such as a cereal plant, such as a temperate cereal plant, such as a wheat plant.

DETAILED DESCRIPTION

Figure 1:
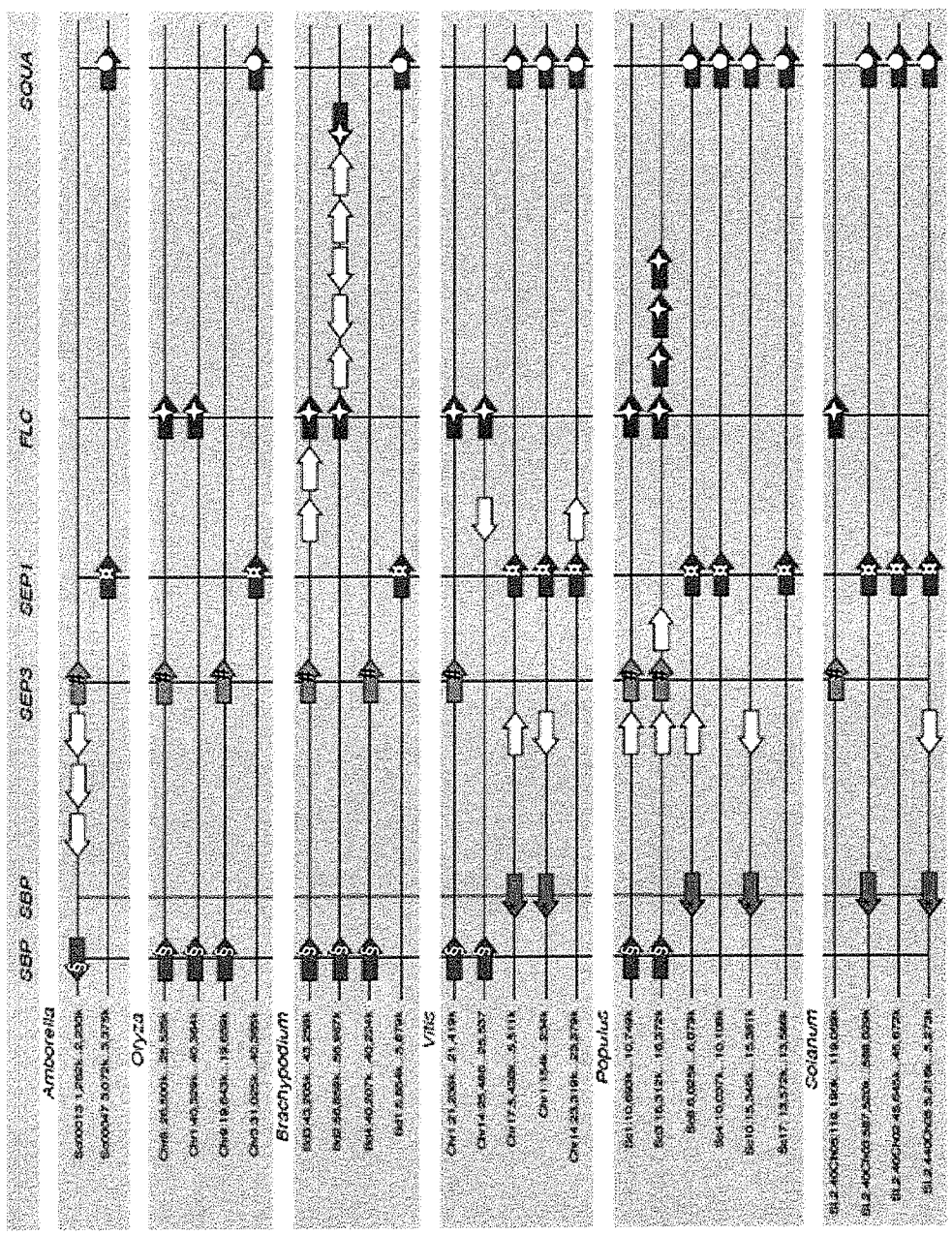
FIG. 1: Conserved tandem arrangements of MADS-box genes in *Amborella, Oryza, Brachypodium, Vitis, Populus* and *Solanum*. Genes that exhibit conserved synteny throughout the angiosperms are represented by arrows with a specific symbol and are connected by vertical lines that are defined at the top of the figure. Loci in white without a symbol did not exhibit synteny. SBP-like genes belonging to different monophyletic groups are differentiated by a different symbol. On the left side of each genome fragment, position coordinates are shown.

The present invention is based on the identification of FLC genes in monocot plant species and their expression regulation by low temperature. A novel approach was followed which, for the first time, allowed the identification of FLC genes in monocot plants, such as (temperate) cereals, previously thought to be non-existent, based on the presently observed conservation of tandem repeat arrangements in core eudicot genomes between SEP3-, SEP1-, SQUA- and FLC-like genes. Six FLC genes have been identified in *Triticum aestivum* (wheat), and three FLC genes have been identified in *Brachypodium* distachion. In *Arabidopsis*, FLC genes have been reported to act as repressors of flowering and of seed dormancy. The current invention therefore opens a novel and previously unrecognized route for modulating flowering time, seed development, seed maturation and seed germination in monocot plants by altering the expression of FLC.

In one aspect of the invention, a method is provided for modulating flowering time, seed development, and/or seed germination, in a monocot plant comprising the step of altering the expression and/or activity of an FLC gene and/or protein in said plant or plant part, plant organ or plant cell of said plant. In a further aspect of the invention, a method is provided for producing a monocot plant in which flowering time, seed development and/or seed germination is modulated, said method comprising expressing in said plant a nucleic acid the expression of which results in an altered expression and/or activity of an FLC gene and/or protein in said plant. Said flowering time, seed development, and/or seed germination may be temperature-dependent. In a further embodiment, modulating flowering time comprises accelerating flowering time, seed development or seed maturation, or modulating seed germination comprises delaying seed germination.

As used herein, "flowering", interchangeably used with "flowering time", relates to the time period from germination to the appearance of the inflorescence or to anthesis. Modulating flowering or flowering time in this respect thus relates to the modulation (increase or decrease) of the time period from germination to the appearance of the inflorescence or to anthesis. In a preferred embodiment, the invention relates to modulation (increase or decrease) of temperature dependent flowering or flowering time.

As used herein, "seed development", relates to the development from fertilization to mature seed, including embryo development and seed maturation. Seed development as used herein includes in particular also seed maturation, i.e. the accumulation of storage tissue in the seed. Modulating seed development accordingly involves modulating the time from fertilization to mature seed. In a preferred embodiment, the invention relates to modulation (increase or decrease) of temperature-dependent seed development.

As used herein, "seed germination", relates to the emergence of a (viable) seedling from a seed. Modulating seed germination in this respect thus relates to modulating (increasing or decreasing) the time period from imbibition (the exposure to moist conditions, e.g. by contacting with a growth medium, such as planting in the soil) to the emergence of the seedling. In a preferred embodiment, the invention relates to modulation (increase or decrease) of temperature-dependent seed germination.

It is to be understood that the term "an FLC gene and/or protein" may be exactly one such gene or protein but also includes embodiments where at least one such FLC gene and/or protein are concerned. Six FLC genes have been found in *Triticum aestivum*, accordingly, for *T. aestivum* as well as other monocot plants comprising more than one FLC gene, the present invention in several embodiments contemplates reference to at least one FLC gene and/or protein, but also at least two, at least three, at least four, at least five FLC or at least six genes and/or proteins. If comparative reference is made from a mutant FLC gene/allele to a naturally occurring FLC gene and/or protein, it is understood that in case more than one FLC gene and/or protein exists, reference is made to the one with the highest sequence identity to the mutant FLC gene/allele concerned.

The term "temperature-dependent" interchangeably used with the term "cold-induced", as used herein, refer to the requirement for certain plant species of a period of low temperature (cold) for certain processes such as flowering or seed germination to be activated. This is nessecary for in particular temperate plant species to be able to sense the passing of winter into optimal reproductive environmental conditions (Amasino et al (2010), supra). For example, winter wheat requires a cold period of about 8 weeks before induction of flowering, while this is about 3-8 weeks for *Brachypodium* (Schwartz et al. (2010) Bioenergy Research 3: 38-46). The required temperature for such a cold period is generally about about 4° C.

In relation to temperature dependency, the term "vernalization", as used herein refers to exposure of a plant or seed to low temperature for a genetically determined length of time in order to trigger flowering, seed development or seed germination. Vernalization thus is for example the acquisition of a plant's ability to flower in the spring by exposure to the prolonged cold of winter. After vernalization, plants have acquired the ability to flower, but they may require additional seasonal cues or weeks of growth before they will actually flower. Many plants that grow in temperate climates require vernalization and must experience a period of low winter temperature to initiate or accelerate the flowering process. This ensures that reproductive development and seed production occurs in spring and summer, rather than in autumn. The needed cold is often expressed in chill hours. Typical vernalization temperatures are between 5 and 10 degrees Celsius, but under experimental conditions 4 degrees Celcius is often used.

Temperature-dependent germination relates to the percentage of seeds germination following a exposure at a particular temperature, as e.g. described in Chiang et al. 2009, supra).

FLC genes, also "Flowering Locus C genes" are genes encoding FLC proteins or "Flowering Locus C proteins". FLC genes are MADS-box genes. In *Arabidopsis thaliana*, FLC is a central repressor of floral transition, where it inhibits flowering by directly repressing the activity of central flowering promoters, namely SUPPRESSOR OF OVEREXPRESSION OF CONSTANS (SOC1), FLOWERING LOCUS D (FD) and FLOWERING LOCUS T (FT). Also in *Arabidopsis*, FLC controls temperature-dependent seed germination and natural variation at the FLC locus and in FLC expression is associated with natural variation in temperature dependent germination (Chiang et al. 2009, supra) The term "functional FLC protein" relates to the activity of an FLC protein which includes at least one and preferably more than one or even all of its biological functions, including activation or repression of expression of downstream targets of FLC mentioned in e.g. Deng et al., 2001 PNAS 108:6680-6685), or by evaluating the binding to interaction partners such as SVP (Lee et al., 2007, Genes Dev 21:397-402).

FLC genes present in monocots can be any of the monocot FLC genes as described herein. For example, the FLC genes can be the FLC genes as described in Table 1 below. Monocot FLC genes can also be genes with a coding sequence having at least 80%, at least 85%, at least 90%, at least 95%, 98%, 99% or 100% sequence identity with SEQ ID NO: 1, or with SEQ ID NO: 3, or with SEQ ID NO: 5, or with SEQ ID NO: 7, or with SEQ ID NO: 9, or with SEQ ID NO: 11, or with SEQ ID NO: 13, or with SEQ ID NO: 15; or with SEQ ID NO: 17. In addition to the degree of sequence identity as described above, such FLC genes may also have the same functionality as the ones of any one of SEQ ID NO: 1, 3, 5, 7, 9, 11, 13, 15 and 17.

FLC proteins can be proteins encoded by the monocot FLC genes as described herein. For example, the FLC proteins can be the FLC proteins encoded by the FLC genes in Table 1 as described herein. Monocot FLC proteins can also be proteins with an amino acid sequence having at least 80%, at least 85%, at least 90%, at least 95%, 98%, 99% or 100% sequence identity with SEQ ID NO: 2, or with SEQ ID NO: 4, or with SEQ ID NO: 6, or with SEQ ID NO: 8, or with SEQ ID NO: 10, or with SEQ ID NO: 12, or with SEQ ID NO: 14, or with SEQ ID NO: 16, or with SEQ ID NO: 18.

FLC genes from other monocot species can be identified using the methods as described in Example 2. Once FLC genes in a certain monocot species have been identified, orthologous FLC genes in related monocot species or in other cultivars or varieties can be identified using methods well known in the art, e.g., alignments, either manually or by using computer programs such as BLAST (Altschul et al. (1990), Journal of Molecular Biology, 215, 403-410), which stands for Basic Local Alignment Search Tool or ClustalW (Thompson et al. (1994), Nucleic Acid Res., 22, 4673-4680) or any other suitable program which is suitable to generate sequence alignments.

FLC genes in related monocot species or in other cultivars or varieties can also be identified using hybridization with a probe having the nucleotide sequence of an FLC gene or part thereof. Stringent hybridization conditions, such as those described below, can be used to identify nucleotide sequences, which are substantially identical to a given nucleotide sequence. For example, FLC genes from other monocot species than the specific sequences disclosed herein are said to be substantially identical or essentially similar if they can be detected by hybridization under stringent, preferably highly stringent conditions. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

Monocot plants, also known as monocotyledons or monocotelydon plants, are well known in the art and are plants which have one cotyledon in their seeds. Monocot plants comprise *Oryza* sp. (including rice), *Zea* sp. (including maize), *Saccharum* sp. (including sugarcane), *Triticum* sp. (including wheat), *Hordcum, Secalc, Avena, Lolium, Fcstuca Brachypodium distachion, Musa* sp. (including banana).

Accelerating (temperature-dependent) flowering or seed development (wherein seed development as used herein includes in particular seed maturation) can be accelerating any of the two by a significant time, such as by between 1 and 60 days, depending on the accession, as compared to flowering time, seed development (including seed maturation) of a plant with wild-type FLC expression and activity, such as an acceleration of about 1 to 60 days, about 10 to 50 days, about 1 to 20 days, about 20 to 40 days, about 40 to 60 days, e.g. an acceleration of about 5 days, about 10 days, about 20 days, about 30 days, about 40 days, about 50 days or about 60 days. Delaying seed germination can be delaying seed germination by about up to 4 weeks as compared to germination of a plant with wild-type FLC expression and activity, such as delay of about 1 to 4 weeks, about 1 to 2 weeks, about 2 and 3 weeks, about 2 to 4 weeks, e.g. a delay of about 1 week, about 2 weeks, about 3 weeks or about 4 weeks. Delaying seed germination can also be preventing seed germination altogether, i.e the seeds do not germinate.

Plants with wild-type FLC expression and activity are plants having expression and/or activity of at least one FLC gene as it most commonly occurs in nature. Said plants do not comprise heterologous DNA to increase or reduce FLC expression and/or activity, and said plants do not comprise knock-out FLC alleles.

Accelerating temperature-dependent flowering in this respect also relates to reducing the length of the cold period required for the induction of flowering. The length of the cold period required for the induction of flowering can be reduced by up to 8 weeks, depending on the accession, as compared to the length of the cold period required for the induction of flowering of a plant with wild-type FLC expression and activity, such as a reduction in the length of the cold period between 1 and 8 weeks, between 1 and 4 weeks, between 4 and 8 weeks, between 2 and 6 weeks, between 3 and 5 weeks, e.g. a reduction by about 1 week, by about 2 weeks, by about 3 weeks, by about 4 weeks, by about 5 weeks or by about 6 weeks, by about 7 weeks, or by about 8 weeks. Reducing the length of the cold period required for the induction of flowering in this respect can also mean completely eliminating the requirement for a cold period before flowering. Plants with wild-type FLC expression and activity are plants having expression and/or activity of at least one FLC gene as it most commonly occurs in nature. Said plants do not comprise heterologous DNA to increase or reduce FLC expression and/or activity, and said plants do not comprise knock-out FLC alleles.

Accelerating temperature dependent flowering in this respect also relates to increasing the lowest temperature of the cold period required for the induction of flowering. The lowest temperature of the cold period required for the induction of flowering can, depending on the accession, be increased up to 10° C., such as an increase between 1 and 10° C., between 5 and 10° C., between 1 and 5° C., between 3 and 8° C., between 4 and 6° C., e.g. an increase of about 2° C., about 4° C., about 5° C., about 6° C. about 8° C., or about 10° C., as compared to lowest temperature required for induction of flowering of a plant with wild-type FLC expression and activity. Increasing the lowest temperature of the cold period required for the induction of flowering in this respect can also mean completely eliminating the requirement for a cold period before flowering. Plants with wild-type FLC expression and activity are plants having expression and/or activity of at least one FLC gene as it most commonly occurs in nature. Said plants do not comprise heterologous DNA to increase or reduce FLC expression and/or activity, and said plants do not comprise knock-out FLC alleles.

The terms "expressing in said plant" as well as "expressing in a plant, plant part, plant organ or plant cell" as used throughout the present application relate to the occurrence of an expression product of a nucleic acid resulting from transcription of said nucleic acid. In connection with some embodiments of the methods according to the invention, the term may additionally include introducing a chimeric gene comprising the nucleic acid to be expressed in the plant.

In yet another aspect, methods according to the invention are provided wherein altering the expression and/or activity of an FLC gene and/or protein comprises decreasing the expression of and/or activity of an FLC gene and/or protein in said plant, plant part, plant organ or plant cell. In even a further embodiment, said decreasing the expression of and/or or activity of a FLC gene and/or protein comprises expressing in said plant, plant part, plant organ or plant cell a chimeric gene comprising the following operably linked elements:

a. a plant-expressible promoter, b. a nucleic acid which when transcribed yields an RNA molecule that results in a decreased expression and/or activity of an endogenous FLC gene and/or protein, i.e. an FLC gene naturally present (i.e. endogenous) in said monocot plant, plant part, plant organ or plant cell, and, optionally c. a 3' end region involved in transcription termination and polyadenylation functional in plants.

A chimeric gene is an artificial gene constructed by operably linking fragments of unrelated genes or other nucleic acid sequences. In other words "chimeric gene" denotes a gene which is not normally found in a plant species or refers to any gene in which the promoter or one or more other regulatory regions of the gene are not associated in nature with a part or all of the transcribed nucleic acid, i. e. are heterologous with respect to the transcribed nucleic acid. The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism). For example, the chimeric gene disclosed herein is a heterologous nucleic acid.

The chimeric gene may also comprise a transcription termination or polyadenylation sequence functional in a plant cell, particularly a monocot, more preferably a cereal or wheat plant cell. As a of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1.

An RNA molecule that results in a decreased expression and/or activity of an FLC gene and/or protein can be an RNA encoding a protein which inhibits expression and/or activity of said FLC protein. Further, said RNA molecule that results in a decreased expression and/or activity of an FLC gene and/or protein can also be an RNA molecule which inhibits expression of a gene which is an activator of expression and/or activity of said FLC protein. For example *FRIGIDA* in *Arabidopsis* promotes FLC and FCA in *Arabidopsis* and other members of the autonomous pathway act to reduce FLC levels in *Arabidopsis* (Michaels and Amasino 2001, Science 290: 344-347). Said RNA molecule that inhibits the expression and/or activity of an FLC gene and/or protein may also be an RNA molecule that directly inhibits expression and/or activity of an FLC gene and/or protein, such as an RNA which mediates silencing of said FLC gene.

Decreasing the expression and/or activity of the FLC gene and/or protein can be decreasing the amount of functional FLC protein produced. Said decrease can be a decrease with at least 30%, 40%, 50%, 60%, 70%, 80%, 90%, 95% or 100% (i.e. no functional FLC protein is produced by the cell) as compared to the amount of functional FLC protein produced by a cell with wild type FLC expression levels and activity. Said decrease in expression and/or activity can be a constitutive decrease in the amount of functional FLC protein produced. Said decrease can also be a temporal/inducible decrease in the amount of functional FLC protein produced. The amount of functional FLC protein (FLC activity) as well as the fact whether an FLC protein is function can e.g be determined by evaluating the expression/activation of downstream targets of FLC any of the targets mentioned in e.g. Deng et al., 2001 PNAS 108:6680-6685), or by evaluating the binding of FLC to interaction partners such as SVP (Lee et al., 2007, Genes Dev 21:397-402).

The expression and/or activity of the FLC gene and/or protein can conveniently be reduced or eliminated by transcriptional or post-transcriptional silencing of the expression of endogenous FLC genes. To this end and within the chimeric gene described above, a silencing RNA molecule is introduced in the plant cells targeting the endogenous FLC encoding genes. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having at least 95%, at least 96%, at least 97% at least 98%, at least 99% or 100% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). An ihpRNA is an intron-containing hairpin RNA, which has the same general structure as an hpRNA, but the RNA molecule additionally comprises an intron in the loop of the hairpin that is capable of being spliced in the cell in which the ihpRNA is expressed. The use of an intron minimizes the size of the loop in the hairpin RNA molecule following splicing, and this increases the efficiency of interference. See, for example, Smith et al (2000) Nature 407:319-320. In fact, Smith et al, show 100% suppression of endogenous gene expression using ihpRNA-mediated interference. In some embodiments, the intron is the ADH1 intron 1. Methods for using ihpRNA interference to inhibit the expression of endogenous plant genes are described, for example, in Smith et al, (2000) Nature 407:319-320; Waterhouse and Helliwell, (2003) Nat. Rev. Genet. 4:29-38; Helliwell and Waterhouse, (2003) Methods 30:289-295 and US2003180945, each of which is herein incorporated by reference. A transient assay for the efficiency of hpRNA constructs to silence gene expression in vivo has been described by Panstruga, et al. (2003). The chimeric gene for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene present in the plant. Thus, it is the loop region that determines the specificity of the RNA interference. See, for example, WO0200904 herein incorporated by reference.

Silencing RNA may also be artificial micro-RNA molecules as described e.g. in WO2005/052170, WO2005/047505 or US 2005/0144667, or ta-siRNAs as described in WO2006/074400 (all documents incorporated herein by reference).

Within the chimeric genes of the invention, als amplicon chimeric genes can be used. Amplicon chimeric genes according to the invention comprise a plant virus-derived sequence that contains all or part of the target gene but generally not all of the genes of the native virus. The viral sequences present in the transcription product of the chimeric gene allow the transcription product to direct its own replication. The transcripts produced by the amplicon may be either sense or antisense relative to the target sequence. Methods of using amplicons to inhibit the expression of endogenous plant genes are described, for example, in U.S. Pat. No. 6,635,805, which is herein incorporated by reference.

In some embodiments, the nucleic acid expressed by the chimeric gene of the invention is catalytic RNA or has ribozyme activity specific for the target sequence. Thus, the polynucleotide causes the degradation of the endogenous messenger RNA transcribed from the target gene/sequence, resulting in reduced expression of the protein present in the plant. This method is described, for example, in U.S. Pat. No. 4,987,071, herein incorporated by reference.

In one embodiment, the nucleic acid expressed by the chimeric gene of the invention encodes a zinc finger protein that binds to the gene encoding said protein, resulting in reduced expression of the target gene. In particular embodiments, the zinc finger protein binds to a regulatory region of said gene. In other embodiments, the zinc finger protein binds to a messenger RNA encoding said protein, thereby preventing its translation. Methods of selecting sites for targeting by zinc finger proteins have been described, for example, in U.S. Pat. No. 6,453,242, and methods for using zinc finger proteins to inhibit the expression of genes in plants are described, for example, in US2003/0037355, each of which is herein incorporated by reference.

In another embodiment, the nucleic acid expressed by the chimeric gene of the invention encodes a TALE protein that binds to a gene encoding a protein having the activity of an FLC protein present in the plant, resulting in reduced expression of the gene. In particular embodiments, the TALE protein binds to a regulatory region of said gene. In other embodiments, the TALE protein binds to a messenger RNA encoding said protein and prevents its translation. Methods of selecting sites for targeting by TALE proteins have been described in e.g. Moscou M J, Bogdanove A J (2009) (A simple cipher governs DNA recognition by TAL effectors. Science 326:1501) and Morbitzer R, Romer P, Boch J, Lahaye T (2010) (Regulation of selected genome loci using de novo-engineered transcription activator-like effector (TALE)-type transcription factors. Proc Natl Acad Sci USA 107:21617-21622).

In some embodiments, to reduce or decrease the expression and/or activity of an FLC gene and/or protein, a polypeptide or nucleic acid encoding an RNA molecule which is translated into a polypeptide can be introduced into a plant within the chimeric gene according to the invention, wherein the polypeptide is capable of reducing the expression and/or activity of said FLC protein directly, i.e. the chimeric gene encodes an inhibitory protein or polypeptides.

In one embodiment, such an FLC inhibitory protein or polypeptide can be an antibody (including a nanobody etc) that binds to the FLC protein present in the plant and reduces the activity thereof. In another embodiment, the binding of the antibody results in increased turnover of the antibody complex by cellular quality control mechanisms. The expression of antibodies in plant cells and the inhibition of molecular pathways by expression and binding of antibodies to proteins in plant cells are well known in the art. See, for example, Conrad and Sonnewald, (2003) Nature Biotech. 21:35-36, incorporated herein by reference.

In another embodiment, such inhibitory protein or polypeptide may also be a dominant negative FLC protein or protein fragment.

In an alternative embodiment, decreasing the functional amount of an FLC protein can be achieved by contacting the plant or plant cell with molecules interfering with the function of the FLC protein present in the plant, e. g. by triggering aggregation of the target protein (interferor peptides) as e.g. described in WO2007/071789 and WO2008/148751.

In an even further embodiment, decreasing the expression and/or activity of an FLC gene and/or protein can be achieved by contacting the plant or plant cell can with so-called alphabodies specific for the FLC protein present in the plant, i.e. non-natural proteinaceous molecules that can antagonize protein function, as e.g. described in WO2009/030780, WO2010/066740 and WO2012/092970.

In alternative embodiments, decreasing the expression and/or activity of an FLC gene and/or protein can be achieved by inhibition of the expression said FLC protein present in the plant. Inhibition of the expression of said FLC gene and/or protein can be induced at the desired moment using a spray (systemic application) with inhibitory nucleic acids, such as RNA or DNA molecules that function in RNA-mediated gene silencing (similar to the above described molecules), as e.g. described in WO2011/112570 (incorporated herein by reference).

Thus, in a further embodiment, the chimeric gene encodes an RNA molecule comprising:
  a. at least 19 out of 20 consecutive nucleotides of the nucleotide sequence of an FLC gene present in said monocot plant;
  b. at least 19 out of 20 consecutive nucleotides of the complement of the nucleotide sequence of an FLC gene present in said monocot plant; or
  c. a sense region comprising a nucleotide sequence of at least 19 out of 20 consecutive nucleotides of the nucleotide sequence of an FLC gene present in said plant and an antisense region comprising a nucleotide sequence of at least 19 out of 20 consecutive nucleotides of the complement of the nucleotide sequence of said FLC gene present in said plant, wherein said sense and antisense region are capable of folining a double stranded RNA region comprising said at least 19 out of 20 consecutive nucleotides.

Thus, the RNA molecule may comprise at least 19 out of 20 consecutive nucleotides of (the complement of) a nucleotide sequence having at least 80%, 85%, 90%, 95%, 98%, 99% or 100% sequence identity to any one of SEQ ID NOs: 1, 3, 5, 7, 9, 11, 13, 15 and 17, or the RNA molecule may comprise at least 19 out of 20 consecutive nucleotides of (the complement of) a nucleic acid encoding a protein having at least 80%, 85%, 90%, 95%, 98%, 99% or 100% sequence identity to any one of SEQ ID NOs: 2, 4, 6, 8, 10, 12, 14, 16 and 18.

In again another embodiment, methods according the invention are provided comprising the step of introducing a knock-out allele of an endogenous FLC gene.

A "knock-out allele of an endogenous FLC gene" or a "knock-out FLC allele" as used herein is an FLC allele which encodes a non-functional FLC protein (i.e. a protein having no FLC activity) or results in a significantly reduced amount of FLC protein (by for example a mutation in a regularory region such as the promoter), or which encodes an FLC protein with significantly reduced activity. Said "knock-out FLC allele" can be a mutant FLC allele, which may encode no FLC protein, or which may encode a non-functional FLC protein. The allele may also be referred to as an inactivated allele.

Said "significantly reduced amount of FLC protein" can be a reduction in the amount (or levels) of FLC protein produced by the cell comprising a knock-out FLC allele by at least 30%, 40%, 50%, 60%, 70%, 80%, 90%, 95% or 100% (i.e. no FLC protein is produced by the allele) as compared to the amount of the FLC protein produced by the wild-type FLC allele. FLC amounts or levels, e.g the amount of a transcript (e.g. an mRNA) or a protein can be measured according to various methods known in the art such as (quantitative) RT-PCR, northern blotting, microarmy analysis, western blotting, ELISA and the like.

A "significantly reduced activity" can be a reduction in the activity of FLC protein produced by the cell comprising a knock-out FLC allele by at least 30%, 40%, 50%, 60%, 70%, 80%, 90%, 95% or 100% (i.e. no FLC activity) as compared to the FLC activity of the wild-type FLC allele. Assays for FLC activity are described elsewhere in this application.

A "wild-type FLC allele" as used herein refers to a typical form of an allele as it most commonly occurs in nature, such as the FLC alleles as decribed in this application, e.g. SEQ ID NOs 1-18 or the ones provided in table 1.

Basically, any mutation in the wild type FLC nucleic acid sequences which results in an FLC protein comprising at least one amino acid insertion, deletion and/or substitution relative to the wild type FLC protein can lead to significantly reduced or no biological activity. It is, however, understood that certain mutations in the FLC protein are more likely to result in a complete abolishment of the biological activity of the FLC protein, such as mutations whereby significant portions of the functional domains, such as the MADS domain are lacking. The MADS-domain is responsible for DNA binding through homo- or heterodimerization and its absence would thus impair the downstream regulatory function of the FLC transcription factor.

A "mutant FLC gene" or a "mutant FLC allele" refers to FLC genes or alleles comprising one or more mutations, such as a "missense mutation", a "nonsense mutation" or "STOP codon mutation" (including a mutation resulting in no functional FLC protein ("knock-out allele of an FLC gene"), an "insertion mutation", a "deletion mutation" or a "frameshift mutation" (the latter two including one or more mutations resulting in a "knock-out allele of an FLC gene") with respect to a wild-type FLC gene or allele, such as such as the FLC genes and alleles as decribed in this application, e.g. as represented by SEQ ID NOs 1-18 or the ones provided in table 1.

A nonsense mutation in an FLC allele, as used herein, is a mutation in an FLC allele whereby one or more translation stop codons are introduced into the coding DNA and the corresponding mRNA sequence of the corresponding wild type FLC allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. Thus, a full knockout mutant FLC allele may comprise a nonsense mutation wherein an in-frame stop codon is introduced in the FLC codon sequence by a single nucleotide substitution, such as the mutation of CAG to TAG, TGG to TAG, TGG to TGA, or CAA to TAA. Alternatively, a full knockout mutant FLC allele may comprise a nonsense mutation wherein an in-frame stop codon is introduced in the FLC codon sequence by double nucleotide substitutions, such as the mutation of CAG to TAA, TGG to TAA, or CGG to TAG or TGA. A full knockout mutant FLC allele may further comprise a nonsense mutation wherein an in-frame stop codon is introduced in the FLC codon sequence by triple nucleotide substitutions, such as the mutation of CGG to TAA. The truncated protein lacks the amino acids encoded by the coding DNA downstream of the mutation (i.e. the C-terminal part of the FLC protein) and maintains the amino acids encoded by the coding DNA upstream of the mutation (i.e. the N-terminal part of the FLC protein).

A missense mutation in an FLC allele, as used herein, is any mutation (deletion, insertion or substitution) in an FLC allele whereby one or more codons are changed in the coding DNA and the corresponding mRNA sequence of the corresponding wild type FLC allele, resulting in the substitution of one or more amino acids in the wild type FLC protein for one or more other amino acids in the mutant FLC protein.

A frameshift mutation in an FLC allele, as used herein, is a mutation (deletion, insertion, duplication of one or more nucleotides, and the like) in an FLC allele that results in the nucleic acid sequence being translated in a different frame downstream of the mutation.

An "insertion mutation" is present if one or more codons have been added in the coding sequence of the nucleic acid resulting in the presence of one or more amino acids in the translated protein, whereas a "deletion mutation" is present if one or more codons have been deleted in the coding sequence of the nucleic acid resulting in the deletion of one or more amino acids in the translated protein.

Said mutant allele can be introduced into said plant e. g. through mutagenesis. "Mutagenesis", as used herein, refers to the process in which plant cells are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet 13:152-156), transposon mutagenesis (McKenzie et al. (2002) Theor Appl Genet 105:23-33), or tissue culture mutagenesis (induction of somaclonal variations), or a combination of two or more of these. Thus, the desired mutagenesis of one or more FLC genes or alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, plants are regenerated from the treated cells using known techniques. For instance, the resulting seeds may be planted in accordance with conventional growing procedures and following pollination seed is formed on the plants. Additional seed that is formed as a result of such pollination in the present or a subsequent generation may be harvested and screened for the presence of mutant FLC alleles. Several techniques are known to screen for specific mutant alleles, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant DA1 alleles are described in the Example below.

Said mutant allele can also be introduced via gene targeting techniques. The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150.

Said mutant allele can also be introduced through introgression of a mutant allele into said plant.

In a further aspect of the invention, a method is provided for delaying (temperature-dependent) flowering time and/or seed development and/or accelerating seed germination, in a monocot plant comprising the step of altering the expression and/or activity of an FLC gene and/or protein in said plant or plant part, plant organ or plant cell of said plant. In a further aspect of the invention, a method is provided for producing a monocot plant in which flowering time or seed development is delayed, and/or seed germination in accelerated, said method comprising altering the expression and/or activity of an FLC gene and/or protein in said plant. In a further aspect of the invention, said altering the expression and/or activity of an FLC gene and/or protein comprises increasing the expression of and/or activity of a FLC gene and/or protein in said plant, plant part, plant organ or plant cell. In yet a further embodiment, said increasing the expression of and/or activity of a FLC gene and/or protein comprises expressing in said plant, plant part, plant organ or plant cell a chimeric gene comprising the following operably linked elements:
  a. a plant-expressible promoter,
  b. a nucleic acid which when transcribed results in an increased activity and/or expression of an FLC gene and/or protein in said monocot plant, plant part, plant organ or plant cell, and
  c. optionally, a 3' end region functional in plants.

Delaying (temperature-dependent) flowering time or seed development (including seed maturation) can be any of the three with up to 20 days as compared to flowering time of a plant with wild-type FLC expression and activity, such as a delay of about 1 to 60 days, about 10 to 50 days about 1 to 20 days, about 20-40 days, about 40-60 days, e.g. a delay of about 5 days, about 10 days, about 20 days, about 30 days, about 40 days, about 50 days or about 60 days. Accelerating seed germination can be accelerating seed germination by about up to 4 weeks as compared to germination of a plant with wild-type FLC expression and activity, such an acceleration of about 1 to 4 weeks, about 2 to 3 weeks, about 1 to 2 weeks, about 3 to 4 weeks, e.g. a an acceleration of about 1 week, or about 2 weeks, about 3 weeks or about 4 weeks. Plants with wild-type FLC expression and activity are plants having expression and/or activity of at least one FLC gene as it most commonly occurs in nature. Said plants do not comprise heterologous DNA to increase or reduce FLC expression and/or activity, and said plants do not comprise knock-out FLC alleles.

Delaying temperature-dependent flowering time in this respect also relates to increasing the length of the cold period required for the induction of flowering. The length of the cold period required for the induction of flowering can be increased up to about 8 weeks as compared to germination of a plant with wild-type FLC expression and activity, such as a delay of about 1 to 8 weeks, about 1 to 4 weeks, about 4 to 8 weeks, about 2 to 6 weeks, about 3 to 4 weeks, e.g. a delay of about 1 week, about 2 weeks, about 3 weeks, about, 4 weeks, about 5 weeks about 6 weeks, about 7 weeks, or about 8 weeks. Delaying flowering time in this respect also relates to decreasing the lowest temperature of the cold period required for the induction of flowering. The lowest temperature of the cold period required for the induction of flowering can be decreased up to 10° C. as compared to germination of a plant with wild-type FLC expression and activity, such as a a decrease of about 1-10° C., about 1-5° C., about, 5-10° C., about 2 to 8° C., about 4 to 6° C., such as a decrease by about 2° C., about 4° C., about 5° C., about 6° C., about 8° C. or about 10° C. Plants with wild-type FLC expression and activity are plants having expression and/or activity of at least one FLC gene as it most commonly occurs in nature. Said plants do not comprise heterologous DNA to increase or reduce FLC expression and/or activity, and said plants do not comprise knock-out FLC alleles.

Increasing the expression and/or activity of the FLC protein can be increasing the amount of (functional) FLC protein produced or increasing the expression and/or activity of FLC. Said increase in the amount of (functional) FLC protein produced can be an increase of at least 2-fold, 4-fold, 10-fold, 25-fold, 50-fold, 75-fold, 100-fold or even more as compared to the amount of (functional) FLC protein produced by a cell with wild type FLC expression levels. Said increase in expression and/or activity can be a constitutive increase in the amount of (functional) FLC protein produced. Said increase can also be a temporal decrease in the amount of (functional) FLC protein produced. An increase in the amount or activity of FLC can be measured as described elsewhere in this application. An increase in the expression and/or activity of FLC can be achieved for example by operably linking an FLC coding region to a promoter, such as any of the promoters decribed herein below, thereby driving FLC expression in e.g. a constitutive, inducible, temporal or tissue specific fashion depending on the choice of promoter.

Said nucleic acid which when transcribed results in an increased activity and/or expression of an FLC gene and/or protein can be a nucleic acid encoding a protein which activates expression and/or activity of said FLC protein. Examples include FRIGIDA, FRIGIDA LIKE1, FRIGIDA LIKE 2, FRIGIDA ESSENTIAL 1, SUF4 and FLC EXPRESSOR (Choi et al (2011) Plant Cell 23: 289-303.

In one embodiment, the nucleic acid encodes a zinc finger protein that binds to the gene encoding an FLC protein present in the plant, resulting in an increased expression of the target gene. In particular embodiments, the zinc finger protein binds to a regulatory region of said gene, thereby activating its expression. Methods of selecting sites for targeting by zinc finger proteins have been described, for example, in U.S. Pat. No. 6,453,242, and methods for using zinc finger proteins to inhibit the expression of genes in plants are described, for example, in US2003/0037355, each of which is herein incorporated by reference.

In another embodiment, the nucleic acid encodes a TALE protein that binds to a gene encoding an FLC protein present in the plant, resulting in an increased expression of the gene. In particular embodiments, the TALE protein binds to a regulatory region of said gene, thereby activating its expression. In other embodiments, the TALE protein binds to a messenger RNA encoding said protein and prevents its translation. Methods of selecting sites for targeting by TALE proteins have been described in e.g. Moscou M J, Bogdanove A J (2009) (A simple cipher governs DNA recognition by TAL effectors. Science 326:1501) and Morbitzer R, Romer P, Boa J, Lahaye T (2010) (Regulation of selected genome loci using de novo-engineered transcription activator-like effector (TALE)-type transcription factors. Proc Natl Acad Sci USA 107:21617-21622).

In again a further embodiment, said nucleic acid encodes an FLC protein, such as an FLC protein as deeribed elsewhere in this application.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) Mol Gen Genet. 212(1):182-90, the subterranean clover vitus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) Plant Cell 8(1):15-30), stem-specific promoters (Keller et al., (1988) EMBO J. 7(12): 3625-3633), leaf specific promoters (Hudspeth et al. (1989) Plant Mol Biol. 12: 579-589), mesophyl-specific promoters (such as the light-inducible Rubisco promoters), root-specific promoters (Keller et al. (1989) Genes Dcv. 3: 1639-1646), tuber-specific promoters (Keil et al. (1989) EMBO J. 8(5): 1323-1330), vascular tissue specific promoters (Peleman et al. (1989) Gene 84: 359-369), stamen-selective promoters (WO 89/10396, WO 92/13956), dehiscence zone specific promoters (WO 97/13865) and the like. "Plant-expressible promoters" can also be inducible promoters, such as temperature-inducible promoters or chemically inducible promoters.

Suitable promoters for the invention are constitutive plant-expressible promoters leading to constitutive expression of the chimeric gene of the invention and thus to e. g. a constitutive increase or decrease in the expression and/or activity of an FLC gene and/or protein. Constitutive plant-expressible promoters are well known in the art, and include the CaMV35S promoter (Harpster et al. (1988) Mol Gen Genet. 212(1):182-90), Actin promoters, such as, for example, the promoter from the Rice Actin gene (McElroy et al., 1990, Plant Cell 2:163), the promoter of the Cassava Vein Mosaic Virus (Verdaguer et al., 1996 Plant Mol. Biol. 31: 1129), the GOS promoter (de Pater et al., 1992, Plant J. 2:837), the Histone H3 promoter (Chaubet et al., 1986, Plant Mol Biol 6:253), the *Agrobacterium tumefaciens* Nopaline Synthase (Nos) promoter (Depicker et al., 1982, J. Mol. Appl. Genet. 1: 561), or Ubiquitin promoters, such as, for example, the promoter of the maize Ubiquitin-1 gene (Christensen et al., 1992, Plant Mol. Biol. 18:675).

Other suitable promoters for the invention are inducible promoters, such as inducible promoters (e.g. stress-inducible promoters, drought-inducible promoters, hormone-inducible promoters, chemical-inducible promoters, etc.), tissue-specific promoters, developmentally regulated promoters and the like. A variety of plant gene promoters that regulate gene expression in response to environmental, hormonal, chemical, developmental signals, and in a tissue-active manner can be used for expression of a sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like.

Examples of promoters that can be used to practice this invention are those that elicit expression in response to stresses, such as the RD29 promoters that are activated in response to drought, low temperature, salt stress, or exposure to ABA (Yamaguchi-Shinozaki et al., 2004, Plant Cell, Vol. 6, 251-264; WO12/101118), but also promoters that are induced in response to heat (e.g., see Ainley et al. (1993) Plant Mol. Biol. 22: 13-23), light (e.g., the pea rbcS-3A promoter, Kuhlemeier et al. (1989) Plant Cell 1: 471-478, and the maize rbcS promoter, Schaffher and Sheen (1991) Plant Cell 3: 997-1012); wounding (e.g., wunl, Siebertz et al. (1989) Plant Cell 1: 961-968); pathogens (such as the PR-I promoter described in Buchel et al. (1999) Plant Mol. Biol. 40: 387-396, and the PDF 1.2 promoter described in Manners et al. (1998) Plant Mol. Biol. 38: 1071-1080), and chemicals such as methyl jasmonate or salicylic acid (e.g., see Gatz (1997) Annu. Rev. Plant Physiol. Plant Mol. Biol. 48: 89-108). In addition, the timing of the expression can be controlled by using promoters such as those acting at senescence (e.g., see Gan and Amasino (1995) Plant Cell 13(4): 935-942); or late seed development (e.g., see Odell et al. (1994) Plant Physiol. 106: 447-458).

Use may also be made of salt-inducible promoters such as the salt-inducible NHX1 promoter of rice landrace Pokkali (PKN) (Jahan et al., 6th International Rice Genetics symposium, 2009, poster abstract P4-37), the salt inducible promoter of the vacuolar H+-pyrophosphatase from *Thellungiella halophila* (TsVP1) (Sun et al., BMC Plant Biology 2010, 10:90), the salt-inducible promoter of the *Citrus sinensis* gene encoding phospholipid hydroperoxide isoform gpx1 (Avsian-Kretchmer et al., Plant Physiology July 2004 vol. 135, p 1685-1696).

In alternative embodiments, tissue-specific and/or developmental stage-specific promoters are used, e.g., promoter that can promote transcription only within a certain time frame of developmental stage within that tissue. See, e.g., Balzquez (1998) Plant Cell 10:791-800, characterizing the Arabidopsis LEAFY gene promoter. See also Cardon (1997) Plant J 12:367-77, describing the transcription factor SPL3, which recognizes a conserved sequence motif in the promoter region of the *A. thaliana* floral meristem identity gene API; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells, in one aspect, the nucleic acids of the invention are operably linked to a promoter active primarily during the stages of cotton fiber cell elongation, e.g., as described by Rinehart (1996) supra. The nucleic acids can be operably linked to the FbI2A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60) and promoters such as those disclosed in U.S. Pat. Nos. 5,618,988, 5,837,848 and 5,905,186. Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF 13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves, a guard-cell preferential promoter e.g. as described in PCT/EP12/065608, and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells. Further tissue specific promoters that may be used according to the invention include: seed-specific promoters (such as the napin, phaseolin or DC3 promoter described in U.S. Pat. No. 5,773,697), fruit-specific promoters that are active during fruit ripening (such as the dm 1 promoter (U.S. Pat. No. 5,783,393), or the 2A1 1 promoter (e.g., see U.S. Pat. No. 4,943,674) and the tomato polygalacturonase promoter (e.g., see Bird et al. (1988) Plant Mot Biol. 11: 651-662), flower-specific promoters (e.g., see Kaiser et al. (1995) Plant Mot Biol. 28: 231-243), pollen-active promoters such as PTA29, PTA26 and PTA13 (e.g., see U.S. Pat. No. 5,792,929) and as described in e.g. Baerson et al. (1994 Plant Mol. Biol. 26: 1947-1959), promoters active in vascular tissue (e.g., see Ringli and Keller (1998) Plant Mol, Biol. 37: 977-988), carpels (e.g., see Ohl et al. (1990) Plant Cell 2), pollen and ovules (e.g., see Baerson et al. (1993) Plant Mol. Biol. 22: 255-267). In alternative embodiments, plant promoters which are inducible upon exposure to plant hormones, such as auxins, are used to express the nucleic acids used to practice the invention. For example, the invention can use the auxin-response elements E1 promoter fragment (AuxREs) in the soybean {*Glycine max* L.) (Liu (1997) Plant Physiol. 115: 397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (ABA) (Sheen (1996) Science 274:1900-1902). Further hormone inducible promoters that may be used include auxin-inducible promoters (such as that described in van der Kop et al. (1999) Plant Mol. Biol. 39: 979-990 or Baumann et al., (1999) Plant Cell 11: 323-334), cytokinin-inducible promoter (e.g., see Guevara-Garcia (1998) Plant Mol. Biol. 38: 743-753), promoters responsive to gibberellin (e.g., see Shi et al. (1998) Plant Mol. Biol. 38: 1053-1060, Willmott et al. (1998) Plant Molec. Biol. 38: 817-825) and the like.

In alternative embodiments, nucleic acids used to practice the invention can also be operably linked to plant promoters which are inducible upon exposure to chemical reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena* saliva L. (oat) arginine decarboxylase gene (Masgrau (1997) Plant J. 11:465-473); or, a salicylic acid-responsive element (Stange (1997) Plant J. 11:1315-1324). Using chemically—{e.g., hormone- or pesticide-) induced promoters, i.e., promoter responsive to a chemical which can be applied to the transgenic plant in the field, expression of a polypeptide of the invention can be induced at a particular stage of development of the plant. Use may also be made of the estrogen-inducible expression system as described in U.S. Pat. No. 6,784,340 and Zuo et al. (2000, Plant J. 24: 265-273) to drive the expression of the nucleic acids used to practice the invention.

In alternative embodiments, a promoter may be used whose host range is limited to target plant species, such as corn, rice, barley, wheat, potato or other crops, inducible at any stage of development of the crop.

In alternative embodiments, a tissue-specific plant promoter may drive expression of operably linked sequences in tissues other than the target tissue. In alternative embodiments, a tissue-specific promoter that drives expression preferentially in the target tissue or cell type, but may also lead to some expression in other tissues as well, is used.

According to the invention, use may also be made, in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, J. Virol. 64: 1590-1597, for example.

Other regulatory sequences that enhance the expression of the nucleic acid of the invention may also be located within the chimeric gene. One example of such regulatory sequences are introns. Introns are intervening sequences present in the pre-mRNA but absent in the mature RNA following excision by a precise splicing mechanism. The ability of natural introns to enhance gene expression, a process referred to as intron-mediated enhancement (IME), has been known in various organisms, including mammals, insects, nematodes and plants (WO 07/098042, p 11-12). IME is generally described as a posttranscriptional mechanism leading to increased gene expression by stabilization of the transcript. The intron is required to be positioned between the promoter and the coding sequence in the normal orientation. However, some introns have also been described to affect translation, to function as promoters or as position and orientation independent transcriptional enhancers (Chaubet-Gigot et al., 2001, Plant Mol Biol. 45(1):17-30, p 27-28).

In connection with the present invention suitable examples of genes containing such introns include the 5' introns from the rice actin 1 gene (see U.S. Pat. No. 5,641,876), the rice actin 2 gene, the maize sucrose synthase gene (Clancy and Hannah, 2002, Plant Physiol. 130(2):918-29), the maize alcohol dehydrogenase-1 (Adh-1) and Bronze-1 genes (Callis et al. 1987 Genes Dev. 1(10):1183-200; Mascarenhas et al. 1990, Plant Mol Biol. 15(6):913-20), the maize heat shock protein 70 gene (see U.S. Pat. No. 5,593,874), the maize shrunken 1 gene, the light sensitive 1 gene of *Solanum tuberosum*, and the heat shock protein 70 gene of *Petunia hybrida* (see U.S. Pat. No. 5,659,122), the replacement histone H3 gene from alfalfa (Keleman et al. 2002 Transgenic Res. 11(1):69-72) and either replacement histone H3 (histone H3.3-like) gene of *Arabidopsis thaliana* (Chaubet-Gigot et al., 2001, Plant Mol Biol. 45(1):17-30).

Other suitable regulatory sequences include 5' UTRs. As used herein, a 5'UTR, also referred to as leader sequence, is a particular region of a messenger RNA (mRNA) located between the transcription start site and the start codon of the coding region. It is involved in mRNA stability and translation efficiency. For example, the 5' untranslated leader of a *petunia* chlorophyll a/b binding protein gene downstream of the 35S transcription start site can be utilized to augment steady-state levels of reporter gene expression (Harpster et al., 1988, Mol Gen Genet. 212(1):182-90). WO95/006742 describes the use of 5' non-translated leader sequences derived from genes coding for heat shock proteins to increase transgene expression. A "3' end region involved in transcription termination and polyadenylation functional in plants" as used herein is a sequence that drives the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3'his and 3'g7.

"Introducing" in this respect, relates to the placing of genetic information in a plant cell or plant by artificial means, such as transformation. This can be effected by any method known in the art for introducing RNA or DNA into plant cells, tissues, protoplasts or whole plants. In addition to artificial introduction as described above, "introducing" also comprises introgressing genes as defined further below.

Transformation means introducing a nucleotide sequence into a plant in a manner to cause stable or transient expression of the sequence. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

In alternative embodiments, the invention uses *Agrobacterium tumefaciens* mediated transformation. Also other bacteria capable of transferring nucleic acid molecules into plant cells may be used, such as certain soil bacteria of the order of the Rhizobiales, e.g. Rhizobiaceae (e.g. *Rhizobium* spp., *Sinorhizobium* spp., *Agrobacterium* spp); Phyllobacteriaceae (e.g. *Mesorhizobium* spp., *Phyllobacterium* spp.); Brucellaceae (e.g. *Ochrobactrum* spp.); Bradyrhizobiaceae (e.g. *Bradyrhizobium* spp.), and Xanthobactcraceae (e.g. *Azorhizobium* spp.), *Agrobacterium* spp., *Rhizobium* spp., *Sinorhizobium* spp., *Mesorhizobium* spp., *Phyllobacterium* spp. *Ochrobactrum* spp. and *Bradyrhizobium* spp., examples of which include *Ochrobactrum* sp., *Rhizobium* sp., *Mesorhizobium loti*, *Sinorhizobium meliloti*. Examples of *Rhizobia* include *R. leguminosarum* by, *trifolii*, *R. leguminosarum* bv, *phaseoli* and *Rhizobium leguminosarum*, by, *viciae* (U.S. Pat. No. 7,888,552). Other bacteria that can be employed to carry out the invention which are capable of transforming plants cells and induce the incorporation of foreign DNA into the plant genome are bacteria of the genera *Azobacter* (aerobic), *Closterium* (strictly anaerobic), *Klebsiella* (optionally aerobic), and *Rhodospirillum* (anaerobic, photosynthetically active). Transfer of a Ti plasmid was also found to confer tumor inducing ability on several Rhizobiaceae members such as *Rhizobium trifolii*, *Rhizobium leguminosarum* and *Phyllobacterium myrsinacearum*, while *Rhizobium* sp. NGR234, *Sinorhizobium meliloti* and *Mesorhizobium loti* could indeed be modified to mediate gene transfer to a number of diverse plants (Broothaerts et al., 2005, Nature, 433:629-633).

In alternative embodiments, making transgenic plants or seeds comprises incorporating sequences used to practice the invention and, in one aspect (optionally), marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327: 70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In alternative embodiments, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

In alternative embodiments, a third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

Viral transformation (transduction) may also be used for transient or stable expression of a gene, depending on the nature of the virus genome. The desired genetic material is packaged into a suitable plant virus and the modified virus is allowed to infect the plant. The progeny of the infected plants is virus free and also free of the inserted gene. Suitable methods for viral transformation are described or further detailed e. g. in WO 90/12107, WO 03/052108 or WO 2005/098004.

In alternative embodiments, after the chimeric gene is stably incorporated in transgenic plants, it can be introduced into other plants by sexual crossing or introgression. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides, e.g., an HDC1 gene of the invention. The desired effects can be passed to future plant generations by standard propagation means.

Successful examples of the modification of plant characteristics by transformation with cloned sequences which serve to illustrate the current knowledge in this field of technology, and include for example: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,619,042.

In some embodiments, following transformation, plants are selected using a dominant selectable marker incorporated into the transformation vector. Such a marker can confer antibiotic or herbicide resistance on the transformed plants, and selection of transformants can be accomplished by exposing the plants to appropriate concentrations of the antibiotic or herbicide.

In some embodiments, after transformed plants are selected and grown to maturity, those plants showing a modified trait are identified. The modified trait can be any of those traits described above. In alternative embodiments, to confirm that the modified trait is due to changes in expression levels or activity of the transgenic polypeptide or nucleic acid can be determined by analyzing mRNA expression using Northern blots, RT-PCR or mieroarrays, or protein expression using immunoblots or Western blots or gel shift assays.

"Introgressing" means the integration of a gene in a plant's genome by natural means, i.e. by crossing a plant comprising the chimeric gene or mutant allele described herein with a plant not comprising said chimeric gene or mutant allele. The offspring can be selected for those comprising the chimeric gene or mutant allele.

A further embodiment provides methods according to the invention wherein said monocot plant is a cereal plant, such as a temperate cereal plant (e.g. a winter variety thereof), such as a wheat plant (e.g. a winter variety thereof).

Cereal plants, also called grain plants, include, but are not limited to, Rice (*Oryza sativa*), Wheat (*Triticum aestivum*) Durum wheat, macaroni wheat (*Triticum durum*), Corn or maize (*Zea mays*), Job's Tears, salay, tigbe, pawas (*Coix lachryma-jobi*), Barley (*Hordcum vulgare*), Millet (*Panicum miliaccum, Eleusinc coracana, Setaria italica, Pennisetum glaucum*), Sorghum (*Sorghum bicolor*), Oat (*Avcna sativa*), Rye (*Secale cereale*), Triticale (x*Triticosecalez*), Teff, taf or khak shir (*Eragrostis tef*), Fonio (*Digitaria exilis*), Wild rice, Canada rice, Indian rice, water oats (*Zizania* spp.), Spelt (*Triticum spelta*), Canary grass (*Phalaris* sp.).

Temperate cereal plants are cereal plants that grow in regions with and are well adapted to a temperate or cool climate, and include e.g. corn, barley, wheat (including spelt), rye and oats. Most varieties of a particular species are either winter or spring types. Winter varieties are sown in the autumn, germinate and grow vegetatively, then become dormant during winter. They resume growing in the springtime and mature in late spring or early summer. Winter varieties do not flower until springtime because they require vernalization: exposure to low temperature for a genetically determined length of time. Where winters are too warm for vernalization or exceed the hardiness of the crop (which varies by species and variety), farmers grow spring varieties. Spring cereals are planted in early springtime and mature later that same summer, without vernalization. Spring cereals typically require more irrigation and yield less than winter cereals. Warm climate cereals are grown in tropical lowlands year-round and in temperate climates during the frost-free season, and include for example rice and sorghum.

Wheat plants as used herein are plants of the *Triticum* ssp, such as *Triticum acstivum* and *Triticum durum* or *Triticum spelta*.

In again a further embodiment, the FLC gene comprises a nucleotide sequence having at least 80% sequence identity to any one of SEQ ID NOs: 1, 3, 5, 7, 9, 11, 13, 15 and 17 or wherein said FLC protein comprises an amino acid sequence having at least 80% sequence identity to any one of SEQ ID NOs: 2, 4, 6, 8, 10, 12, 14, 16 and 18.

As used herein, at least 80% sequence identity can be at least 80%, at least 85%, at least 90%, at least 95%, at least 98%, at least 99% or 100% sequence identity.

Further provided is a chimeric gene as described in the methods of the invention, and a plant, plant part, plant organ, plant cell or seed comprising said chimeric gene.

The invention further provides a monocot plant, plant part, plant organ, plant cell or seed, obtainable according to the methods of the invention, wherein the expression and/or activity of an FLC gene and/or protein has been altered as compared to a control plant. Also provided is a monocot plant comprising a mutant allele of an FLC gene, said mutant allele resulting in a alteration of the expression and/or activity of the FLC protein encoded by said gene compared to a plant not comprising said mutation (i. e. comprising a wild-type FLC allele) in which, optionally, the (temperature-dependent) flowering time or the seed germination has been modulated compared to said plant not comprising said mutation. Said monocot plant, plant part, plant organ, plant cell or seed can be e.g. a cereal plant, plant part, plant organ, plant cell or seed, such as a temperate cereal (e.g a winter variety) plant, plant part, plant organ, plant cell or seed, such as wheat (winter variety) plant, plant part, plant organ, plant cell or seed.

According to a further embodiment, the FLC protein comprised in the plant, plant part, plant organ or plant cell according to the invention has at least 80% sequence identity to any one of SEQ ID NOs: 2, 4, 6, 8, 10, 12, 14, 16 an 18 or wherein said FLC protein is encoded by a nucleotide sequence having at least 80% sequence identity to any one of SEQ ID NOs: 1, 3, 5, 7, 9, 11, 13, 15 and 17. In an even further embodiment, the plant according to the invention is a cereal plant, such as a temperate cereal plant, such as a wheat plant.

Further provided is a method for identifying a monocot plant, such as a cereal plant, or a temperate cereal plant, or a wheat plant, with a modulated (temperature-dependent) flowering, seed development and/or with modulated seed germination comprising the step of
  a. providing a population of monocot plants (of the same species), for example a population that has been subjected to mutagenesis,
  b. identifying one or more plants with a mutant allele of an FLC gene, such as an FLC gene having at least 80% sequence identity to any one of SEQ ID NOs: 1, 3, 5, 7, 9, 11, 13, 15 and 17, or an FLC gene encoding a protein having at least 80% sequence identity to any one of SEQ ID NOs: 2, 4, 6, 8, 10, 12, 14 and 16; and
  c. identifying within said plants with a mutant allele of an FLC gene, such as an FLC gene having at least 80% sequence identity to any one of SEQ ID NOs: 1, 3, 5, 7, 9, 11, 13, 15 and 17, or an FLC gene encoding a protein having at least 80% sequence identity to any one of SEQ ID NOs: 2, 4, 6, 8, 10, 12, 14, 16 and 18, one or more plants that have a modulated flowering time or seed germination compared to a plant of the same species not comprising said mutation.

A mutant allele of an FLC gene as used herein can be a mutant allele wherein FLC activity is increased. Alternatively, said mutant allele of an FLC gene can be a knock-out FLC allele or can result in an FLC protein with reduced activity, which can be measured as described elsewhere in this application.

In a further embodiment, an FLC protein or a functional fragment thereof is provided which is obtainable from a monocot plant, such as from a cereal plant, such as from a temperate cereal, such as a wheat plant, e.g. an FLC protein which has an amino acid sequence having at least 80% sequence identity to any one of SEQ ID NOs: 2, 4, 6, 8, 10, 12, 14, 16 and 18. Preferably, in the FLC proteins having at least 80% sequence identity, only the third nucleotide of a codon is altered.

In a further embodiment, a nucleic acid sequence encoding the FLC protein according to the invention is provided, such as a nucleic acid molecule having at least 80% sequence identity to any one of SEQ ID NOs: 1, 3, 5, 7, 9, 11, 13, 15 and 17.

A further aspect of the invention provides the use of the chimeric gene according to the invention, of the protein according to the invention, or of the nucleic acid sequence according to the invention to modulate (temperature-dependent) flowering time, seed development, seed maturation or seed germination in a monocot plant, such as a cereal plant, such as a temperate cereal plant, such as a wheat plant.

A nucleic acid or polynucleotide, as used herein, can be DNA or RNA, single- or double-stranded. Nucleic acids can be synthesized chemically or produced by biological expression in vitro or even in vivo. Nucleic acids can be chemically synthesized using appropriately protected ribonucleoside phosphoramidites and a conventional DNA/RNA synthesizer. Suppliers of RNA synthesis reagents are for example Proligo (Hamburg, Germany), Dhannacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). In connection with the chimeric gene of the present disclosure, DNA includes cDNA and genomic DNA.

The terms "protein" or "polypeptide" as used herein describe a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gal) opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined abovefurther below).

Whenever reference to a "plant" or "plants" according to the invention is made, it is understood that also plant parts cells, tissues or organs, seed pods, seeds, severed parts such as roots, leaves, flowers, pollen, etc. are included. Whenever reference to a "plant" or "plants" according to the invention is made, it is understood that also progeny of the plants which retain the distinguishing characteristics of the parents (especially modulated flowering time, seed development, seed maturation or modulated seed germination), such as seed obtained by selfing or crossing, e.g. hybrid seed (obtained by crossing two inbred parental lines), hybrid plants and plant parts derived there from are encompassed herein, such as progeny comprising a chimeric gene or mutant/knock-out FLC allele according to the invention, unless otherwise indicated.

In some embodiments, the plant cells of the invention, i.e. a plant cell in which expression of an FLC gene and/or protein is modulated, as well as plant cells generated according to the methods of the invention, may be a non-propagating plant cell or a plant cell that cannot be regenerated into a plant or a plant cell that cannot maintain its life by synthesizing carbohydrate and protein from the inorganics, such as water, carbon dioxide, and inorganic salt, through photosynthesis.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

The sequence listing contained in the file named "BCS13-2008_5 T25.txt", which is 52 kilobytes (size as measured in Microsoft Windows®), contains 27 sequences SEQ ID NO: 1 through SEQ ID NO: 27 is filed herewith by electronic submission and is incorporated by reference herein.

SEQUENCES

SEQ ID NO: 1: *Triticum aestivum* MADS2 coding sequence

SEQ ID NO: 2: *Triticum aestivum* MADS2 protein

SEQ ID NO: 3: *Triticum aestivum* TaAGL42 coding sequence

SEQ ID NO: 4: *Triticum aestivum* TaAGL42 protein

SEQ ID NO: 5: *Triticum aestivum* TaAGL41 coding sequence

SEQ ID NO: 6: *Triticum aestivum* TaAGL41 protein

SEQ ID NO: 7: *Triticum aestivum* TaAGL33 coding sequence

SEQ ID NO: 8: *Triticum aestivum* TaAGL33 protein

SEQ ID NO: 9: *Triticum aestivum* TaALG12coding sequence

SEQ ID NO: 10: *Triticum aestivum* TaALG12protein

SEQ ID NO: 11: *Triticum aestivum* TaAGL22 coding sequence

SEQ ID NO: 12: *Triticum aestivum* TaAGL22 protein

SEQ ID NO: 13: *Brachypodium distachyon* MADS37 coding sequence

SEQ ID NO: 14: *Brachypodium distachyon* MADS37 protein

SEQ ID NO: 15: *Brachypodium distachyon* ODDSOC1 coding sequence

SEQ ID NO: 16: *Brachypodium distachyon* ODDSOC1 protein

SEQ ID NO: 17: *Brachypodium distachyon* ODDSOC2 coding sequence

SEQ ID NO: 18: *Brachypodium distachyon* ODDSOC2 protein

SEQ ID NO: 19: Forward PCR primer Bradi2g59187

SEQ ID NO: 20: Reverse PCR primer Bradi2g59187

SEQ ID NO: 21: Forward PCR primer Bradi2g59120

SEQ ID NO: 22: Reverse PCR primer Bradi2g59120

SEQ ID NO: 23: Forward PCR primer Bradi3g41297

SEQ ID NO: 24: Reverse PCR primer Bradi3g41297

SEQ ID NO: 25: Forward PCR primer UBC18

SEQ ID NO: 26: Reverse PCR primer UBC18

SEQ ID NO: 27: Expression vector pIPKb002-Bd-MADS37

EXAMPLES

It has previously been suggested that the vernalization response in temperate cereals and eudicots has evolved independently (Alexandre & Bening (2008) (supra); Kim et al (2009) (supra); Hemming & Trevaskis (2011) (supra)) and does not involve FLC. It was believed that FLC genes do not exist in such plants (Alexandre & Hennig (2008) supra; Colasanti & Coneva (2009) supra, Jarillo & Pineiro (2011) Plant Sci. 181: 364-378; Yan et al (2003) supra; Yan et al (2004) supra; Yan et al (2006) supra; Cockram et al (2007) supra), and based on sequence similarity no FLC homologues could be identified in cereals (Greenup et al. 2010, supra). Here, a different, novel approach was followed to identify FLC genes in cereals, based on the observed conservation of tandem repeat arrangements in core cudicot genomes between SEP3-, SEP1-, SQUA- and FLC-like genes.

Example 1

Methods

Local Synteny

Local synteny was qualitatively determined using the genome browsers implemented in Phytozome (Goodstein et al (2012) Nucleic Acids Res. 40, D1178), PLAZA 2.5 (Van Bel et al (2012) Plant Phys. 158, 590), solgenomics (Bombarely et al (2010) Nucleic Acids Res. 39, D1149) and the Amborella Genome Project (https://www.amborella.org; funded by the National Science Foundation grant #0922742). Tandem repeats and shared syntenic markers around SEPALLATA- and *SQUAMOSA*-like genes were identified by BLAST (Basic Local Alignment Searches Tool) searches against the GenBank database.

Detecting Synteny Using i-ADHoRe

To trace ancient syntenic relationships, a novel approach was adopted. Clustering an all-against-all blast using relaxed settings generated crude gene families. Using i-ADHoRe 3.0 in hybrid mode (Proost et al (2012) Nucleic Acids Res. 40, ell), the grapevine genome was scanned for significant colinear and syntenic regions. In this mode first colinear regions are detected and hidden from the dataset and in a next step the remaining fraction of the genome is scanned for additional syntenic regions.

First, a dataset was composed consisting of all angiosperm proteins from PLAZA 2.5 (Van Bel et al (2012) (supra)), combined with proteins of more recently sequenced species, *Brassica rapa* (Wang et al (2011) Nat. Genet. 43, 1035), tomato (The Tomato Genome Consortium (2012) Nature 485, 635) and potato (The Potato Genome Sequencing Consortium (2011) Nature 475, 189). Additionally the *Vitis vinifera* annotation was downloaded from PLAZA 2.5 and converted to input for i-ADHoRe 3.0 (Proost et al (2012) Nucleic Acids Res. 40, ell). An all-against-all blastp was run (version 2.2.27+ using default settings) (Altschul et al (1997) Nucleic Acids Res. 25, 3389) to determine pairwise similarities between all proteins in the dataset. Using tribe-MCL (Enright et al (2002) Nucleic Acids Res. 30, 1575) the blast output was clustered into homologous gene families (settings: blast-m9, blast-ecut=le-03, blast-score=e, mc1-I=1.2 and mc1-scheme=4).

For the detection of significant synteny, i-ADHoRe 3.0 was used in hybrid mode, where first colinear regions are detected and removed and in the remainder of the gene homology matrices syntenic regions are detected. (cluster_type=hybrid, cloud_gap_size=10, cloud_cluster_gap=15, cloud_filter_method=binomial_corr, gap_size=30, cluster_gap=35, q_value=0.75, alignment_method=gg2, level_2_only=false, prob_cut-off=0.001, anchor_points=3 and multiple_hypothesis_correction=FDR). A less stringent run was performed with a prob_cutoff of 0.05, cloud_gap_size=20 and cloud_cluster_gap=25.

Detection of Markers (without Synteny)

*Vitis* MADS box genes were extracted together with 40 protein-coding genes up- and downstream and stored as a list per gene. Redundancy due to tandems was removed and the remaining lists were screened for marker genes that could be used to provide additional insight in the origin of the SEP3-FLC, SEP1-SQUA and AGL6-SOC1 tandem arrangements. Here valid markers are sets of at least three homologous genes, which occur in proximity of all three classes MADS-box genes.

Taxon Sampling, Multiple Sequence Alignment and Phylogenetic Analyses.

We performed BLAST searches using core eudicot FLC sequences represented in a published FLC phylogeny (Reeves et al (2007) Genetics 176, 295) against the GenBank, TIGR (The Institute for Genomic Research) and AAGP (Ancestral Angiosperm Genome Project) databases to retrieve additional core eudicot FLC-like genes. Based on the observation of conserved tandem repeat arrangements in core eudicot genomes between SEP3-, SEP1-, SQUA- and FLC-like genes, we found OsMADS37 as a candidate FLC-like sequence in rice. This sequence was used in BLASTN searches to identify similar sequences present in the Genbank database and all sequences retrieved were included in a data matrix for phylogenetic analysis. In addition, we putatively identified the ODDSOC2 clade from the Barley (*Hordeum*) EST collection through weaker similarity with OsMADS37. Using BLAST searches similar sequences were included in further analyses. We attempted to comprehensively sample all major subfamilies of MIKCc-type MADS-box genes (Becker & Theissen (2003) Mol. Phylogenet. Evol. 29, 464) to investigate the evolutionary affinities of the sequences found. These subfamilies were consistently represented by sequences of at least one asterid, rosid, magnoliophyte, monocot and gymnosperm when available. Finally, known charophyte, moss and fern MIKCc-type MADS-box genes were included. Using the above sampling rationale we obtained a nucleotide data-matrix consisting of 254 sequences, which was aligned using MAFFT v6 (Katoh & Toh (2008) BMC Bioinformatics 9, 212) and manually refined using MacClade4 (Maddison & Maddison (2003) MacClade 4: Analysis of phylogeny and character evolution. (Sinauer Associates, Massachusetts, USA) 4.06).

C-terminal sequences could not be unambiguously aligned and were therefore excluded from the alignment. In addition, several gene specific insertions were also removed which resulted in a final alignment of 528 bp. The jModeltest program (Posada (2008) Mol. Biol. Evol. 25, 1253) was used to determine the best-fit model of nucleotide substitution according to the Akaike information criterion, which selected the GTR+I+G evolutionary model.

The maximum-likelihood phylogenetic analysis was performed using PhyML 3.0 (Guindon et al (2010) Syst. Biol. 59, 307). Bootstrap values summarize 100 bootstrap replicates. Bayesian analysis was carried out using MrBayes 3.2 (Ronquist & Huelsenbeck (2003) Bioinfonnatics 19, 1572). Two independent runs with each 4 Markov Chain Monte Carlo chains were run for 15,000,000 generations and sampled every 1,000 generations. After convergence indicated by a standard deviation of split frequencies <0.02, we removed the first 25% of the sampled trees as burn-in. The posterior distribution over trees is presented as a majority-rule consensus tree and posterior probabilities are indicated at their respective nodes. Both trees were rooted using charophyte MIKCc type MADS-box genes.

qRT-PCR Quantification of FLC-like Genes in *Brachypodium*

*Brachypodium distachyon* plants were grown in pots containing 50:50 soil:vermiculite. Plantlets were pre-grown under long-days (16 h light-8 h dark; 54 photons μmol m-2 s-1) at 28° C. until the third leaf fully emerged. These "three-leaf" plantlets were subsequently transferred to another growth chamber at 4° C. (vernalization treatment) or 28° C. (control) (16 h light-8 h dark; 20 photons μmol m-2 s-1) during 6 weeks and plants were harvested pre-vernalization and at 2, 4, and 6 weeks. Immediately after harvesting, samples were flash frozen in liquid nitrogen. RNA was extracted from whole plants with their root removed using Trizol (Invitrogen, Carlsbad, US). Subsequently all RNA samples were DNase treated using TURBO DNA-free (Ambion, Austin, US). cDNA was prepared by reverse transcription using AMV reverse transcriptase (Promcga, Madison, US). qRT-PCR was performed on a StepOne Plus apparatus (Applied Biosystems, Forster City, US) using Fast SYBR Green Master Mix (Applied Biosystems, Forster City, US). The ubiquitin-conjugating enzyme 18 gene (UBC18; Bradi4g00660) was used as a reference gene to normalize the samples (Hong et al (2008) BMC plant biology, 8, 112). Relative gene expression change was calculated using the delta-delta Ct method. Error bars represent the standard error of three biological replicates, which are the mean of three technical replicates. The following primers were used for qRT-PCR: Bradi2g59187 (F: 5'-AAATCCAAGATATTG-GCAAAACG-3' (SEQ ID NO: 19), R: 5'-CCTTAGGCT-CACTGGAGTTCTCA-3' (SEQ ID NO: 20), Bradi2g59120 (F: 5'-CCGGCAAGCTCTACGAGTACTC-3'(SEQ ID NO: 21), R: 5'-GCTCCCGCAAATTGCTGAT-3' (SEQ ID NO: 22), Bradi3g41297 (F: 5'-CAATCTGAGGATGAAGGTGT-CACA-3' (SEQ ID NO: 23), R: 5'-GCTTGACAAGTTGT-TCGCTTTCT-3' (SEQ ID NO: 24)) and UBC18 (F: 5'-GTC-GACTTCCCCGAGCATTA-3' (SEQ ID NO: 25), R: 5'-ATAGGCGCCGGGTTGAG-3' (SEQ ID NO: 26)).

Example 2

FLOWERING LOCUS C Orthologs are Present in Monocots

The conservation of gene order between species and between duplicated genomic segments can provide insights into the evolutionary history of genes. Such information can complement phylogenies as an independent source of evidence for evolutionary relationships between paralogous (duplicated) gene lineages (Tang et al (2010) Proc. Natl. Acad. Sci. USA 107, 472), including MADS-box genes (Causicr et al (2010) Mol. Biol. Evol. 27, 2651). Therefore, we studied genomic locations of MIKC-type MADS-box genes in phylogenetically informative flowering plant genomes. To this end, we identified evolutionary conserved tandem arrangements for members of different MADS-box gene subfamilies. We observed that members of the SEP1 and SQUA as well as SEP3 and FLC subfamilies are arranged in tandem in several core eudicot genomes (FIG. 1). While members of the SQUA subfamily are exclusively next to members of the SEP1 subclade, FLC genes are consistently next to members of the SEP3 subclade.

Figure 2:
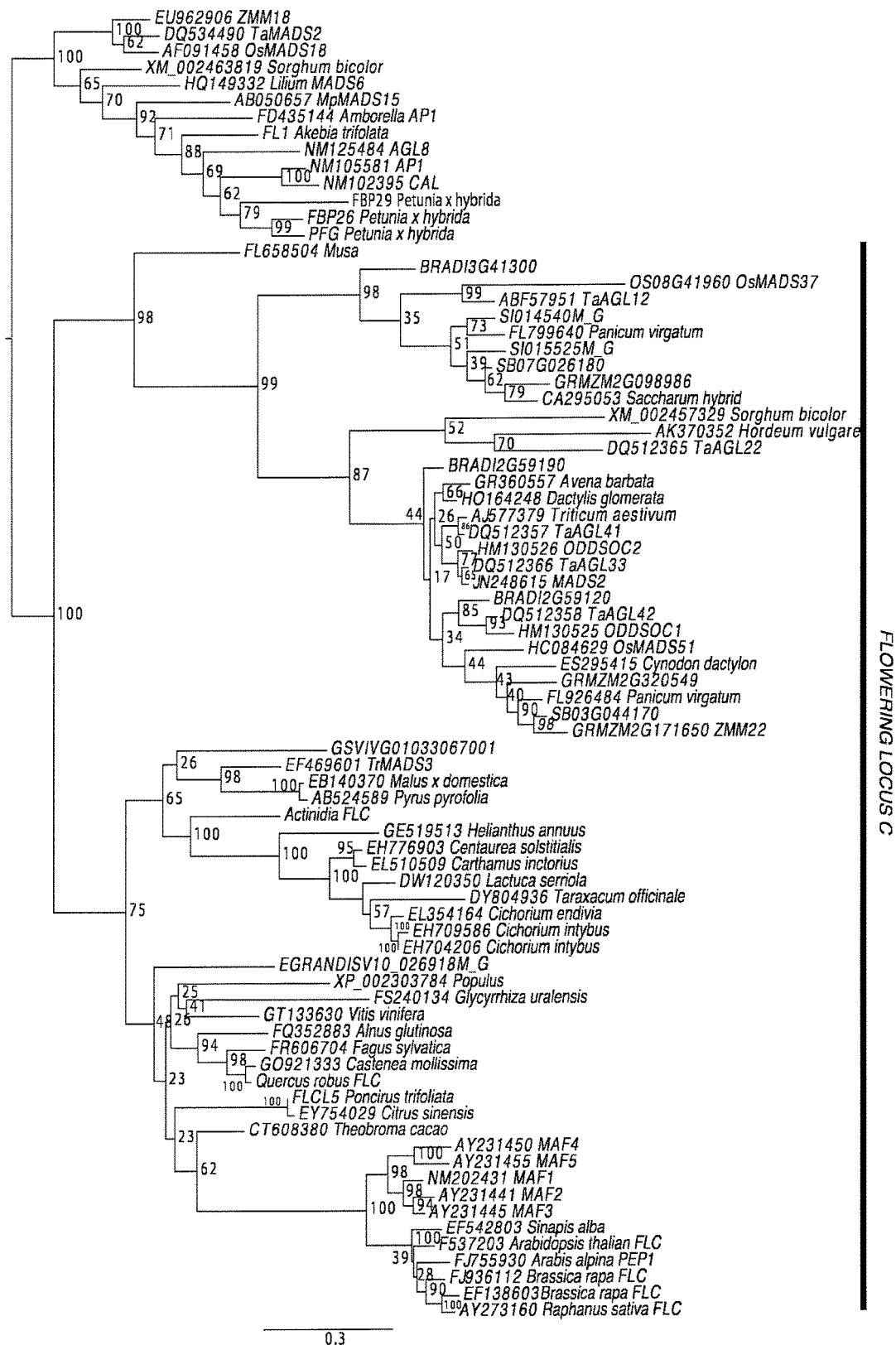
FIG. 2: Maximum likelihood tree of FLC-like genes with *SQUAMOSA*-like as a root. The numbers next to each node indicate bootstrap support values of 100 non-parametric bootstraps. Phylogenetic analysis was performed with PhyML 3.0.

SQUA and SEP1 tandem arrangements can also be identified in monocot genomes (FIG. 1.). Interestingly, in monocots we identified tandems of SEP3 with MADS-box genes that are currently annotated as 'monocot-specific' and being related to type I or MIKC*-type MADS-box genes (Kim et al (2007) Plant Physiol. 145, 1484; Arora et al. (2007) BMC Genomics 8, 242) which are evolutionarily more ancient and structurally different lineages of MADS-box genes. The genomic position of these genes, however, suggests that they represent members of the FLC subfamily in monocots. Indeed, in the phylogeny these enigmatic monocot genes group with FLC genes from core eudicots with high bootstrap support (99 BS, 1.00 BPP, FIG. 2). This indicates that these genes were previously misclassified FLC orthologs in monocots. The FLC monocot clade itself is strongly supported (100 BS, 1.00 BPP) and consists solely of genes from Poaceae, except for MpFLC (*Musa paradisiaca*, Musaceae). In the order Poales, we identified two major FLC clades, which we will refer to as OsMADS37-like genes and OsMADS51-like genes. The fact that both rice and sorghum have duplicate FLC copies could be explained by the putative whole-genome duplication 56-72 million years ago (mya) termed "rho", which occurred prior to the divergence of the major grass lineages (Tang et al (2010) Proc. Natl. Acad. Sci. USA 107, 472; Initiative IBG (2010) Nature 463, 763). Subsequently, one of these lineages underwent a tandem duplication, apparently prior to the origin of Pooideae. These monocot-specific duplications resulted in three FLC clades in temperate grasses and two major lineages in the order Poales (Greenup et al. (2010) Plant Physiol. 153, 1062). The monocot FLC genes are characterized by divergent, short protein sequences, which probably made it difficult to identify them through traditional similarity searches, such as BLAST (Reeves et al (2007) Genetics 176, 295).

The coding sequence of the *Triticum aestivum* FLC gene MADS2 is given in SEQ ID NO: 1, and the encoded protein in SEQ ID NO: 2. The coding sequence of the *Triticum aestivum* FLC gene TaAGL42 is given in SEQ ID NO: 3, and the encoded protein in SEQ ID NO: 4. The coding sequence of the *Triticum aestivum* FLC gene TaAGL41 is given in SEQ ID NO: 5, and the encoded protein in SEQ ID NO: 6. The coding sequence of the *Triticum aestivum* FLC gene TaAGL33 is given in SEQ ID NO: 7, and the encoded protein in SEQ ID NO: 8. The coding sequence of the *Triticum aestivum* FLC gene TaAGL12 is given in SEQ ID NO: 9, and the encoded protein in SEQ ID NO: 10. The coding sequence of the *Triticum aestivum* FLC gene TaAGL22 is given in SEQ ID NO: 11, and the encoded protein in SEQ ID NO: 12. The coding sequence of the *Brachypodium distachyon* FLC gene MADS37 is given in SEQ ID NO: 134. The coding sequence of the *Brachypodium distachyon* FLC gene ODDSOC1 is given in SEQ ID NO: 15, and the encoded protein in SEQ ID NO: 16. The coding sequence of the *Brachypodium distachyon* FLC gene ODDSOC2 is given in SEQ ID NO: 17, and the encoded protein in SEQ ID NO: 18. FLC genes from other monocot species in the same clade and their accession numbers are incidated in table 1.

TABLE 1

FLC genes from monocot species and their accession number.

| Species | Gene name | Identifier |
| --- | --- | --- |
| Triticum aestivum | MADS2 | JN248615 |
| Triticum aestivum | TaAGL33 | DQ512366.1 |
| Triticum aestivum | TaAGL41 | DQ512357 |
| Triticum aestivum | TaAGL42 | DQ512358.1 |
| Triticum aestivum | TaAGL12 | AB007505.1 |
| Triticum aestivum | TaAGL22 | DQ512365.1 |
| Avena barbata | AbFLC | GR360557 |
| Hordeum vulgare | HvODDSOC2 | HM130526.1 |
| Dactylis glomerata | DgFLC | HO164248 |
| Hordeum vulgare | HvODDSOC1 | HM130525 |
| Brachypodium distachyon | Bradi2g59120 | Bradi2g59120 |
| Brachypodium distachyon | Bradi3g41300 | Bradi3g41300 |
| Brachypodium distachyon | Bradi2g59190 | Bradi2g59190 |
| Oryza sativa | OsMADS512 | HC084629 |
| Oryza sativa | OSsMADS37 | Os08g41960 |
| Sorghum bicolor | SbFLC2 | Sb03g044170 |
| Sorghum bicolor | SbFLC1 | Sb07g026180 |
| Panicum virgatum | PvFLC2 | FL926484.1 |
| Panicum virgatum | PvFLC1 | FL799640 |
| Cynodon dactylon | CdFLC | ES295415.1 |
| Setaria italica | Si014540m | Si014540m |
| Saccharum hybrid | ShFLC | CA295053 |
| Zea mays | ZmMADS77 | GRMZM2G098986 |

TABLE 1-continued

FLC genes from monocot species and their accession number.

| Species | Gene name | Identifier |
|---|---|---|
| Zea mays | ZmMADS54 | GRMZM2G320549 |
| Zea mays | ZMM22 | GRMZM2G052045 |
| Musa paradisiaca | MpFLC | FL658504 |

Figure 3:
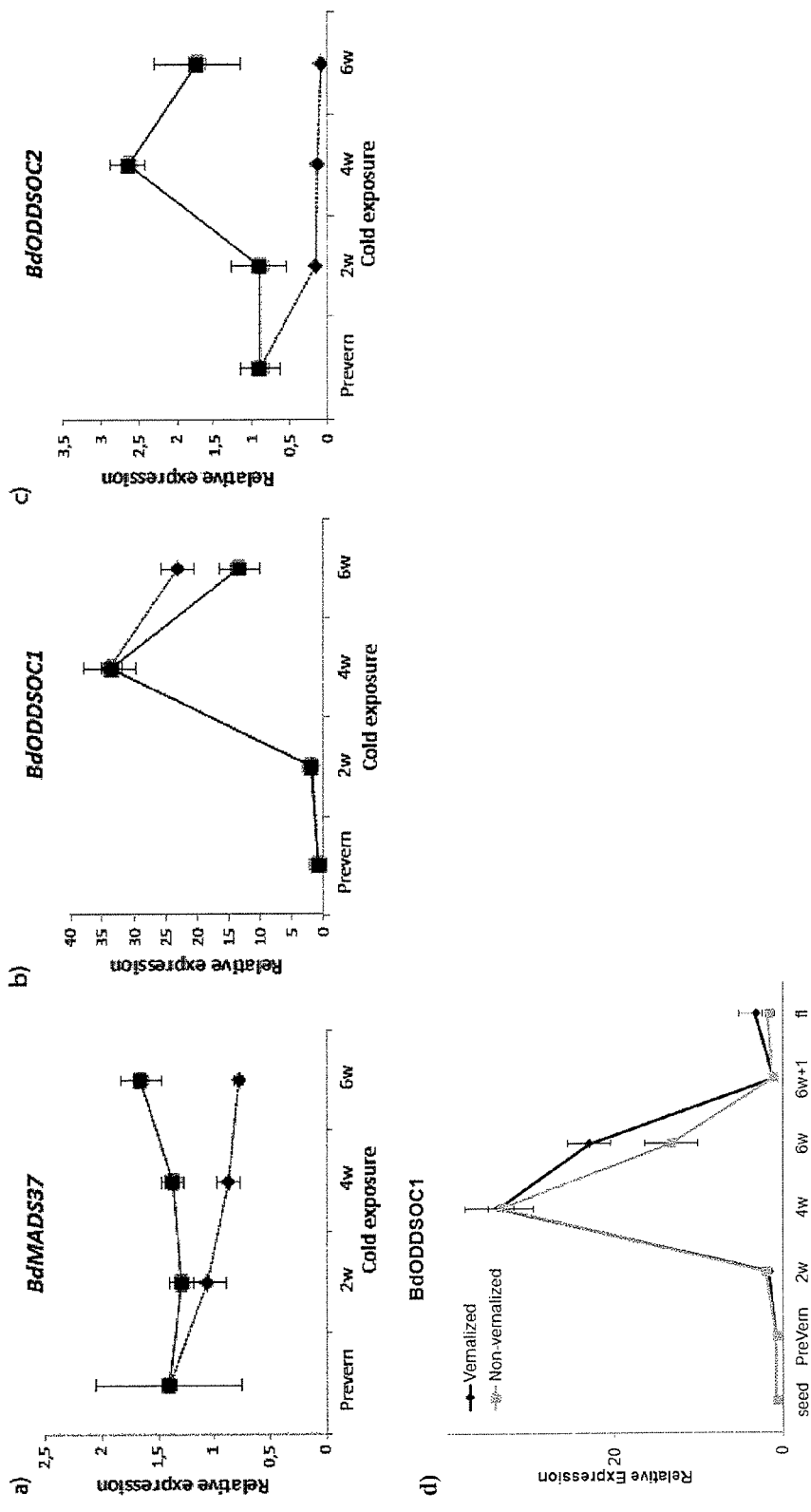
FIG. 3: Expression of *Brachypodium distachyon* FLC homologs, BdMADS37 (a), BdODDSOC1 (b) and (d) and BdODDSOC2 (c), in response to prolonged cold. Expression of FLC-like genes in *Brachypodium* were monitored using qRT-PCR in plants exposed to a 6 week period at 4° C. (vernalized) or 28° C. (control). Expression in vernalized samples is represented by diamonds, while the control samples are indicated by squares. (Abbr: Prevern: pre-vernalization, 2 w: two weeks, 4 w: four weeks, 6 w: six weeks). Error bars represent the standard errors of the mean of three biological replicates.
Figure 4:
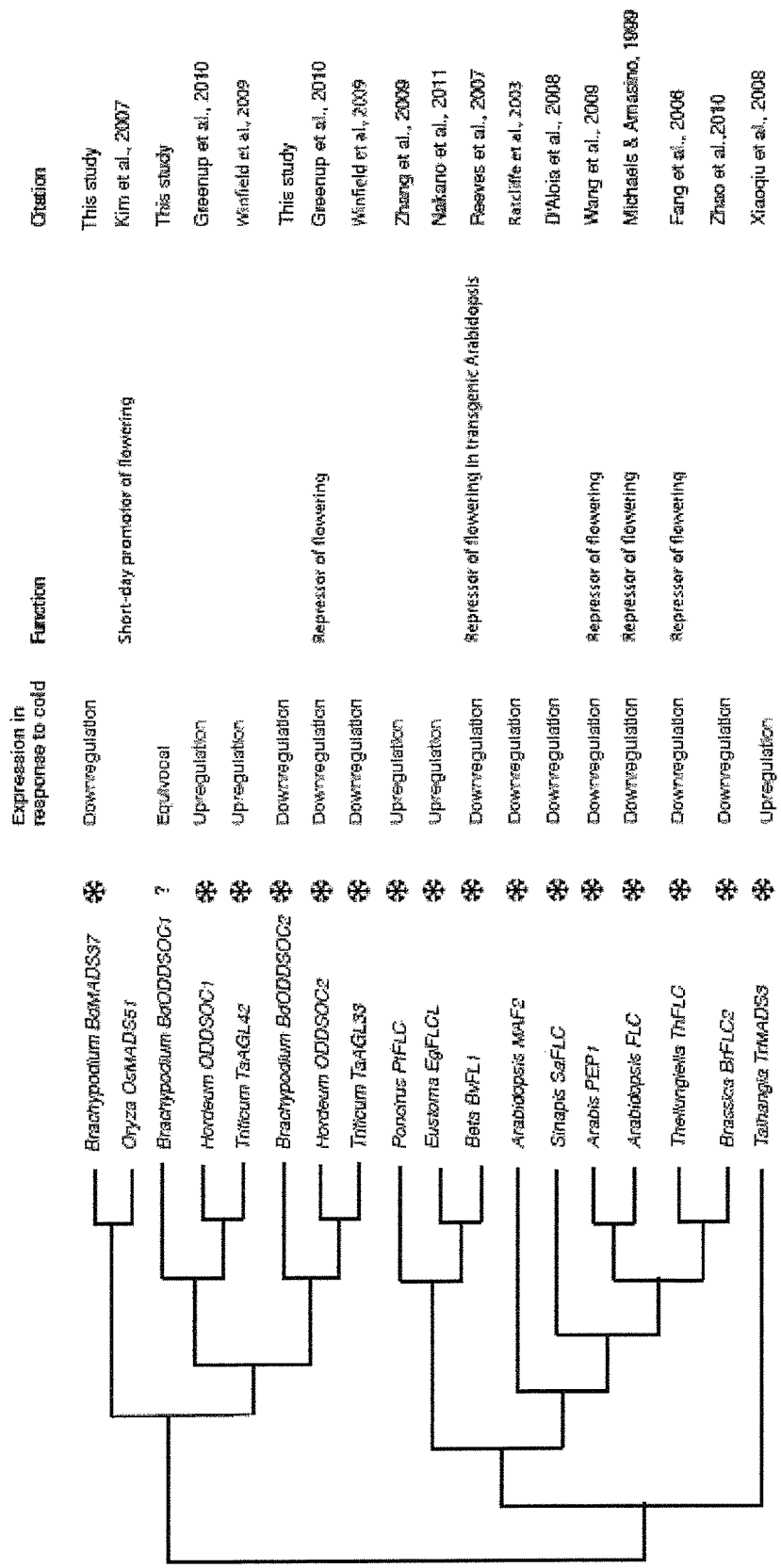
FIG. 4: Expression data and functional evidence of FLC-like genes summarized and plotted onto a simplified FLC phylogeny. Vernalization responsive genes are indicated by * next to the respective gene. (Phylogeny based on our maximum likelihood phylogeny of MIKCc-type MADS-box genes).

In recent studies, several members of the OsMADS51 clade have been shown to function in vernalization controlled flowering in temperate grasses similar to FLC-like genes in core-eudicots (FIG. 4) (Greenup et al. (2010) Plant Physiol. 153, 1062; Winfield et al (2009) BMC Plant Biol. 9, 55; WO2006/068432). To our knowledge, no members of the OsMADS37 clade have previously been investigated. To understand the cold regulation of the different FLC paralogs in more detail, we monitored their expression level in the temperate grass model Brachypodium distachyon after 2, 4 and 6 weeks of prolonged cold (4° C.) using qRT-PCR. The expression of BdMADS37 (Bradi3g41297, previously annotated as Bradi3g41300) decreases gradually during vernalization (FIG. 3a). The expression of the OsMADS51-like gene BdODDSOC2 (Bradi2g59187, previously annotated as Bradi2g59190) is more rapidly downregulated by vernalization and a minimal expression level is reached already after 2 weeks of cold, or possibly sooner, and remained stable in subsequent weeks (FIG. 3c). The expression of BdODDSOC1 (Bradi2g59120) does not appear responsive to a vernalization treatment (FIGS. 3b and 3d). In conclusion, Brachypodium FLC-like paralogs are responsive to prolonged cold exposure, but the nature of the response differs both qualitatively and quantitatively between paralogs.

The origin and functional diversification of developmental control genes is thought to be a major prerequisite for the evolution of complex morphologies in eukaryotes. We elucidated the origin of the FLC MADS-box gene subfamily. This subfamily has essential roles in floral transition and flower development: where FLC genes have mainly been shown to act as vernalization-responsive floral repressors in eudicots.

The concept of vernalization originates from the early observation that winter varieties of cereals require prolonged cold to flower, while spring varieties flower soon after sowing (Chouard (1960) Annu. Rev. Plant Physiol. 11, 191). Using a combined approach of synteny and phylogeny reconstruction, we were able to unambiguously identify FLC-like genes in monocots. This opens the possibility of translating the findings for FLC in Arabidopsis to cereal crops. The absence of FLC genes in monocots has previously been used as a major argument to claim an independent origin of vernalization response in these taxa (Chouard (1960) Annu. Rev. Plant Physiol. 11, 191; Alexandre & Hennig (2008) J. Exp. Bot. 59, 1127; Kim et al (2009) Annu. Rev. Cell Dev. Biol. 25, 277).

The results of functional analyses of some members of the OsMADS51 clade (FIG. 4), and also our expression data, indicate that members of the FLC subfamily are controlled by vernalization in temperate grasses, similar to FLC in Arabidopsis. Some aspects of FLC regulation and functions may thus be conserved throughout angiosperms. Even more intriguingly, some members of the SQUA subfamily, which is sister to FLC, are also regulated by vernalization, although in a positive manner. Examples include VERNALIZATION1 (VRN1) in the vernalization-sensitive grass species Triticum aestivum (Kim et al (2009) Annu. Rev. Cell Dev. Biol. 25, 277; Yan et al (2003) Proc. Natl. Acad. Sci. USA 100, 6263) or APETALA1 and FRUITFULL in Arabidopsis thaliana whose transcript levels change in response to cold (Hannah et al (2005) PLoS Genet 1, e26). However, since also members of other MADS-box gene subfamilies, such as STMADS11-like genes in grasses (Kane et al. (2005) Plant Physiology, 138, 2354), are controlled by vernalization, this type of temperature-dependent regulation may have evolved multiple times independently.

Example 3

Modulating Expression of FLOWERING LOCUS C Modulates Flowering Time and Seed Germination in Brachypodium Distachion and in Wheat BdMADS37, BdODDSOC1 and BdODDSOC2 (full length or fragments) are cloned into a vector for overexpression, and are cloned in a vector for downregulation (sense and/or antisense) of the endogenous BdMADS37, BdODDSOC1 and BdODDSOC2 genes. Brachypodium distachion or wheat is transformed with the vectors and flowering time and seed germination is evaluated under various temperatures and time periods.

When BdMADS37 (SEQ ID NO: 27), BdODDSOC1 or BdODDSOC2 are overexpressed in Brachypodium or wheat, flowering time is delayed, and seed germination is accelerated. When BdMADS37, BdODDSOC1 or BdODDSOC2 are downregulated, flowering time is accelerated and seed germination is delayed.

TaAGL12, TaAGL42, TaAGL41, TaAGL33, TaAGL22 and MADS2 (full length or fragments) are cloned into a vector for overexpression, and are cloned in a vector for downregulation (sense and/or antisense) of the endogenous TaAGL12, TaAGL42, TaAGL41, TaAGL33, TaAGL22 and MADS2 genes. Wheat or Brachypodium is transformed with the vectors and flowering time and seed germination is evaluated under various temperatures and time periods.

When TaAGL42, TaAGL41, TaAGL33, TaAGL22 or MADS2 are overexpressed in Brachypodium or wheat, flowering time is delayed, and seed germination is accelerated. When TaAGL42, TaAGL41, TaAGL33, TaAGL22, or MADS2 are downregulated, flowering time is accelerated and seed germination is delayed.

The invention claimed is:

1. A method for accelerating temperature dependent flowering in a monocot plant comprising introducing a nucleic acid molecule into said plant and decreasing the expression and/or activity of an Flowering Locus C (FLC) gene and/or FLC protein in said plant or plant part, plant organ or plant cell of said plant, wherein the coding sequence of said FLC gene comprises a nucleotide sequence having at least 90% sequence identity to any one of SEQ ID NOs: 1, 7 or 17, or wherein said FLC protein comprises an amino acid sequence having at least 90% sequence identity to any one of SEQ ID NOs: 2, 8 or 18, wherein accelerated flowering in said monocot plant is compared to flowering of a control plant wherein said expression and/or activity of said FLC gene or said FLC protein has not been decreased.

2. The method according to claim 1, wherein said decreasing the expression of and/or activity of an FLC gene and/or protein comprises expressing in said plant, plant part, plant organ or plant cell a chimeric gene comprising the following operably linked elements:

i) a plant-expressible promoter, ii) a nucleic acid which when transcribed results in a decreased expression and/or activity of an endogenous FLC gene and/or protein in said monocot plant, plant part, plant organ or plant cell, and iii) optionally, a 3' end region involved in transcription termination and polyadenylation functional in plants.

3. The method according to claim 1, wherein said monocot plant is a cereal plant.

4. The method according to claim 3, wherein said cereal plant is a temperate cereal plant.

5. The method according to claim 1, wherein said monocot plant is corn, barley, wheat, spelt, rye, or oats.

6. The method according to claim 1, wherein said monocot plant is wheat.

7. The method according to claim 1, wherein said monocot plant is a winter variety of wheat or barley.

8. The method according to claim 1, wherein said FLC gene comprises a nucleotide sequence having at least 95% sequence identity to any one of SEQ ID NOs: 1, 7 or 17, or wherein said FLC protein comprises an amino acid sequence having at least 95% sequence identity to any one of SEQ ID NOs: 2, 8 or 18.

9. The method according to claim 8, wherein said monocot plant is selected from corn, barley, wheat, spelt, rye, or oats.

10. The method according to claim 8, wherein said monocot plant is wheat.

11. The method according to claim 8, wherein said monocot plant is a winter variety of wheat or barley.

12. The method according to claim 1, wherein said FLC gene comprises a nucleotide sequence of any one of SEQ ID NOs: 1, 7 or 17, or wherein said FLC protein comprises an amino acid sequence of any one of SEQ ID NOs: 2, 8 or 18.

* * * * *

SEQUENCE LISTING

```
<160> NUMBER OF SEQ ID NOS: 27

<210> SEQ ID NO 1
<211> LENGTH: 471
<212> TYPE: DNA
<213> ORGANISM: Triticum aestivum
<220> FEATURE:
```

```
<221> NAME/KEY: CDS
<222> LOCATION: (1)..(471)

<400> SEQUENCE: 1 cgg cgc ggg cgt gtg gag ctg cgg cgg atc gag gac cgg acg agc cgg      48
Arg Arg Gly Arg Val Glu Leu Arg Arg Ile Glu Asp Arg Thr Ser Arg
1               5                   10                  15 cag gtg cgc ttc tcc aag cgc cgc gcg ggg ctc ttc aag aag gcc ttc      96
Gln Val Arg Phe Ser Lys Arg Arg Ala Gly Leu Phe Lys Lys Ala Phe
            20                  25                  30 gag ctc gcg gtc ctc tgc gac gcc gag gtc tcg ctg ctc gtc ttc tcc     144
Glu Leu Ala Val Leu Cys Asp Ala Glu Val Ser Leu Leu Val Phe Ser
        35                  40                  45 ccc gcc ggc agg ctc tac gag tac gcc tcc tcc agc ata gaa ggt aca     192
Pro Ala Gly Arg Leu Tyr Glu Tyr Ala Ser Ser Ser Ile Glu Gly Thr
    50                  55                  60 tat gac cgc tat cag gca ttt gca gga gcc gga aag gac gtg aat gaa     240
Tyr Asp Arg Tyr Gln Ala Phe Ala Gly Ala Gly Lys Asp Val Asn Glu
65                  70                  75                  80 ccc ggt gca agt aac aac aat gat gga gat cct tca aat ata cag tca     288
Pro Gly Ala Ser Asn Asn Asn Asp Gly Asp Pro Ser Asn Ile Gln Ser
                85                  90                  95 agg ctt gaa gag att act tcc tgg tct ctt caa aac aat gct gat aac     336
Arg Leu Glu Glu Ile Thr Ser Trp Ser Leu Gln Asn Asn Ala Asp Asn
            100                 105                 110 tca gat gct aat gag cta gag aaa ctg gag aaa cta ctg aca gat gct     384
Ser Asp Ala Asn Glu Leu Glu Lys Leu Glu Lys Leu Leu Thr Asp Ala
        115                 120                 125 ttg aag aat aca aaa tcc aag aag atg ttg gcg caa caa aat agc gat     432
Leu Lys Asn Thr Lys Ser Lys Lys Met Leu Ala Gln Gln Asn Ser Asp
    130                 135                 140 gcc ggc act agt gcg agc ggc ggg aac tcc aga agg act                 471
Ala Gly Thr Ser Ala Ser Gly Gly Asn Ser Arg Arg Thr
145                 150                 155

<210> SEQ ID NO 2
<211> LENGTH: 157
<212> TYPE: PRT
<213> ORGANISM: Triticum aestivum

<400> SEQUENCE: 2

Arg Arg Gly Arg Val Glu Leu Arg Arg Ile Glu Asp Arg Thr Ser Arg
1               5                   10                  15

Gln Val Arg Phe Ser Lys Arg Arg Ala Gly Leu Phe Lys Lys Ala Phe
            20                  25                  30

Glu Leu Ala Val Leu Cys Asp Ala Glu Val Ser Leu Leu Val Phe Ser
        35                  40                  45

Pro Ala Gly Arg Leu Tyr Glu Tyr Ala Ser Ser Ser Ile Glu Gly Thr
    50                  55                  60

Tyr Asp Arg Tyr Gln Ala Phe Ala Gly Ala Gly Lys Asp Val Asn Glu
65                  70                  75                  80

Pro Gly Ala Ser Asn Asn Asn Asp Gly Asp Pro Ser Asn Ile Gln Ser
                85                  90                  95

Arg Leu Glu Glu Ile Thr Ser Trp Ser Leu Gln Asn Asn Ala Asp Asn
            100                 105                 110

Ser Asp Ala Asn Glu Leu Glu Lys Leu Glu Lys Leu Leu Thr Asp Ala
        115                 120                 125

Leu Lys Asn Thr Lys Ser Lys Lys Met Leu Ala Gln Gln Asn Ser Asp
    130                 135                 140
```

Ala Gly Thr Ser Ala Ser Gly Gly Asn Ser Arg Arg Thr
145                 150                 155

<210> SEQ ID NO 3
<211> LENGTH: 492
<212> TYPE: DNA
<213> ORGANISM: Triticum aestivum
<220> FEATURE:
<221> NAME/KEY: CDS
<222> LOCATION: (1)..(492)

<400> SEQUENCE: 3

| cgg cgc ggg cgg gtt gag ctg cgg cgg atc gag gac cgg acg agc cgg | 48 |
|---|---|
| Arg Arg Gly Arg Val Glu Leu Arg Arg Ile Glu Asp Arg Thr Ser Arg | |
| 1               5                   10                  15      | |

| cag gtg cgc tcc tcc aag cgc gac gcg ggc ctc ttc aag aag gcc ttc | 96 |
|---|---|
| Gln Val Arg Ser Ser Lys Arg Arg Ala Gly Leu Phe Lys Lys Ala Phe | |
|               20                  25                  30       | |

| gag ctc tcg ctc ctc tgc gac gcc gag gtc gcg ctc ctc gtc ttc tcc | 144 |
|---|---|
| Glu Leu Ser Leu Leu Cys Asp Ala Glu Val Ala Leu Leu Val Phe Ser | |
|           35                  40                  45           | |

| ccc gcc ggc aag ctc tac gag tac gcc tcc tcc agc att gaa ggt aca | 192 |
|---|---|
| Pro Ala Gly Lys Leu Tyr Glu Tyr Ala Ser Ser Ser Ile Glu Gly Thr | |
| 50                  55                  60                     | |

| tat gac cgg tat cag caa ttt gcg gtg ccc gga agg aat ctg att caa | 240 |
|---|---|
| Tyr Asp Arg Tyr Gln Gln Phe Ala Val Pro Gly Arg Asn Leu Ile Gln | |
| 65              70                  75                  80     | |

| gaa gat gca act gtc tgc aat gat gaa gat cct tca aat atg cag tca | 288 |
|---|---|
| Glu Asp Ala Thr Val Cys Asn Asp Glu Asp Pro Ser Asn Met Gln Ser | |
|                 85                  90                  95     | |

| agg ctt ggc ggg att gct gcc tgg tct ctc gat aat aat gct gac aac | 336 |
|---|---|
| Arg Leu Gly Gly Ile Ala Ala Trp Ser Leu Asp Asn Asn Ala Asp Asn | |
|             100                 105                 110        | |

| tca gat gcc agt agt ttg gag aaa ctg gag aaa cta cta aag gat gct | 384 |
|---|---|
| Ser Asp Ala Ser Ser Leu Glu Lys Leu Glu Lys Leu Leu Lys Asp Ala | |
|         115                 120                 125            | |

| ctg aga att aca gaa tct aag aag gct ttg gcg aaa caa aat agt ggc | 432 |
|---|---|
| Leu Arg Ile Thr Glu Ser Lys Lys Ala Leu Ala Lys Gln Asn Ser Gly | |
| 130                 135                 140                    | |

| ggg agc acg agc gga gag agc ccc aac gga cct acg ggg cag gag aat | 480 |
|---|---|
| Gly Ser Thr Ser Gly Glu Ser Pro Asn Gly Pro Thr Gly Gln Glu Asn | |
| 145                 150                 155                 160| |

| ggg agg aat gct | 492 |
|---|---|
| Gly Arg Asn Ala | |

<210> SEQ ID NO 4
<211> LENGTH: 164
<212> TYPE: PRT
<213> ORGANISM: Triticum aestivum

<400> SEQUENCE: 4

Arg Arg Gly Arg Val Glu Leu Arg Arg Ile Glu Asp Arg Thr Ser Arg
1               5                   10                  15

Gln Val Arg Ser Ser Lys Arg Arg Ala Gly Leu Phe Lys Lys Ala Phe
            20                  25                  30

Glu Leu Ser Leu Leu Cys Asp Ala Glu Val Ala Leu Leu Val Phe Ser
        35                  40                  45

Pro Ala Gly Lys Leu Tyr Glu Tyr Ala Ser Ser Ser Ile Glu Gly Thr
50                  55                  60

Tyr Asp Arg Tyr Gln Gln Phe Ala Val Pro Gly Arg Asn Leu Ile Gln

```
                65                  70                  75                  80
Glu Asp Ala Thr Val Cys Asn Asp Glu Asp Pro Ser Asn Met Gln Ser
                    85                  90                  95

Arg Leu Gly Gly Ile Ala Ala Trp Ser Leu Asp Asn Asn Ala Asp Asn
                100                 105                 110

Ser Asp Ala Ser Ser Leu Glu Lys Leu Glu Lys Leu Leu Lys Asp Ala
                115                 120                 125

Leu Arg Ile Thr Glu Ser Lys Lys Ala Leu Ala Lys Gln Asn Ser Gly
    130                 135                 140

Gly Ser Thr Ser Gly Glu Ser Pro Asn Gly Pro Thr Gly Gln Glu Asn
145                 150                 155                 160

Gly Arg Asn Ala

<210> SEQ ID NO 5
<211> LENGTH: 456
<212> TYPE: DNA
<213> ORGANISM: Triticum aestivum
<220> FEATURE:
<221> NAME/KEY: CDS
<222> LOCATION: (1)..(456)

<400> SEQUENCE: 5 atg gcg cgg cgc ggg cgt gtg gag ctg cgg cgg atc gag gac cgg acg        48
Met Ala Arg Arg Gly Arg Val Glu Leu Arg Arg Ile Glu Asp Arg Thr
1               5                   10                  15 agc cgg cag gtg cga ttc tcc aag cgc cgc gcg ggg ctc ttc aag aag        96
Ser Arg Gln Val Arg Phe Ser Lys Arg Arg Ala Gly Leu Phe Lys Lys
            20                  25                  30 gcg ttc gag ctc gtg gtc ctc tgc gac gcc gag gtc gcg ctg ctc gtc       144
Ala Phe Glu Leu Val Val Leu Cys Asp Ala Glu Val Ala Leu Leu Val
        35                  40                  45 ttc tcc ccc gcc ggg aag ctc tac gag tac gcc tcc tcc agc atc gaa       192
Phe Ser Pro Ala Gly Lys Leu Tyr Glu Tyr Ala Ser Ser Ser Ile Glu
    50                  55                  60 ggt aca tat gat cgc tat cag aga ttt gca ggg gct gga acg aac gtg       240
Gly Thr Tyr Asp Arg Tyr Gln Arg Phe Ala Gly Ala Gly Thr Asn Val
65                  70                  75                  80 aat gga ggc gat gca agt agc aac aat gat ggt gat cct tca aac ata       288
Asn Gly Gly Asp Ala Ser Ser Asn Asn Asp Gly Asp Pro Ser Asn Ile
                85                  90                  95 cag tca acg ctt aaa gag atc gct tcc tgg tct att caa aac aat gct       336
Gln Ser Thr Leu Lys Glu Ile Ala Ser Trp Ser Ile Gln Asn Asn Ala
            100                 105                 110 gat gtc tca gat gct aat aag cta gag aaa ctg gag aaa ctc ctg aca       384
Asp Val Ser Asp Ala Asn Lys Leu Glu Lys Leu Glu Lys Leu Leu Thr
        115                 120                 125 gat gct ttg agg aat aca aaa tcc aag aag atg ttg gtg caa caa aat       432
Asp Ala Leu Arg Asn Thr Lys Ser Lys Lys Met Leu Val Gln Gln Asn
    130                 135                 140 agc ggc gca agc acg agg ggg tgg                                       456
Ser Gly Ala Ser Thr Arg Gly Trp
145                 150

<210> SEQ ID NO 6
<211> LENGTH: 152
<212> TYPE: PRT
<213> ORGANISM: Triticum aestivum

<400> SEQUENCE: 6

Met Ala Arg Arg Gly Arg Val Glu Leu Arg Arg Ile Glu Asp Arg Thr
```

```
  1               5                   10                  15
Ser Arg Gln Val Arg Phe Ser Lys Arg Arg Ala Gly Leu Phe Lys Lys
            20                  25                  30

Ala Phe Glu Leu Val Val Leu Cys Asp Ala Glu Val Ala Leu Leu Val
            35                  40                  45

Phe Ser Pro Ala Gly Lys Leu Tyr Glu Tyr Ala Ser Ser Ser Ile Glu
        50                  55                  60

Gly Thr Tyr Asp Arg Tyr Gln Arg Phe Ala Gly Ala Gly Thr Asn Val
65                  70                  75                  80

Asn Gly Gly Asp Ala Ser Ser Asn Asn Asp Gly Asp Pro Ser Asn Ile
                    85                  90                  95

Gln Ser Thr Leu Lys Glu Ile Ala Ser Trp Ser Ile Gln Asn Asn Ala
            100                 105                 110

Asp Val Ser Asp Ala Asn Lys Leu Glu Lys Leu Glu Lys Leu Leu Thr
            115                 120                 125

Asp Ala Leu Arg Asn Thr Lys Ser Lys Lys Met Leu Val Gln Gln Asn
            130                 135                 140

Ser Gly Ala Ser Thr Arg Gly Trp
145                 150
```

```
<210> SEQ ID NO 7
<211> LENGTH: 495
<212> TYPE: DNA
<213> ORGANISM: Triticum aestivum
<220> FEATURE:
<221> NAME/KEY: CDS
<222> LOCATION: (1)..(495)

<400> SEQUENCE: 7
```

```
cgg cgc ggg cgt gtg gag ctg cgg cgg atc gag gac cgg acg agc cgg       48
Arg Arg Gly Arg Val Glu Leu Arg Arg Ile Glu Asp Arg Thr Ser Arg
1               5                   10                  15 cag gtg cgc ttc tcc aag cgc gcc tcg ggc ctc ttc aag aag gcc ttc       96
Gln Val Arg Phe Ser Lys Arg Arg Ser Gly Leu Phe Lys Lys Ala Phe
            20                  25                  30 gag ctc gcg gtc ctc tgc gac gcc gag gtc tcg ctg ctc gtc ttc tcc      144
Glu Leu Ala Val Leu Cys Asp Ala Glu Val Ser Leu Leu Val Phe Ser
            35                  40                  45 ccc gcc ggc agg ctc tac gag tac gcc tcc tcc agc ata gaa ggt aca      192
Pro Ala Gly Arg Leu Tyr Glu Tyr Ala Ser Ser Ser Ile Glu Gly Thr
        50                  55                  60 tat gac cgc tat cag gca ttt gca gga gcc gga aag gac gtg aat gaa      240
Tyr Asp Arg Tyr Gln Ala Phe Ala Gly Ala Gly Lys Asp Val Asn Glu
65                  70                  75                  80 ccc ggt gca agt aac aac aat gat gga gat cct tca aat ata cag tca      288
Pro Gly Ala Ser Asn Asn Asn Asp Gly Asp Pro Ser Asn Ile Gln Ser
                    85                  90                  95 agg ctt gaa gag att act acc tgg tct ctt caa aac aat gct gat gac      336
Arg Leu Glu Glu Ile Thr Thr Trp Ser Leu Gln Asn Asn Ala Asp Asp
            100                 105                 110 tca gat gct aat gag cta gag aaa ctg gag aaa cta ctg aca gat gct      384
Ser Asp Ala Asn Glu Leu Glu Lys Leu Glu Lys Leu Leu Thr Asp Ala
            115                 120                 125 ttg aag aat aca aaa tcg aag aag atg ttg gcg caa cga aat agt ggt      432
Leu Lys Asn Thr Lys Ser Lys Lys Met Leu Ala Gln Arg Asn Ser Gly
            130                 135                 140 gca gga acg agt gca agc ggc gag aac tcc agt cgt cct agg gga cag      480
Ala Gly Thr Ser Ala Ser Gly Glu Asn Ser Ser Arg Pro Arg Gly Gln
145                 150                 155                 160
```

```
aag gga agg act                                              495
Lys Gly Gly Arg Thr
            165

<210> SEQ ID NO 8
<211> LENGTH: 165
<212> TYPE: PRT
<213> ORGANISM: Triticum aestivum

<400> SEQUENCE: 8

Arg Arg Gly Arg Val Glu Leu Arg Arg Ile Glu Asp Arg Thr Ser Arg
1               5                   10                  15

Gln Val Arg Phe Ser Lys Arg Ser Gly Leu Phe Lys Lys Ala Phe
            20                  25                  30

Glu Leu Ala Val Leu Cys Asp Ala Glu Val Ser Leu Leu Val Phe Ser
            35                  40                  45

Pro Ala Gly Arg Leu Tyr Glu Tyr Ala Ser Ser Ile Glu Gly Thr
        50                  55                  60

Tyr Asp Arg Tyr Gln Ala Phe Ala Gly Ala Gly Lys Asp Val Asn Glu
65                  70                  75                  80

Pro Gly Ala Ser Asn Asn Asn Asp Gly Asp Pro Ser Asn Ile Gln Ser
                85                  90                  95

Arg Leu Glu Glu Ile Thr Thr Trp Ser Leu Gln Asn Asn Ala Asp Asp
            100                 105                 110

Ser Asp Ala Asn Glu Leu Glu Lys Leu Glu Lys Leu Leu Thr Asp Ala
        115                 120                 125

Leu Lys Asn Thr Lys Ser Lys Lys Met Leu Ala Gln Arg Asn Ser Gly
    130                 135                 140

Ala Gly Thr Ser Ala Ser Gly Glu Asn Ser Ser Arg Pro Arg Gly Gln
145                 150                 155                 160

Lys Gly Gly Arg Thr
            165

<210> SEQ ID NO 9
<211> LENGTH: 528
<212> TYPE: DNA
<213> ORGANISM: Triticum aestivum
<220> FEATURE:
<221> NAME/KEY: CDS
<222> LOCATION: (1)..(528)

<400> SEQUENCE: 9 agg aag agg ggg aag ctg gag ctg cgg cgg ata gag gac cgg acg agc    48
Arg Lys Arg Gly Lys Leu Glu Leu Arg Arg Ile Glu Asp Arg Thr Ser
1               5                   10                  15 cgg cag gtg cga ttc tcg aag cgg cgg agc ggg ctg ttc aag aag gcg    96
Arg Gln Val Arg Phe Ser Lys Arg Arg Ser Gly Leu Phe Lys Lys Ala
            20                  25                  30 tac gag ctg tcc gtg ctc tgc gac gcc cag gtc gcc ctc cta gtc ttc   144
Tyr Glu Leu Ser Val Leu Cys Asp Ala Gln Val Ala Leu Leu Val Phe
            35                  40                  45 tcc ccc gcc ggc cgc ctc tac gag ttc gcc tct tcc acc tcc agc att   192
Ser Pro Ala Gly Arg Leu Tyr Glu Phe Ala Ser Ser Thr Ser Ser Ile
        50                  55                  60 gat aca att ttt ggt cgg tat tgg gac ctt ctg gac aca aca att gat   240
Asp Thr Ile Phe Gly Arg Tyr Trp Asp Leu Leu Asp Thr Thr Ile Asp
65                  70                  75                  80 ctc aat att gaa gca agg gaa tct cgg gtt gat tgc aat ata cag ctt   288
Leu Asn Ile Glu Ala Arg Glu Ser Arg Val Asp Cys Asn Ile Gln Leu
```

```
cgt cag aaa gag cgt tca gat gac ccg gtg cct aag ata aac cac att      336
Arg Gln Lys Glu Arg Ser Asp Asp Pro Val Pro Lys Ile Asn His Ile
            100                 105                 110 act caa tgt gtg ttg gaa tca aat gtc aac gag ctg aac atc gct gag      384
Thr Gln Cys Val Leu Glu Ser Asn Val Asn Glu Leu Asn Ile Ala Glu
        115                 120                 125 cta aga ggt ttg gag gaa gcg atg act aat gct ttg aca gtt gtt aag      432
Leu Arg Gly Leu Glu Glu Ala Met Thr Asn Ala Leu Thr Val Val Lys
    130                 135                 140 aac aaa ctg atg atg aag gtg gct agt gtg ctc ccc caa agc gag aag      480
Asn Lys Leu Met Met Lys Val Ala Ser Val Leu Pro Gln Ser Glu Lys
145                 150                 155                 160 aag agg aag agt tgc tcg att tca gag cca aga tca gga gtg agc tct      528
Lys Arg Lys Ser Cys Ser Ile Ser Glu Pro Arg Ser Gly Val Ser Ser
                165                 170                 175
```

<210> SEQ ID NO 10
<211> LENGTH: 176
<212> TYPE: PRT
<213> ORGANISM: Triticum aestivum

<400> SEQUENCE: 10

```
Arg Lys Arg Gly Lys Leu Glu Leu Arg Arg Ile Glu Asp Arg Thr Ser
1               5                   10                  15

Arg Gln Val Arg Phe Ser Lys Arg Ser Gly Leu Phe Lys Lys Ala
            20                  25                  30

Tyr Glu Leu Ser Val Leu Cys Asp Ala Gln Val Ala Leu Leu Val Phe
        35                  40                  45

Ser Pro Ala Gly Arg Leu Tyr Glu Phe Ala Ser Ser Thr Ser Ser Ile
    50                  55                  60

Asp Thr Ile Phe Gly Arg Tyr Trp Asp Leu Leu Asp Thr Thr Ile Asp
65              70                  75                  80

Leu Asn Ile Glu Ala Arg Glu Ser Arg Val Asp Cys Asn Ile Gln Leu
                85                  90                  95

Arg Gln Lys Glu Arg Ser Asp Asp Pro Val Pro Lys Ile Asn His Ile
            100                 105                 110

Thr Gln Cys Val Leu Glu Ser Asn Val Asn Glu Leu Asn Ile Ala Glu
        115                 120                 125

Leu Arg Gly Leu Glu Glu Ala Met Thr Asn Ala Leu Thr Val Val Lys
    130                 135                 140

Asn Lys Leu Met Met Lys Val Ala Ser Val Leu Pro Gln Ser Glu Lys
145                 150                 155                 160

Lys Arg Lys Ser Cys Ser Ile Ser Glu Pro Arg Ser Gly Val Ser Ser
                165                 170                 175
```

<210> SEQ ID NO 11
<211> LENGTH: 312
<212> TYPE: DNA
<213> ORGANISM: Triticum aestivum
<220> FEATURE:
<221> NAME/KEY: CDS
<222> LOCATION: (1)..(312)

<400> SEQUENCE: 11

```
atg gcg cgg cgc ggg cgt gtg gag ctg cgg cgg atc gag gac cgg acg       48
Met Ala Arg Arg Gly Arg Val Glu Leu Arg Arg Ile Glu Asp Arg Thr
1               5                   10                  15 agc cgg cag gtg cgc ttc tcc aag cgc cgc gcg ggg ctc ttc aag aag       96
```

```
                                                                       -continued Ser Arg Gln Val Arg Phe Ser Lys Arg Arg Ala Gly Leu Phe Lys Lys
            20                  25                  30 gcc ttc gag ctc gcg gtc ctc tgc gac gcc gag gtc tcg ctg ctc gtc      144
Ala Phe Glu Leu Ala Val Leu Cys Asp Ala Glu Val Ser Leu Leu Val
        35                  40                  45 ttc tcc ccc gcc ggc agg ctc tac gag tac gcc tcc tcc aga att cca      192
Phe Ser Pro Ala Gly Arg Leu Tyr Glu Tyr Ala Ser Ser Arg Ile Pro
50                  55                  60 cta ttc gct ggt gct tct aca tgc ttt cat tgg ata ttc cag acc acc      240
Leu Phe Ala Gly Ala Ser Thr Cys Phe His Trp Ile Phe Gln Thr Thr
65                  70                  75                  80 tta gtc gga gtt caa caa gct tct ctt caa tca acg cca ccc cta cct      288
Leu Val Gly Val Gln Gln Ala Ser Leu Gln Ser Thr Pro Pro Leu Pro
                85                  90                  95 cat cat gta ttc act ctt cat aat                                      312
His His Val Phe Thr Leu His Asn
            100

<210> SEQ ID NO 12
<211> LENGTH: 104
<212> TYPE: PRT
<213> ORGANISM: Triticum aestivum

<400> SEQUENCE: 12

Met Ala Arg Arg Gly Arg Val Glu Leu Arg Arg Ile Glu Asp Arg Thr
1               5                   10                  15

Ser Arg Gln Val Arg Phe Ser Lys Arg Arg Ala Gly Leu Phe Lys Lys
            20                  25                  30

Ala Phe Glu Leu Ala Val Leu Cys Asp Ala Glu Val Ser Leu Leu Val
        35                  40                  45

Phe Ser Pro Ala Gly Arg Leu Tyr Glu Tyr Ala Ser Ser Arg Ile Pro
50                  55                  60

Leu Phe Ala Gly Ala Ser Thr Cys Phe His Trp Ile Phe Gln Thr Thr
65                  70                  75                  80

Leu Val Gly Val Gln Gln Ala Ser Leu Gln Ser Thr Pro Pro Leu Pro
                85                  90                  95

His His Val Phe Thr Leu His Asn
            100

<210> SEQ ID NO 13
<211> LENGTH: 609
<212> TYPE: DNA
<213> ORGANISM: Brachypodium distachyon
<220> FEATURE:
<221> NAME/KEY: CDS
<222> LOCATION: (1)..(609)

<400> SEQUENCE: 13 atg gag gag agg agg atg ttg cag gag cag cag cag gag gag gct cat       48
Met Glu Glu Arg Arg Met Leu Gln Glu Gln Gln Gln Glu Glu Ala His
1               5                   10                  15 ggc cat ggg gga aag gag gag gag ggg aag agg agg aag aag cgt ggg       96
Gly His Gly Gly Lys Glu Glu Glu Gly Lys Arg Arg Lys Lys Arg Gly
            20                  25                  30 aag gtg gag ctg agg agg ata gag gac cgg acg agc cgg cag gtg cgc      144
Lys Val Glu Leu Arg Arg Ile Glu Asp Arg Thr Ser Arg Gln Val Arg
        35                  40                  45 ttc tcg aag cgg cgg agc ggg ctg ttc aag aag gcg ttc gag ctg tcc      192
Phe Ser Lys Arg Arg Ser Gly Leu Phe Lys Lys Ala Phe Glu Leu Ser
50                  55                  60
```

```
gtg ctg tgc gac gtc gag gtc gcg ctc atc gtc ttc tcc ccc gcc gga    240
Val Leu Cys Asp Val Glu Val Ala Leu Ile Val Phe Ser Pro Ala Gly
65                  70                  75                  80 cga ctc tac ccg ttc gtc tcc tcc gaa agc agc gtt gag gag att ttt    288
Arg Leu Tyr Pro Phe Val Ser Ser Glu Ser Ser Val Glu Glu Ile Phe
                85                  90                  95 ggt cga tgc cgg cat ctt ccc aac aca ata gat ctc aat att gag gta    336
Gly Arg Cys Arg His Leu Pro Asn Thr Ile Asp Leu Asn Ile Glu Val
            100                 105                 110 cga gat cct cga gtt gat cac gat ata cag att gat ctg aat gag cag    384
Arg Asp Pro Arg Val Asp His Asp Ile Gln Ile Asp Leu Asn Glu Gln
        115                 120                 125 gca gca cca gac cca cta tct gat tta aac cac ttt gct gac tgg atc    432
Ala Ala Pro Asp Pro Leu Ser Asp Leu Asn His Phe Ala Asp Trp Ile
    130                 135                 140 ctg gaa att gat gtt aac tcg atg ggc atg gct gag cta aga cgt ttt    480
Leu Glu Ile Asp Val Asn Ser Met Gly Met Ala Glu Leu Arg Arg Phe
145                 150                 155                 160 gag gaa att gtt tct gac gct ctg aca gtt atc aag aac aat ctg agg    528
Glu Glu Ile Val Ser Asp Ala Leu Thr Val Ile Lys Asn Asn Leu Arg
                165                 170                 175 atg aag gtg tca cag ctc acc cag acc gag aga aac cca cag gag aaa    576
Met Lys Val Ser Gln Leu Thr Gln Thr Glu Arg Asn Pro Gln Glu Lys
            180                 185                 190 gcg aac aac ttg tca agc caa gaa tcg gag gag                        609
Ala Asn Asn Leu Ser Ser Gln Glu Ser Glu Glu
        195                 200
```

<210> SEQ ID NO 14
<211> LENGTH: 203
<212> TYPE: PRT
<213> ORGANISM: Brachypodium distachyon

<400> SEQUENCE: 14

```
Met Glu Glu Arg Arg Met Leu Gln Glu Gln Gln Glu Glu Ala His
1               5                   10                  15

Gly His Gly Gly Lys Glu Glu Glu Gly Lys Arg Arg Lys Lys Arg Gly
                20                  25                  30

Lys Val Glu Leu Arg Arg Ile Glu Asp Arg Thr Ser Arg Gln Val Arg
            35                  40                  45

Phe Ser Lys Arg Arg Ser Gly Leu Phe Lys Lys Ala Phe Glu Leu Ser
        50                  55                  60

Val Leu Cys Asp Val Glu Val Ala Leu Ile Val Phe Ser Pro Ala Gly
65                  70                  75                  80

Arg Leu Tyr Pro Phe Val Ser Ser Glu Ser Ser Val Glu Glu Ile Phe
                85                  90                  95

Gly Arg Cys Arg His Leu Pro Asn Thr Ile Asp Leu Asn Ile Glu Val
            100                 105                 110

Arg Asp Pro Arg Val Asp His Asp Ile Gln Ile Asp Leu Asn Glu Gln
        115                 120                 125

Ala Ala Pro Asp Pro Leu Ser Asp Leu Asn His Phe Ala Asp Trp Ile
    130                 135                 140

Leu Glu Ile Asp Val Asn Ser Met Gly Met Ala Glu Leu Arg Arg Phe
145                 150                 155                 160

Glu Glu Ile Val Ser Asp Ala Leu Thr Val Ile Lys Asn Asn Leu Arg
                165                 170                 175

Met Lys Val Ser Gln Leu Thr Gln Thr Glu Arg Asn Pro Gln Glu Lys
            180                 185                 190
```

```
Ala Asn Asn Leu Ser Ser Gln Glu Ser Glu Glu
        195                 200
```

<210> SEQ ID NO 15
<211> LENGTH: 477
<212> TYPE: DNA
<213> ORGANISM: Brachypodium distachyon
<220> FEATURE:
<221> NAME/KEY: CDS
<222> LOCATION: (1)..(477)

<400> SEQUENCE: 15

```
atg gtg cgg cgc ggg cgg gtg gag ctg cgg cgg atc gag gac cgg acg      48
Met Val Arg Arg Gly Arg Val Glu Leu Arg Arg Ile Glu Asp Arg Thr
1               5                   10                  15 agc cgg cag gtg cgc ttc tcc aag cgc cgg tcg ggc ctc ttc aag aag      96
Ser Arg Gln Val Arg Phe Ser Lys Arg Arg Ser Gly Leu Phe Lys Lys
                20                  25                  30 gcc ttc gag ctc gcg ctc ctc tgc gac gcc gag gtc gcg ctc ctc gtc     144
Ala Phe Glu Leu Ala Leu Leu Cys Asp Ala Glu Val Ala Leu Leu Val
            35                  40                  45 ttc tcc ccc gcc ggc aag ctc tac gag tac tcc tcc tcc tta agc att     192
Phe Ser Pro Ala Gly Lys Leu Tyr Glu Tyr Ser Ser Ser Leu Ser Ile
        50                  55                  60 gaa ggc aca tat gac cgc tat cag caa ttt gcg gga gcc gta agg aac     240
Glu Gly Thr Tyr Asp Arg Tyr Gln Gln Phe Ala Gly Ala Val Arg Asn
65                  70                  75                  80 aca tat caa gga ggc gca agt acc agc aat gat gaa gat cct tca aat     288
Thr Tyr Gln Gly Gly Ala Ser Thr Ser Asn Asp Glu Asp Pro Ser Asn
                85                  90                  95 cta cag tca agg ctt agg gag att act gcc tgg tct gtt cac aat aat     336
Leu Gln Ser Arg Leu Arg Glu Ile Thr Ala Trp Ser Val His Asn Asn
            100                 105                 110 gct gat aat gca gat gcc agt aat cta gag aaa ctg gag aaa cta ctg     384
Ala Asp Asn Ala Asp Ala Ser Asn Leu Glu Lys Leu Glu Lys Leu Leu
        115                 120                 125 aca gat gct aag agg gct ttg gcg aaa caa aat agc aac agg agt gca     432
Thr Asp Ala Lys Arg Ala Leu Ala Lys Gln Asn Ser Asn Arg Ser Ala
    130                 135                 140 acc ggt gag aac tcc aat gga cct act gga gag gga gga aac gct         477
Thr Gly Glu Asn Ser Asn Gly Pro Thr Gly Glu Gly Gly Asn Ala
145                 150                 155
```

<210> SEQ ID NO 16
<211> LENGTH: 159
<212> TYPE: PRT
<213> ORGANISM: Brachypodium distachyon

<400> SEQUENCE: 16

```
Met Val Arg Arg Gly Arg Val Glu Leu Arg Arg Ile Glu Asp Arg Thr
1               5                   10                  15

Ser Arg Gln Val Arg Phe Ser Lys Arg Arg Ser Gly Leu Phe Lys Lys
                20                  25                  30

Ala Phe Glu Leu Ala Leu Leu Cys Asp Ala Glu Val Ala Leu Leu Val
            35                  40                  45

Phe Ser Pro Ala Gly Lys Leu Tyr Glu Tyr Ser Ser Ser Leu Ser Ile
        50                  55                  60

Glu Gly Thr Tyr Asp Arg Tyr Gln Gln Phe Ala Gly Ala Val Arg Asn
65                  70                  75                  80

Thr Tyr Gln Gly Gly Ala Ser Thr Ser Asn Asp Glu Asp Pro Ser Asn
```

```
                         85                  90                  95

Leu Gln Ser Arg Leu Arg Glu Ile Thr Ala Trp Ser Val His Asn Asn
            100                 105                 110

Ala Asp Asn Ala Asp Ala Ser Asn Leu Glu Lys Leu Glu Lys Leu Leu
        115                 120                 125

Thr Asp Ala Lys Arg Ala Leu Ala Lys Gln Asn Ser Asn Arg Ser Ala
130                 135                 140

Thr Gly Glu Asn Ser Asn Gly Pro Thr Gly Glu Gly Gly Asn Ala
145                 150                 155

<210> SEQ ID NO 17
<211> LENGTH: 321
<212> TYPE: DNA
<213> ORGANISM: Brachypodium distachyon
<220> FEATURE:
<221> NAME/KEY: CDS
<222> LOCATION: (1)..(321)

<400> SEQUENCE: 17 atg gcg cgg cgc ggg cgg gtg gag ctg cgg cgg atc gag gac cgg acg      48
Met Ala Arg Arg Gly Arg Val Glu Leu Arg Arg Ile Glu Asp Arg Thr
1               5                   10                  15 agc cgg cag gtg cgc ttc tcc aag cgc cgg gcg ggg ctc ttc aag aag      96
Ser Arg Gln Val Arg Phe Ser Lys Arg Arg Ala Gly Leu Phe Lys Lys
            20                  25                  30 gcc ttc gag ctc gcc gtc ctc tgc gac gcc gag gtc gcg ctg ctc gtc     144
Ala Phe Glu Leu Ala Val Leu Cys Asp Ala Glu Val Ala Leu Leu Val
        35                  40                  45 ttc tcc ccc gcc ggc agg ctc tac gag tac gcc tcc tcc ata agc ata     192
Phe Ser Pro Ala Gly Arg Leu Tyr Glu Tyr Ala Ser Ser Ile Ser Ile
    50                  55                  60 gaa ggt aca tat gac cgc tat cag aga ttt gcg gga ggc aga tgg aat     240
Glu Gly Thr Tyr Asp Arg Tyr Gln Arg Phe Ala Gly Gly Arg Trp Asn
65                  70                  75                  80 ctg aat gat gga gat tca agt agc aac aat gat gaa gat cct tca aac     288
Leu Asn Asp Gly Asp Ser Ser Ser Asn Asn Asp Glu Asp Pro Ser Asn
                85                  90                  95 ata caa tca aga ctt gga gag att gcc tcc tgg                         321
Ile Gln Ser Arg Leu Gly Glu Ile Ala Ser Trp
            100                 105

<210> SEQ ID NO 18
<211> LENGTH: 107
<212> TYPE: PRT
<213> ORGANISM: Brachypodium distachyon

<400> SEQUENCE: 18

Met Ala Arg Arg Gly Arg Val Glu Leu Arg Arg Ile Glu Asp Arg Thr
1               5                   10                  15

Ser Arg Gln Val Arg Phe Ser Lys Arg Arg Ala Gly Leu Phe Lys Lys
            20                  25                  30

Ala Phe Glu Leu Ala Val Leu Cys Asp Ala Glu Val Ala Leu Leu Val
        35                  40                  45

Phe Ser Pro Ala Gly Arg Leu Tyr Glu Tyr Ala Ser Ser Ile Ser Ile
    50                  55                  60

Glu Gly Thr Tyr Asp Arg Tyr Gln Arg Phe Ala Gly Arg Trp Asn
65                  70                  75                  80

Leu Asn Asp Gly Asp Ser Ser Asn Asn Asp Glu Asp Pro Ser Asn
                85                  90                  95
```

Ile Gln Ser Arg Leu Gly Glu Ile Ala Ser Trp
        100                 105

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
aaatccaaga tattggcaaa acg                                           23

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
ccttaggctc actggagttc tca                                           23

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
ccggcaagct ctacgagtac tc                                            22

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
gctcccgcaa attgctgat                                                19

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
aatctgagga tgaaggtgtc aca                                           23

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
gcttgacaag ttgttcgctt tct                                           23

<210> SEQ ID NO 25
<211> LENGTH: 20
<212> TYPE: DNA

<213> ORGANISM: Artificial Sequence
<220> FEATURE:
<223> OTHER INFORMATION: primer

<400> SEQUENCE: 25
gtcgacttcc ccgagcatta         20

<210> SEQ ID NO 26
<211> LENGTH: 17
<212> TYPE: DNA
<213> ORGANISM: Artificial Sequence
<220> FEATURE:
<223> OTHER INFORMATION: primer

<400> SEQUENCE: 26
ataggcgccg ggttgag         17

<210> SEQ ID NO 27
<211> LENGTH: 12952
<212> TYPE: DNA
<213> ORGANISM: Artificial Sequence
<220> FEATURE:
<223> OTHER INFORMATION: vector

<400> SEQUENCE: 27
gccgatcgtg aagtttctca tctaagcccc catttggacg tgaatgtaga cacgtcgaaa      60
taaagatttc cgaattagaa taatttgttt attgctttcg cctataaata cgacggatcg     120
taatttgtcg ttttatcaaa atgtactttc attttataat aacgctgcgg acatctacat     180
ttttgaattg aaaaaaaatt ggtaattact ctttcttttt ctccatattg accatcatac     240
tcattgctga tccatgtaga tttcccggac atgaagccat ttacaattga atatatcctg     300
ccgccgctgc cgctttgcac ccggtggagc ttgcatgttg gtttctacgc agaactgagc     360
cggttaggca gataatttcc attgagaact gagccatgtg caccttcccc ccaacacggt     420
gagcgacggg gcaacggagt gatccacatg ggacttttaa acatcatccg tcggatggcg     480
ttgcgagaga agcagtcgat ccgtgagatc agccgacgca ccgggcaggc gcgcaacacg     540
atcgcaaagt atttgaacgc aggtacaatc gagccgacgt tcacgcggaa cgaccaagca     600
agctatgttg cgattacttc gccaactatt gcgataacaa gaaaaagcca gcctttcatg     660
atatatctcc caatttgtgt agggcttatt atgcacgctt aaaaataata aaagcagact     720
tgacctgata gtttggctgt gagcaattat gtgcttagtg catctaacgc ttgagttaag     780
ccgcgccgcg aagcggcgtc ggcttgaacg aattgttaga cattatttgc cgactacctt     840
ggtgatctcg cctttcacgt agtggacaaa ttcttccaac tgatctgcgc gcgaggccaa     900
gcgatcttct tcttgtccaa gataagcctg tctagcttca agtatgacgg gctgatactg     960
ggccggcagg cgctccattg cccagtcggc agcgacatcc ttcggcgcga ttttgccggt    1020
tactgcgctg taccaaatgc gggacaacgt aagcactaca tttcgctcat cgccagccca    1080
gtcgggcggc gagttccata gcgttaaggt ttcatttagc gcctcaaata gatcctgttc    1140
aggaaccgga tcaaagagtt cctccgccgc tggacctacc aaggcaacgc tatgttctct    1200
tgcttttgtc agcaagatag ccagatcaat gtcgatcgtg gctggctcga agatacctgc    1260
aagaatgtca ttgcgctgcc attctccaaa ttgcagttcg cgcttagctg gataacgcca    1320
cggaatgatg tcgtcgtgca caacaatggt gacttctaca gcgcggagaa tctcgctctc    1380
tccaggggaa gccgaagttt ccaaaaggtc gttgatcaaa gctcgccgcg ttgtttcatc    1440
aagccttacg gtcaccgtaa ccagcaaatc aatatcactg tgtggcttca ggccgccatc    1500

```
cactgcggag ccgtacaaat gtacggccag caacgtcggt tcgagatggc gctcgatgac    1560
gccaactacc tctgatagtt gagtcgatac ttcggcgatc accgcttccc tcatgatgtt    1620
taactttgtt ttagggcgac tgccctgctg cgtaacatcg ttgctgctcc ataacatcaa    1680
acatcgaccc acggcgtaac gcgcttgctg cttggatgcc cgaggcatag actgtaccc c   1740 aaaaaaacag tcataacaag ccatgaaaac cgccactgcg ccgttaccac cgctgcgttc    1800
ggtcaaggtt ctggaccagt tgcgtgagcg catacgctac ttgcattaca gcttacgaac    1860
cgaacaggct tatgtccact gggttcgtgc cttcatccgt ttccacggtg tgcgtcaccc    1920
ggcaaccttg ggcagcagcg aagtcgaggc atttctgtcc tggctggcga acgagcgcaa    1980
ggtttcggtc tccacgcatc gtcaggcata cccaccggtg ccttgatgtg ggcgccggcg    2040
gtcgagtggc gacggcgcgg cttgtccgcg ccctggtaga ttgcctggcc gtaggccagc    2100 cattttttgag cggccagcgg ccgcgatagg ccgacgcgaa gcggcggggc gtaggagcg    2160 cagcgaccga agggtaggcg cttttttgcag ctcttcggct gtgcgctggc cagacagtta    2220
tgcacaggcc aggcgggttt taagagtttt aataagtttt aaagagtttt aggcggaaaa    2280
atcgcctttt ttctctttta tatcagtcac ttacatgtgt gaccggttcc caatgtacgg    2340
ctttgggttc ccaatgtacg ggttccggtt cccaatgtac ggctttgggt tcccaatgta    2400
cgtgctatcc acaggaaaga gacccttttcg accttttttcc cctgctaggg caatttgccc    2460
tagcatctgc tccgtacatt aggaaccggc ggatgcttcg ccctcgatca ggttgcggta    2520
gcgcatgact aggatcgggc cagcctgccc cgcctcctcc ttcaaatcgt actccggcag    2580
gtcatttgac ccgatcagct tgcgcacggt gaaacagaac ttcttgaact ctccggcgct    2640
gccactgcgt tcgtagatcg tcttgaacaa ccatctggct tctgccttgc ctgcggcgcg    2700
gcgtgccagg cggtagagaa aacggccgat gccgggatcg atcaaaaagt aatcggggtg    2760
aaccgtcagc acgtccgggt tcttgccttc tgtgatctcg cggtacatcc aatcagctag    2820
ctcgatctcg atgtactccg gccgcccggt ttcgctcttt acgatcttgt agcggctaat    2880
caaggcttca ccctcggata ccgtcaccag gcggccgttc ttggccttct tcgtacgctg    2940
catggcaacg tgcgtggtgt ttaaccgaat gcaggtttct accaggtcgt cttttctgctt    3000 tccgccatcg gctcgccggc agaacttgag tacgtccgca acgtgtggac ggaacacgcg    3060
gccgggcttg tctcccttcc cttcccggta tcggttcatg gattcggtta gatgggaaac    3120
cgccatcagt accaggtcgt aatcccacac actcgccatg ccggccggcc ctgcggaaac    3180
ctctacgtgc ccgtctggaa gctcgtagcg gatcacctcg ccagtcgtc ggtcacgctt    3240 cgacagacgg aaaacggcca cgtccatgat gctgcgacta tcgcgggtgc ccacgtcata    3300
gagcatcgga acgaaaaaat ctggttgctc gtcgcccttg ggcggcttcc taatcgacgg    3360
cgcaccggct gccggcggtt gccgggattc tttgcggatt cgatcagcgg ccgcttgcca    3420
cgattcaccg gggcgtgctt ctgcctcgat gcgttgccgc tgggcggcct gcgccgcctt    3480
caacttctcc accaggtcat cacccagcgc cgcgccgatt tgtaccgggc cggatggttt    3540
gcgaccgctc acgccgattc ctcgggcttg ggggttccag tgccattgca gggcggcag    3600 acaacccagc cgcttacgcc tggccaaccg cccgttcctc cacacatggg gcattccacg    3660
gcgtcggtgc ctggttgttc ttgattttcc atgccgcctc ctttagccgc taaaattcat    3720
ctactcattt attcatttgc tcatttactc tggtagctgc gcgatgtatt cagatagcag    3780
ctcggtaatg gtcttgcctt ggcgtaccgc gtacatcttc agcttggtgt gatcctccgc    3840
```

-continued

```
cggcaactga aagttgaccc gcttcatggc tggcgtgtct gccaggctgg ccaacgttgc   3900
agccttgctg ctgcgtgcgc tcggacggcc ggcacttagc gtgtttgtgc ttttgctcat   3960
ttctctttta cctcattaac tcaaatgagt tttgatttaa tttcagcggc cagcgcctgg   4020
acctcgcggg cagcgtcgcc ctcgggttct gattcaagaa cggttgtgcc ggcggcggca   4080
gtgcctgggt agctcacgcg ctgcgtgata cgggactcaa gaatgggcag ctcgtacccg   4140
gccagcgcct cggcaacctc accgccgatg cgcgtgcctt tgatcgcccg cgacacgaca   4200
aaggccgctt gtagccttcc atccgtgacc tcaatgcgct gcttaaccag ctccaccagg   4260
tcggcggtgg cccatatgtc gtaagggctt ggctgcaccg aatcagcac gaagtcggct   4320
gccttgatcg cggacacagc caagtccgcc gcctggggcg ctccgtcgat cactacgaag   4380
tcgcgccggc cgatggcctt cacgtcgcgg tcaatcgtcg gcggtcgat gccgacaacg   4440
gttagcggtt gatcttcccg cacggccgcc caatcgcggg cactgccctg gggatcggaa   4500
tcgactaaca gaacatcggc cccggcgagt gcaggggcgc gggctagatg ggttgcgatg   4560
gtcgtcttgc ctgacccgcc tttctggtta agtacagcga taaccttcat gcgttcccct   4620
tgcgtatttg tttatttact catcgcatca tatacgcagc gaccgcatga cgcaagctgt   4680
tttactcaaa tacacatcac cttttagac ggcggcgctc ggtttcttca gcggccaagc   4740
tcgccggcca ggccgcgagc ttggcatcag acaaaccggc caggatttca tgcagccgca   4800
cggttgagac gtgcgcgggc ggctcgaaca cgtacccggc cgcgatcatc tccgcctcga   4860
tctcttcggt aatgaaaaac ggttcgtcct ggccgtcctg gtgcggtttc atgcttgttc   4920
ctcttggcgt tcattctcgg cggccgccag ggcgtcggcc tcggtcaatg cgtcctcacg   4980
gaaggcaccg cgccgcctgg cctcggtggg cgtcacttcc tcgctgcgct caagtgcgcg   5040
gtacagggtc gagcgatgca cgccaagcag tgcagccgcc tctttcacgg tgcggccttc   5100
ctggtcgatc agctcgcggg cgtgcgcgat ctgtgccggg gtgagggtag ggcgggggcc   5160
aaacttcacg cctcgcgcct tggcggcctc gcgcccgctc cgggtgcggt cgatgattag   5220
ggaacgctcg aactcggcaa tgccggcgaa cacggtcaac accatgcggc cggccggcgt   5280
ggtggtgtcg gccacggct ctgccaggct acgcaggccc cgccggcct cctggatgcg   5340
ctcggcaatg tccagtaggt cgcgggtgct gcgggccagg cggtctagcc tggtcactgt   5400
cacaacgtcg ccagggcgta ggtggtcaag catcctggcc agctccgggc ggtcgcgcct   5460
ggtgccggtg atcttctcgg aaaacagctt ggtgcagccg gccgcgtgca gttcggcccg   5520
ttggttggtc aagtcctggt cgtcggtgct gacgcgggca tagcccagca ggccagcggc   5580
ggcgctcttg ttcatggcgt aatgtctccg gttctagtcg caagtattct actttatgcg   5640
actaaaacac gcgacaagaa aacgccagga aaagggcagg gcggcagcct gtcgcgtaac   5700
ttaggacttg tgcgacatgt cgtttttcaga agacggctgc actgaacgtc agaagccgac   5760
tgcactatag cagcggaggg gttggatcga cctcgacgta ccctgcctc gcgcgttttcg   5820
gtgatgacgg tgaaaacctc tgacacatgc agctcccgga gacggtcaca gcttgtctgt   5880
aagcggatgc cgggagcaga caagcccgtc agggcgcgtc agcgggtgtt ggcgggtgtc   5940
ggggcgcagc catgacccag tcacgtagcg atagcggagt gtatactggc ttaactatgc   6000
ggcatcagag cagattgtac tgagagtgca ccatatgcgg tgtgaaatac cgcacagatg   6060
cgtaaggaga aaataccgca tcaggcgctc ttccgcttcc tcgctcactg actcgctgcg   6120
ctcggtcgtt cggctgcggc gagcggtatc agctcactca aaggcggtaa tcggttatcc   6180
acagaatcag gggataacgc aggaaagaac atgtgagcaa aaggccagca aaaggccagg   6240
```

```
aaccgtaaaa aggccgcgtt gctggcgttt tccataggc tccgcccccc tgacgagcat   6300
cacaaaaatc gacgctcaag tcagaggtgg cgaaacccga caggactata agataccag   6360 gcgtttcccc ctggaagctc cctcgtgcgc tctcctgttc cgaccctgcc gcttaccgga   6420
tacctgtccg cctttctccc ttcgggaagc gtggcgcttt ctcatagctc acgctgtagg   6480
tatctcagtt cggtgtaggt cgttcgctcc aagctgggct gtgtgcacga accccccgtt   6540
cagcccgacc gctgcgcctt atccggtaac tatcgtcttg agtccaaccc ggtaagacac   6600
gacttatcgc cactggcagc agccactggt aacaggatta gcagagcgag gtatgtaggc   6660
ggtgctacag agttcttgaa gtggtggcct aactacggct acactagaag aacagtattt   6720
ggtatctgcg ctctgctgaa gccagttacc ttcggaaaaa gagttggtag ctcttgatcc   6780
ggcaaacaaa ccaccgctgg tagcggtggt ttttttgttt gcaagcagca gattacgcgc   6840
agaaaaaaag gatctcaaga agatcctttg atcttttcta cggggtctga cgctcagtgg   6900
aacgaaaact cacgttaagg gattttggtc atgagattat caaaaaggat cttcacctag   6960
atccttttcg gcgtccacat caacggcgtc ggcggcgact gcccaggcaa gaccgagatg   7020
caccgcgata tcttgctgcg ttcggatatt tcgtggagt tccgccaca gacccggatt   7080 gaaggcgaga tccagcaact cgcgccagat catcctgtga cggaactttg gcgcgtgatg   7140
actggccagg acgtcggccg aaagagcgac aagcagatca cgcttttcga cagcgtcgga   7200
tttgcgatcg aggatttttc ggcgctgcgc tacgtccgcg accgcgttga gggatcaagc   7260
cacagcagcc cactcgacct tctagccgac ccagacgagc caagggatct ttttggaatg   7320
ctgctccgtc gtcaggcttt ccgacgtttg ggtggttgaa cagaagtcat tatcgcacgg   7380
aatgccaagc actcccgagg ggaaccctgt ggttggcatg cacatacaaa tggacgaacg   7440
gataaacctt ttcacgccct tttaaatatc cgattattct aataaacgct cttttctctt   7500
aggtttaccc gccaatatat cctgtcaaac actgatagtt taaaccgaag gcgggaaacg   7560
acaatctgat cgggtaccgg gcccaagatc tggcccttaa ggccttacta ggctgcagtg   7620
cagcgtgacc cggtcgtgcc cctctctaga gataatgagc attgcatgtc taagttataa   7680
aaaattacca catattttt ttgtcacact tgtttgaagt gcagtttatc tatctttata   7740
catatattta aacttactc tacgaataat ataatctata gtactacaat aatatcagtg   7800
ttttagagaa tcatataaat gaacagttag acatggtcta aaggcaatt gagtattttg   7860 acaacaggac tctacagttt tatcttttta gtgtgcatgt gttctccttt ttttttgcaa   7920
atagcttcac ctatataata cttcatccat tttattagta catccattta gggtttaggg   7980
ttaatggttt ttatagacta attttttag tacatctatt ttattctatt ttagcctcta   8040
aattaagaaa actaaaactc tatttagtt tttttattta ataatttaga tataaaatag   8100
aataaaataa agtgactaaa aattaaacaa ataccctta agaaattaaa aaaactaagg   8160
aaacattttt cttgtttcga gtagataatg ccagcctgtt aaacgccgtc gatcgacgag   8220
tctaacggac accaaccagc gaaccagcag cgtcgcgtcg gccaagcga agcagacggc   8280 acggcatctc tgtcgctgcc tctgaccccc tctcgagagt tccgctccac cgttggactt   8340
gctccgctgt cggcatccag aaattgcgtg gcggagcggc agacgtgagc cggcacggca   8400
ggcggcctcc tcctcctctc acggcaccgg cagctacggg ggattccttt cccaccgctc   8460
cttcgctttc ccttcctcgc ccgccgtaat aaatagacac cccctccaca ccctcttttcc   8520 ccaacctcgt gttgttcgga gcgcacacac acacaaccag atctccccca aatccacccg   8580
```

-continued

```
tcggcacctc cgcttcaagg tacgccgctc gtcctccccc cccccccctc tctaccttct   8640
ctagatcggc gttccggtcc atggttaggg cccggtagtt ctacttctgt tcatgtttgt   8700
gttagatccg tgtttgtgtt agatccgtgc tgctagcgtt cgtacacgga tgcgacctgt   8760
acgtcagaca cgttctgatt gctaacttgc cagtgtttct ctttgggaa tcctgggatg    8820
gctctagccg ttccgcagac gggatcgatc taggataggt atacatgttg atgtgggttt   8880
tactgatgca tatacatgat ggcatatgca gcatctattc atatgctcta accttgagta   8940
cctatctatt ataataaaca agtatgtttt ataattattt tgatcttgat atacttggat   9000
gatggcatat gcagcagcta tatgtggatt tttttagccc tgccttcata cgctatttat   9060
ttgcttggta ctgtttcttt tgtcgatgct caccctgttg tttggtgtta cttctgcagg   9120
tactagtgga tcccccgggc tgcaggaatt caagcttacg cgtgtcatca aagtttgta    9180
caaaaagca ggcttaatgg aggagaggag gatgttgcag gagcagcagc aggaggaggc    9240
tcatggccat gggggaaagg aggaggaggg gaagaggagg aagaagcgtg ggaaggtgga   9300
gctgaggagg atagaggacc ggacgagccg gcaggtgcgc ttctcgaagc ggcggagcgg   9360
gctgttcaag aaggcgttcg agctgtccgt gctgtgcgac gtcgaggtcg cgctcatcgt   9420
cttctccccc gccggacgac tctacccgtt cgtctcctcc gaaagcagcg ttgaggagat   9480
ttttggtcga tgccggcatc ttcccaacac aatagatctc aatattgagg tacgagatcc   9540
tcgagttgat cacgatatac agattgatct gaatgagcag gcagcaccag cccactatc    9600
tgatttaaac cactttgctg actggatcct ggaaattgat gttaactcga tgggcatggc   9660
tgagctaaga cgttttgagg aaattgtttc tgacgctctg acagttatca agaacaatct   9720
gaggatgaag gtgtcacagc tcacccagac cgagagaaac ccacaggaga agcgaacaa    9780
cttgtcaagc caagaatcgg aggagtgata cccagctttc ttgtacaaag tggtgatgac   9840
tcgaattttcc ccgatcgttc aaacatttgg caataaagtt tcttaagatt gaatcctgtt  9900
gccggtcttg cgatgattat catataattt ctgttgaatt acgttaagca tgtaataatt   9960
aacatgtaat gcatgacgtt atttatgaga tgggttttta tgattagagt cccgcaatta  10020
tacatttaat acgcgataga aaacaaaata tagcgcgcaa actaggataa attatcgcgc  10080
gcggtgtcat ctatgttact agatcgctcg acgcggccgc catggcctct agtggatcag  10140
cttgcatgcc tgcaggtcac tggattttgg ttttaggaat tagaaatttt attgatagaa  10200
gtattttaca aatacaaata catactaagg gtttcttata tgctcaacac atgagcgaaa  10260
ccctataaga cccctaattc ccttatctgg gaactactca cacattattc tggagaaaaa  10320
tagagagaga tagatttgta gagagagact ggtgattttt gcggactccg gtcggcatct  10380
actctattcc tttgccctcg gacgagtgct ggggcgtcgg tttccactat cggcgagtac  10440
ttctacacag ccatcggtcc agacggccgc gcttctgcgg gcgatttgtg tacgcccgac  10500
agtcccggct ccggatcgga cgattgcgtc gcatcgaccc tgcgcccaag ctgcatcatc  10560
gaaattgccg tcaaccaagc tctgatagag ttggtcaaga ccaatgcgga gcatatacgc  10620
ccggagccgc ggcgatcctg caagctccgg atgcctccgc tcgaagtagc gcgtctgctg  10680
ctccatacaa gccaaccacg gcctccagaa gaagatgttg gcgacctcgt attgggaatc  10740
cccgaacatc gcctcgctcc agtcaatgac cgctgttatg cggccattgt ccgtcaggac  10800
attgttggag ccgaaatccg cgtgcacgag gtgccggact cggggcagt cctcggccca   10860
aagcatcagc tcatcgagag cctgcgcgac ggacgcactg acggtgtcgt ccatcacagt  10920
ttgccagtga tacacatggg gatcagcaat cgcgcatatg aaatcacgcc atgtagtgta  10980
```

-continued

```
ttgaccgatt ccttgcggtc cgaatgggcc gaacccgctc gtctggctaa gatcggccgc   11040
agcgatcgca tccatggcct ccgcgaccgg ctgcagaaca gcgggcagtt cggtttcagg   11100
caggtcttgc aacgtgacac cctgtgcacg gcgggagatg caataggtca ggctctcgct   11160
gaattcccca atgtcaagca cttccggaat cgggagcgcg gccgatgcaa agtgccgata   11220
aacataacga tctttgtaga aaccatcggc gcagctattt acccgcagga catatccacg   11280
ccctcctaca tcgaagctga aagcacgaga ttcttcgccc tccgagagct gcatcaggtc   11340
ggagacgctg tcgaactttt cgatcagaaa cttctcgaca gacgtcgcgg tgagttcagg   11400
ctttttcata tcttattgcc ccccgggcc ctcgacctgc agaagtaaca ccaaacaaca    11460
gggtgagcat cgacaaaaga aacagtacca agcaaataaa tagcgtatga aggcagggct   11520
aaaaaaatcc acatatagct gctgcatatg ccatcatcca agtatatcaa gatcaaaata   11580
attataaaac atacttgttt attataatag ataggtactc aaggttagag catatgaata   11640
gatgctgcat atgccatcat gtatatgcat cagtaaaacc cacatcaaca tgtataccta   11700
tcctagatcg atcccgtctg cggaacggct agagccatcc caggattccc caaagagaaa   11760
cactggcaag ttagcaatca gaacgtgtct gacgtacagg tcgcatccgt gtacgaacgc   11820
tagcagcacg gatctaacac aaacacggat ctaacacaaa catgaacaga agtagaacta   11880
ccgggccta accatggacc ggaacgccga tctagagaag gtagagaggg gggggggggg     11940
aggacgagcg gcgtaccttg aagcggaggt gccgacgggt ggatttgggg gagatctggt   12000
tgtgtgtgtg tgcgctccga acaacacgag gttgggaaa gagggtgtgg aggggtgtc    12060
tatttattac ggcgggcgag gaaggaaag cgaaggagcg gtgggaaagg aatcccccgt    12120
agctgccggt gccgtgagag gaggaggagg ccgcctgccg tgccggctca cgtctgccgc   12180
tccgccacgc aatttctgga tgccgacagc ggagcaagtc caacggtgga gcggaactct   12240
cgagaggggt ccagaggcag cgacagagat gccgtgccgt ctgcttcgct tggcccgacg   12300
cgacgctgct ggttcgctgg ttggtgtccg ttagactcgt cgatcgacgg cgtttaacag   12360
gctggcatta tctactcgaa acaagaaaaa tgtttcctta gttttttaa tttcttaaag    12420
ggtatttgtt taatttttag tcactttatt ttattctatt ttatatctaa attattaaat   12480
aaaaaaacta aaatagagtt ttagtttct taatttagag gctaaaatag aataaaatag    12540
atgtactaaa aaaattagtc tataaaaacc attaaccta aaccctaaat ggatgtacta    12600
ataaaatgga tgaagtatta taggtgaa gctatttgca aaaaaaagg agaacacatg      12660
cacactaaaa agataaaact gtagagtcct gttgtcaaaa tactcaattg tcctttagac   12720
catgtctaac tgttcattta tatgattctc taaaacactg atattattgt agtactatag   12780
attatattat tcgtagagta aagtttaaat atatgtataa agatagataa actgcacttc   12840
aaacaagtgt gacaaaaaaa atatgtggta attttttata acttagacat gcaatgctca   12900
ttatctctag agagggggcac gaccgggtca cgctgcactg cagactacta ga          12952
```